(12) United States Patent  (10) Patent No.: US 9,198,756 B2
Aklog et al.  (45) Date of Patent: Dec. 1, 2015

(54) TISSUE RESTRAINING DEVICES AND METHODS OF USE

(75) Inventors: Lishan Aklog, Scottsdale, AZ (US); Brian deGuzman, Paradise Valley, AZ (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 0 days.

(21) Appl. No.: 13/476,010

(22) Filed: May 20, 2012

(65) Prior Publication Data

US 2012/0290077 A1  Nov. 15, 2012

Related U.S. Application Data

(63) Continuation-in-part of application No. 13/300,328, filed on Nov. 18, 2011.

(60) Provisional application No. 61/414,990, filed on Nov. 18, 2010, provisional application No. 61/444,554, filed on Feb. 18, 2011, provisional application No. 61/487,906, filed on May 19, 2011, provisional application No. 61/487,914, filed on May 19, 2011.

(51) Int. Cl.
*A61F 2/24* (2006.01)
*A61B 17/04* (2006.01)

(52) U.S. Cl.
CPC ........... *A61F 2/2451* (2013.01); *A61B 17/0401* (2013.01); *A61F 2/2454* (2013.01); *A61F 2/2457* (2013.01); *A61F 2/2466* (2013.01); *A61B 2017/0409* (2013.01);

(Continued)

(58) Field of Classification Search
CPC ... A61F 2/2442; A61F 2/2448; A61F 2/2454; A61F 2/2451; A61F 2/2457; A61B 2017/0496
USPC .................................................. 623/2.36, 2.37
See application file for complete search history.

(56) References Cited

U.S. PATENT DOCUMENTS 1,590,459 A  6/1926  Vondersaar
4,006,740 A  2/1977  Volkov et al.
(Continued)

FOREIGN PATENT DOCUMENTS

WO  WO 87/05489  9/1987
WO  WO 91/02500  3/1991
(Continued)

OTHER PUBLICATIONS

International Search Report and Written Opinion for PCT/US2012/038781 mailed on Sep. 7, 2012.
(Continued)

*Primary Examiner* — Brian Dukert
(74) *Attorney, Agent, or Firm* — Greenberg Traurig, LLP; Chinh H. Pham; Roman Fayerberg

(57) ABSTRACT

Tissue restraining systems and devices as well as methods of using these devices are disclosed herein. According to aspects illustrated herein, there is provided a tissue restraining device that may include an annuloplasty member having one or more contact points along a portion of the annuloplasty member in a spaced relation to one another. The tissue restraining device may also include a second anchor for placement in a substantially opposing, spaced relation to the annuloplasty member. A restraining matrix may extend from the contact points of the annuloplasty member to the second anchor.

18 Claims, 47 Drawing Sheets

(52) U.S. Cl.
CPC *A61B 2017/0412* (2013.01); *A61B 2017/0441* (2013.01); *A61B 2017/0496* (2013.01)

(56) References Cited

U.S. PATENT DOCUMENTS

| | | | |
|---|---|---|---|
| 4,042,979 A | 8/1977 | Angell | |
| 4,784,125 A | 11/1988 | Monticelli et al. | |
| 5,306,296 A | 4/1994 | Wright et al. | |
| 5,593,424 A | 1/1997 | Northrup, III | |
| 5,676,697 A | 10/1997 | McDonald | |
| 5,716,397 A | 2/1998 | Myers | |
| 5,749,825 A | 5/1998 | Fischell et al. | |
| 5,971,984 A | 10/1999 | Taylor et al. | |
| 6,102,945 A | 8/2000 | Cambell | |
| 6,210,429 B1 | 4/2001 | Vardi et al. | |
| 6,210,432 B1 | 4/2001 | Solem et al. | |
| 6,223,087 B1 | 4/2001 | Williams | |
| 6,325,826 B1 | 12/2001 | Vardi et al. | |
| 6,332,893 B1 | 12/2001 | Mortier et al. | |
| 6,419,695 B1 | 7/2002 | Gabbay | |
| 6,428,417 B2 | 8/2002 | Wakizaka et al. | |
| 6,723,038 B1 | 4/2004 | Schroeder et al. | |
| 6,726,717 B2 | 4/2004 | Alfieri et al. | |
| 6,764,572 B2 | 7/2004 | Shimizu et al. | |
| 6,793,673 B2 | 9/2004 | Kowalsky et al. | |
| 6,797,002 B2 | 9/2004 | Spence et al. | |
| 6,805,710 B2 | 10/2004 | Bolling et al. | |
| 6,824,582 B2 | 11/2004 | Wilson | |
| 6,890,353 B2 | 5/2005 | Cohn et al. | |
| 6,908,478 B2 | 6/2005 | Alferness et al. | |
| 6,921,407 B2 | 7/2005 | Nguyen et al. | |
| 6,976,995 B2 | 12/2005 | Mathis et al. | |
| 6,997,950 B2 | 2/2006 | Chawla | |
| 7,070,618 B2 | 7/2006 | Streeter | |
| 7,125,421 B2 | 10/2006 | Tremulis et al. | |
| 7,144,363 B2 | 12/2006 | Pai et al. | |
| 7,166,126 B2 | 1/2007 | Spence et al. | |
| 7,166,127 B2 | 1/2007 | Spence et al. | |
| 7,247,134 B2 | 7/2007 | Vidlund et al. | |
| 7,291,168 B2 | 11/2007 | Macoviak et al. | |
| 7,311,729 B2 | 12/2007 | Mathis et al. | |
| 7,351,260 B2 | 4/2008 | Nieminen et al. | |
| 7,374,572 B2 | 5/2008 | Gabbay | |
| 7,485,143 B2 | 2/2009 | Webler et al. | |
| 7,527,646 B2 | 5/2009 | Rahdert et al. | |
| 7,527,647 B2 | 5/2009 | Spence | |
| 7,632,308 B2 | 12/2009 | Loulmet | |
| 7,828,842 B2 | 11/2010 | Nieminen et al. | |
| 7,976,551 B1 | 7/2011 | Gutfinger et al. | |
| 8,052,751 B2 | 11/2011 | Aklog et al. | |
| 8,133,272 B2 | 3/2012 | Hyde | |
| 2003/0120340 A1 | 6/2003 | Liska et al. | |
| 2004/0039371 A1 | 2/2004 | Tockman et al. | |
| 2004/0127982 A1 | 7/2004 | Machold et al. | |
| 2004/0143323 A1 | 7/2004 | Chawla | |
| 2005/0004665 A1 | 1/2005 | Aklog | |
| 2005/0004668 A1 | 1/2005 | Aklog et al. | |
| 2005/0070999 A1 | 3/2005 | Spence | |
| 2005/0075727 A1* | 4/2005 | Wheatley | 623/2.17 |
| 2005/0119734 A1 | 6/2005 | Spence et al. | |
| 2005/0149182 A1 | 7/2005 | Alferness et al. | |
| 2006/0020336 A1 | 1/2006 | Liddicoat | |
| 2006/0241340 A1 | 10/2006 | Schroeder et al. | |
| 2006/0247492 A1 | 11/2006 | Streeter | |
| 2007/0050020 A1 | 3/2007 | Spence | |
| 2008/0195126 A1 | 8/2008 | Solem | |
| 2010/0063586 A1 | 3/2010 | Hasenkam et al. | |
| 2010/0298930 A1 | 11/2010 | Orlov | |
| 2011/0066231 A1 | 3/2011 | Cartledge et al. | |
| 2011/0257728 A1 | 10/2011 | Kuehn | |

FOREIGN PATENT DOCUMENTS

| | | |
|---|---|---|
| WO | WO 98/18411 | 5/1998 |
| WO | WO 99/13802 | 3/1999 |
| WO | WO 01/47438 | 7/2001 |
| WO | WO 01/89418 | 11/2001 |
| WO | WO 03/028558 | 4/2003 |
| WO | WO 03/037227 | 5/2003 |
| WO | 2009-072114 | 6/2009 |

OTHER PUBLICATIONS

International Search Report issued in International Application PCT/US2011/61526 mailed on May 21, 2012.

* cited by examiner

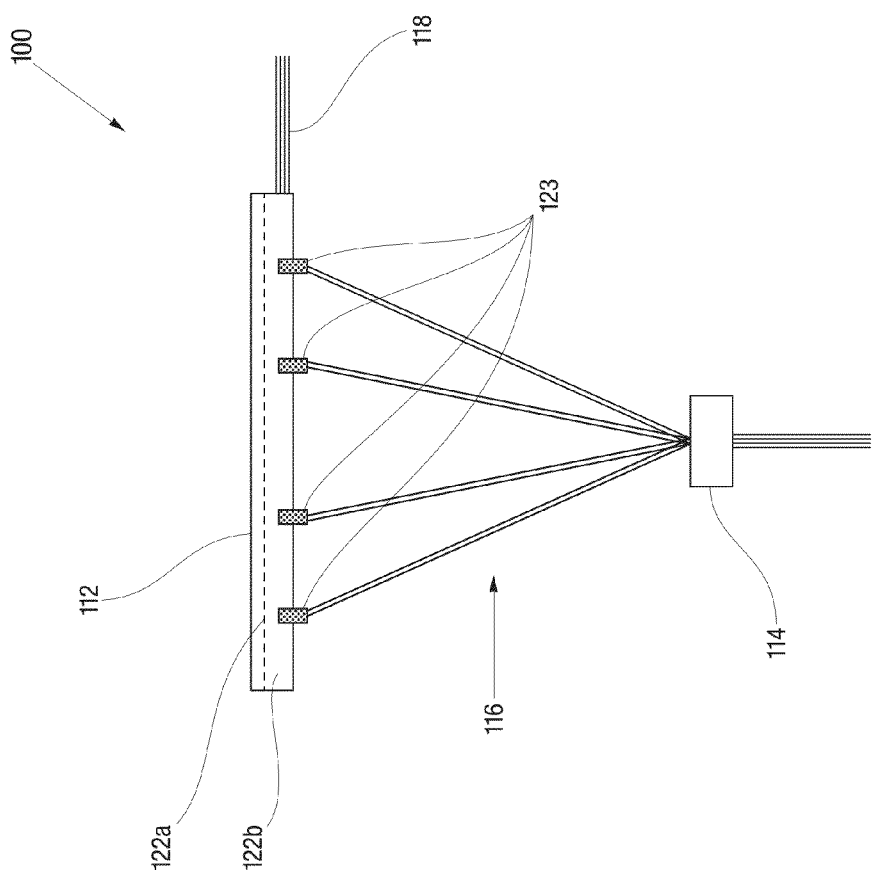

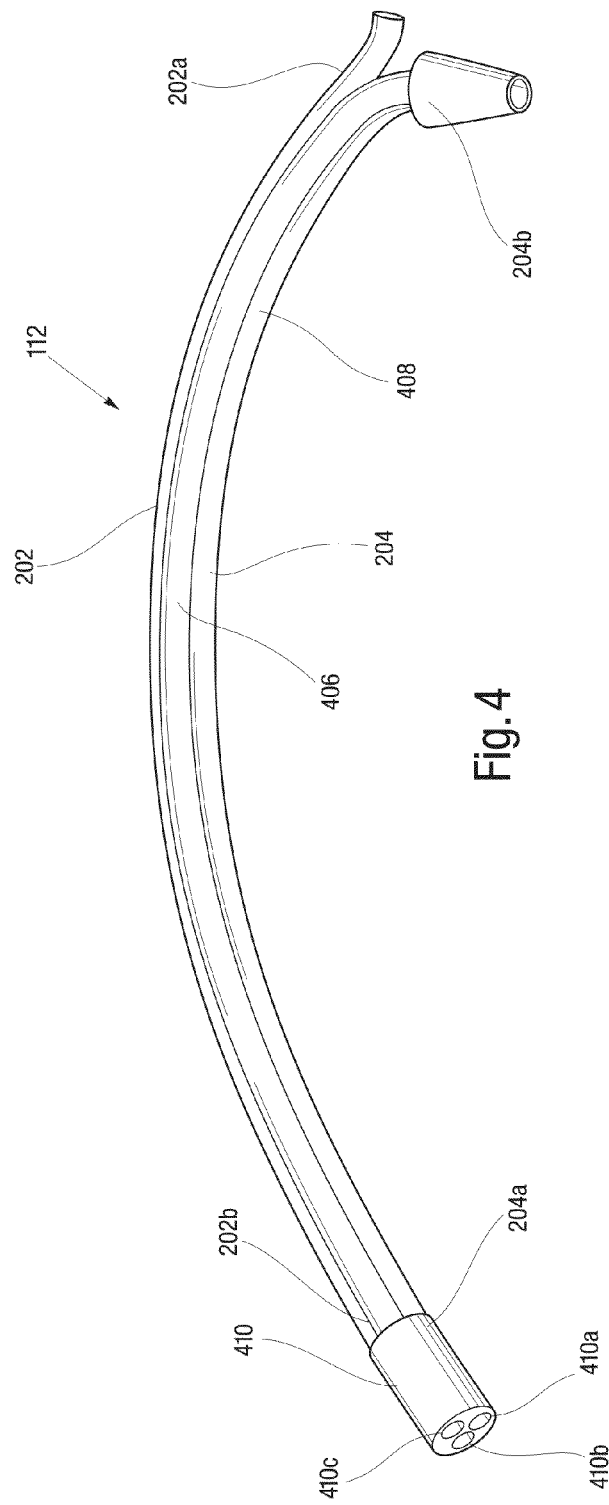
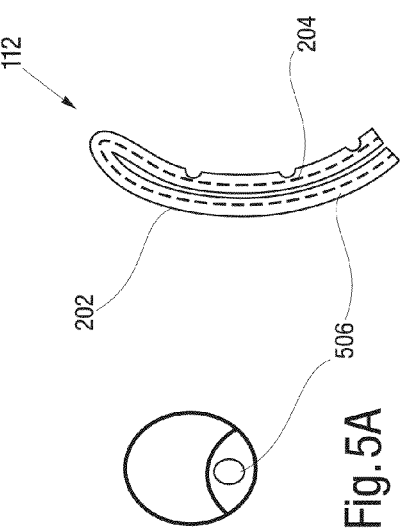

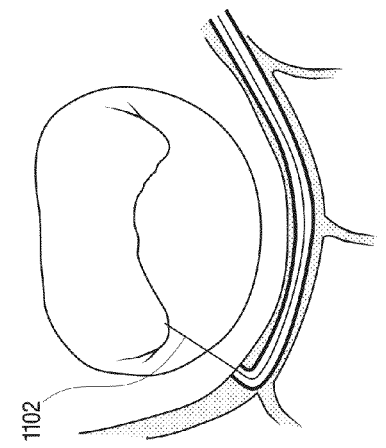
Fig. 11A
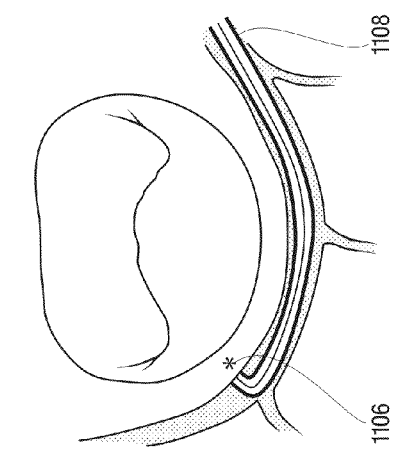
Fig. 11C
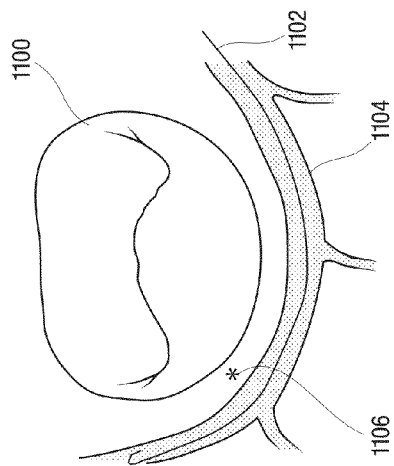
Fig. 11E
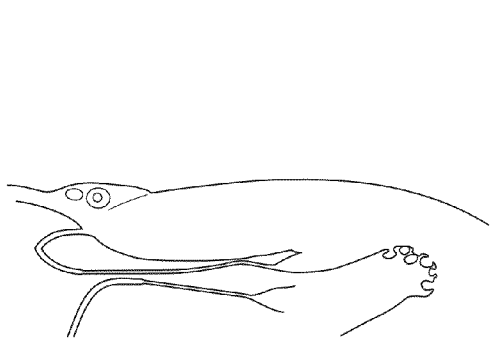
Fig. 11B / Fig. 11D / Fig. 11F

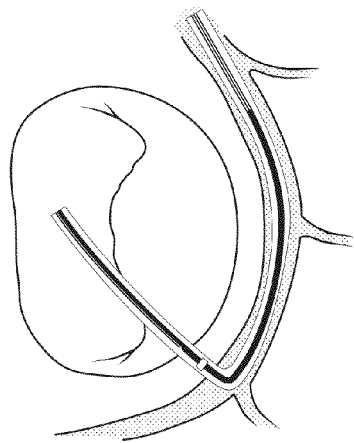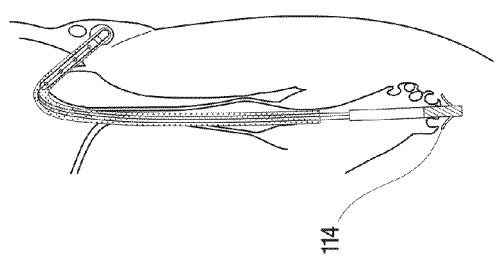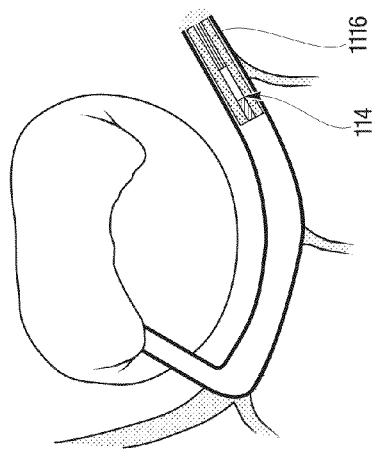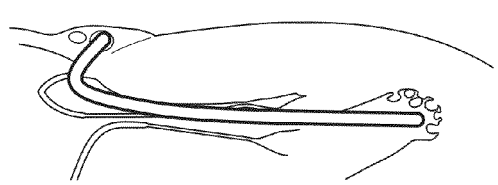

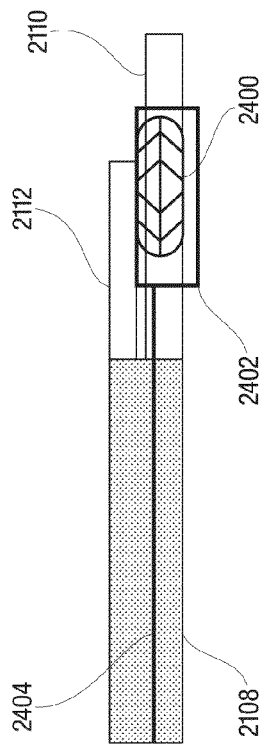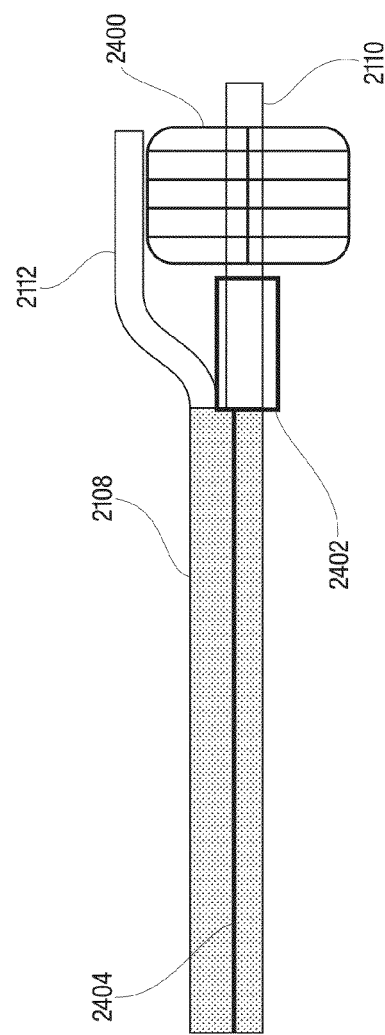

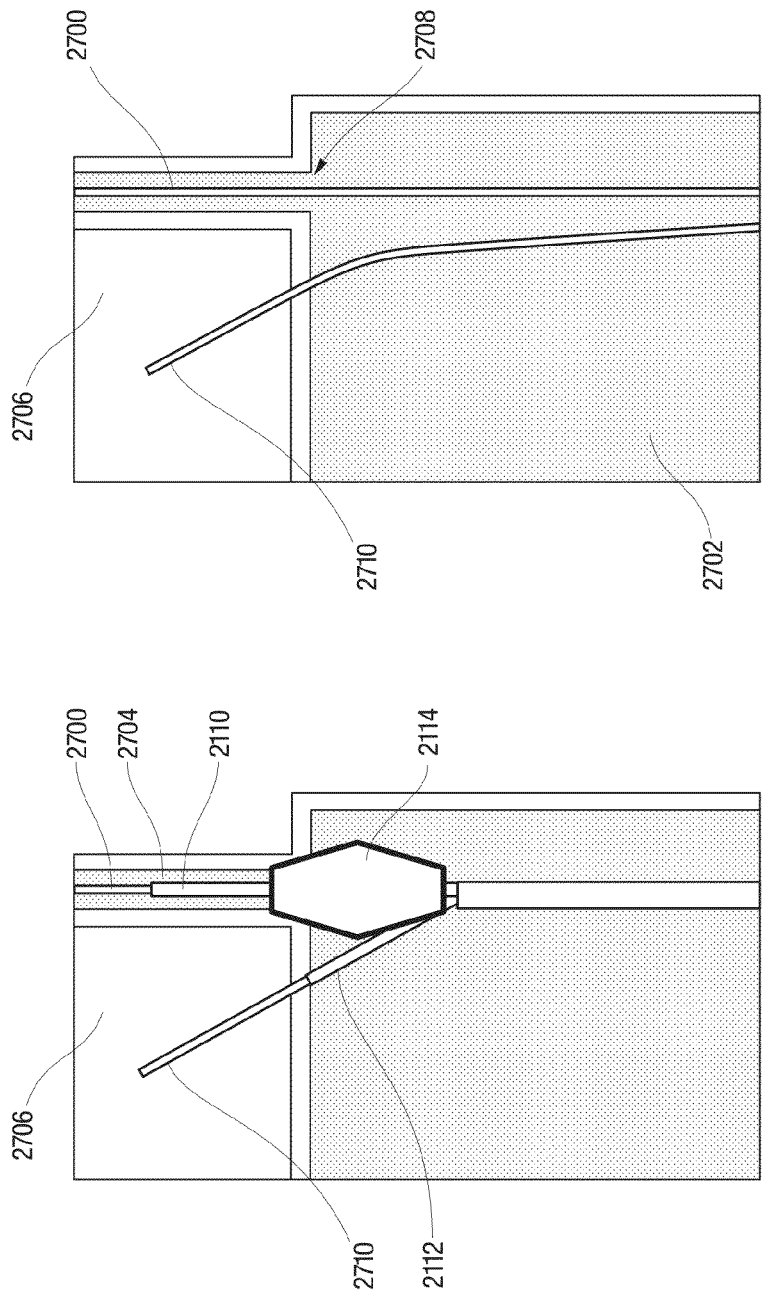

TISSUE RESTRAINING DEVICES AND METHODS OF USE

RELATED APPLICATIONS

This application is a continuation in part of and claims priority to and the benefit of U.S. patent application Ser. No. 13/300,328, filed on Nov. 18, 2011, and which claims priority to and the benefit of U.S. Provisional Application No. 61/414,990 filed Nov. 18, 2010, U.S. Provisional Application No. 61/444,554 filed Feb. 18, 2011, U.S. Provisional Application No. 61/487,914 filed May 19, 2011, and U.S. Provisional Application No. 61/487,906 filed May 19, 2011. All of these applications are incorporated herein by reference in their entireties for the teachings therein.

BACKGROUND

Various disease processes can impair the proper functioning of one or more of valves of human heart. These include degenerative processes (e.g., Barlow's Disease, fibroblastic deficiency), inflammatory processes (e.g., Rheumatic Heart Disease) and infectious processes (e.g., endocarditis). In addition, damage to the ventricle from prior heart attacks (i.e., myocardial infarction secondary to coronary artery disease) or other heart diseases (e.g., cardiomyopathy) can distort the valve's geometry causing it to dysfunction.

The benefits of valve repair over replacement are well established in the cardiac surgical literature in all types of valve dysfunction and in nearly all disease states. Patients undergoing valve repair have been shown to live longer, with better preservation of cardiac function. The vast majority of patients with mitral or tricuspid regurgitation can have their valves successfully repaired instead of replaced. The likelihood of a successful repair, however, is highly dependent on the skill, knowledge and experience of the individual surgeon. Although most surgeons are comfortable performing simple valve repairs (annuloplasty members, limited leaflet resections, etc.), many rarely perform valve repairs and only a small minority of surgeons are comfortable at more complex valve repairs. Most surgeons have inadequate knowledge and training in these techniques and, even if they had the technical ability, they do not encounter enough patients to feel comfortable with complex cases. This variability in surgical skill is reflected in the wide range of valve repair rates among different centers. High-volume, experienced centers routinely report valve repair rates over 90% while the national average is only 20-30%.

Since they involve work inside the heart chambers, conventional procedures for replacing or repairing cardiac valves require the use of the heart-lung machine (cardiopulmonary bypass) and stopping the heart by clamping the ascending aorta and perusing it with high-potassium solution (cardioplegic arrest). Although most patients tolerate limited periods of cardiopulmonary bypass and cardiac arrest well, these maneuvers are known to adversely affect all organ systems. The most common complications of cardiopulmonary bypass and cardiac arrest are stroke, myocardial "stunning" or damage, respiratory failure, kidney failure, bleeding and generalized inflammation. If severe, these complications can lead to permanent disability or death. The risk of these complications is directly related to the amount of time the patient is on the heart-lung machine ("pump time") and the amount of time the heart is stopped ("crossclamp time"). Although the safe windows for pump time and cross clamp time depend on individual patient characteristics (age, cardiac reserve, comorbid conditions, etc.), pump times over 4 hours and clamp times over 3 hours can be concerning even in young, relatively healthy patients. Complex valve repairs can push these time limits even in the most experienced hands. Even if he or she is fairly well versed in the principles of mitral valve repair, a less experienced surgeon is often reluctant to spend 3 hours trying to repair a valve since, if the repair is unsuccessful, he or she will have to spend up to an additional hour replacing the valve. Thus, time is a major factor in deterring surgeons from offering the benefits of valve repair over replacement to more patients. Devices and techniques which simplify and expedite valve repair would go a long way to eliminating this deterrent.

Within recent years, there has been a movement to perform many cardiac surgical procedures "minimally invasively" using smaller incisions and innovative cardiopulmonary bypass protocols. The purported benefits of these approaches include less pain, less trauma and more rapid recovery. However the use of these minimally invasive procedures has been limited to a handful of surgeons at specialized centers. Even in their hands, the most complex valve repairs cannot be performed since dexterity is limited and the whole procedure moves more slowly. Devices and techniques which simplify valve repair have the potential to greatly increase the use of minimally invasive techniques which would significantly benefit patients.

SUMMARY

Tissue restraining systems and devices as well as methods of using these devices are disclosed herein. According to aspects illustrated herein, there is provided a tissue restraining device that may include a first anchor having one or more contact points along a portion of the first anchor in a spaced relation to one another. The tissue restraining device may also include a second anchor for placement in a substantially opposing relation to the first anchor. A restraining matrix may extend from the contact points of the first anchor to the second anchor.

According to aspects illustrated herein, there is also provided a method for treating a prolapsed mitral valve. The method may include a step of embedding an anchor into a tissue in a left ventricle and deploying another anchor in a left atrium. A restraining matrix may be extended between the anchors such that the restraining matrix is draped over the mitral valve. Next, the restraining matrix may be adjusted to correct a prolapsing segment of the mitral valve.

According to aspects illustrated herein, there is also provided a device for gaining access to a body organ that includes a first extension member and a second extension member in a substantially parallel relation to one another and coupled an elongated body, each having at least one inner lumen in communication with one or more inner lumens of the elongated member. The device may also include a deflection mechanism disposed on one of the extension members and configured to deflect the second extension member relative to the first extension member upon activation, such that the inner lumen of the second extension member is aligned with a body organ to which access is needed.

According to aspects illustrated herein, there is also provided a method for gaining access to the left atrium of a heart. The method may include a step of navigating a first extension member of an elongated device over a guidewire to position a distal tip of the first extension member in proximity to a coronary sinus ostium. Next, a second extension member of the elongated device may be deflected radially away form the first extension member. In the next step, another guidewire may be advanced through the second extension member to penetrate across tissue into the left atrium for subsequent delivery of an implant into the left atrium over the guidewire.

According to aspects illustrated herein, there is provided a tissue restraining device that may include an annuloplasty member for attachment to a valve annulus. The tissue restraining device may also include an anchor for placement in a spaced relation to the annuloplasty member. A restraining matrix may extend from the annuloplasty member to the anchor.

According to aspects illustrated herein, there is also provided a method for treating a prolapsed mitral valve. The method may include a step of attaching an annuloplasty member substantially along the valve annulus. Next, an anchor is embedded into a tissue in a left ventricle and deploying another anchor in a left atrium. A restraining matrix may subsequently be extended between the annuloplasty member and the anchor such that the restraining matrix is draped over the mitral valve. Next, the restraining matrix may be adjusted to correct a prolapsing segment of the mitral valve.

According to aspects illustrated herein, there is provided a kit for restraining tissue comprising that may include a restraining matrix having a proximal end and a distal end, with an attachment member disposed at the proximal end of the restraining matrix and designed to attach to an annuloplasty ring. The kit may further include an anchor configured for attachment to the distal end of the restraining matrix.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A and FIG. 1B illustrate embodiments of a tissue restraining device of the present disclosure.

FIG. 4 illustrates an embodiment of an anchor suitable for use in tissue restraining devices of the present disclosure.

FIG. 5 illustrates an embodiment of an anchor suitable for use in tissue restraining devices of the present disclosure.

FIGS. 11A-11L illustrate a method for mitral valve repair using a tissue restraining device of the present disclosure.

FIGS. 25A-25B illustrate another embodiment of a deflection device of the present disclosure.

FIGS. 28A-28F show an embodiment method of using a system for accessing a body organ of the present disclosure.

Figure 1B:
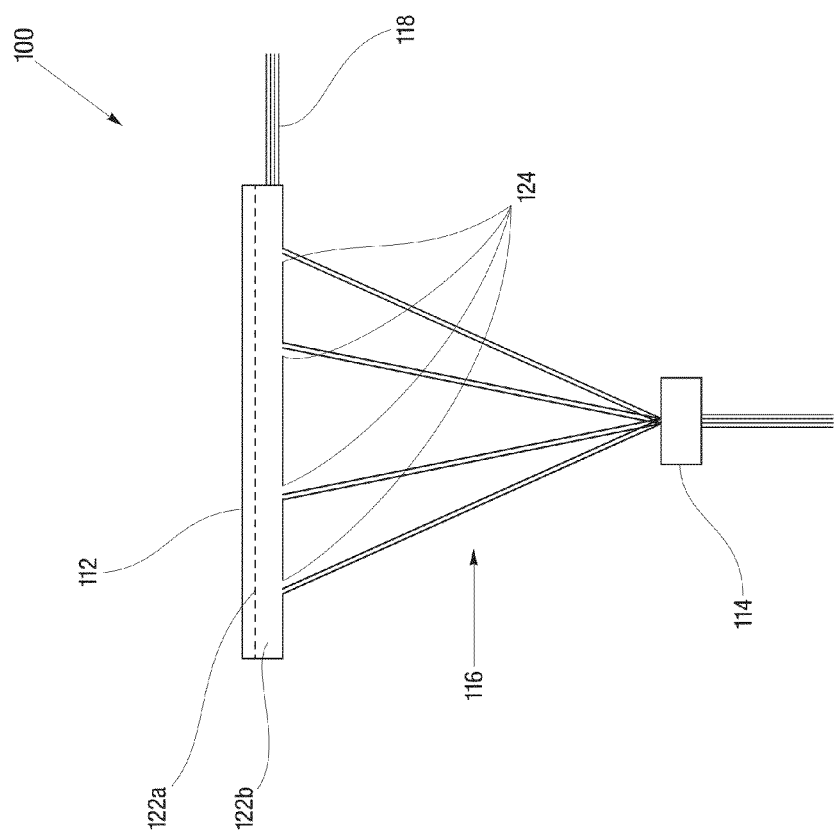

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

There is provided a tissue restraining device for minimally invasive repair of a prolapsing tissue. Referring to FIG. 1, a tissue restraining device 100 comprises a first anchor 112, a second anchor 114, and a restraining matrix 116 extending between the anchors 112, 114. The restraining matrix 116, in one embodiment, may be formed by one or more restraining cords 118. The restraining cords 118, in an embodiment may each be individually adjustable cord.

In an embodiment, as shown in FIG. 1A, the first anchor 112 may include one or more inner lumens 122a, 122b extending through at least a portion of the first anchor 112. In an embodiment, the inner lumens 112a, 122b may be sized to receive a guidewire therethrough. In an embodiment, inner lumens 122a, 122b can extend substantially for the entire length of the first anchor 112. In embodiments with multiple lumens, the lumens may be in adjacent relation to one another, concentric relation to one another, or a combination thereof. To the extent desired, the inner lumens 122a, 122b may be in communication with one another.

The first anchor 112 may further include one or more contact points 123 positioned along at least a portion of the first anchor. The contact points 123 can be the points at which the restraining cords 118 contact the first anchor 112. In an embodiment, a proximal end of each restraining cord 118 may be fixed to the first anchor 112 at contact points 123, such as by adhesive, weld or other similar attachments. In an embodiment, as shown in FIG. 1B, the contact points 123 may be one or more of openings 124 positioned along at least a portion of the first anchor 112, such that the restraining cords 118 can be inserted into the first anchor 112 or can extend out from the first anchor, through openings 124. In an embodiment, the first anchor includes a plurality of openings 124. In an embodiment, the openings 124 may be spaced apart, evenly or unevenly, from one another and may be configured to accept one or more individual cords of the plurality of restraining cords 118. One or both inner lumens 122a, 122b may be in communication with the plurality of openings 124, such that the restraining cords 118 can be passed through the inner lumens 122a, 122b and out of the plurality of openings 124 to form the restraining matrix 116.

As is described in more detail below, the first anchor 112 may be of any shape, but such factors as, for example, the desired shape of the restraining matrix 116 and the shape or location of a tissue to be restrained may play a role when shaping the first anchor 112. In an embodiment, the first anchor 112 may be provided with a shape that approximates the shape of tissue or structure to which the first anchor 112 is to be attached. In this manner, when the first anchor 112 is deployed, the first anchor 112 does not act to substantially alter the natural shape of the tissue or structure to which the first anchor 112 is attached. By way of a non-limiting example, the first anchor 112 for a tissue restraining device of the present disclosure to be used for restraining a prolapsed mitral valve, which is generally circular, may have a generally elongated shape with inwardly curved ends.

In an embodiment, the first anchor 112 may be designed for secured placement at or near a tissue to be restrained. The first anchor 112 may be permitted to secure to tissue based on (a) its construction, such as, for example, if the first anchor includes design elements configured to grip a tissue therebetween; (b) its shape, such as, for example, if the first anchor is shaped to enclose a tissue or penetrate a tissue, (c) its secondary design elements, such as, for example, by using anchoring pins or stents, or (d) a combination thereof.

Figure 2:
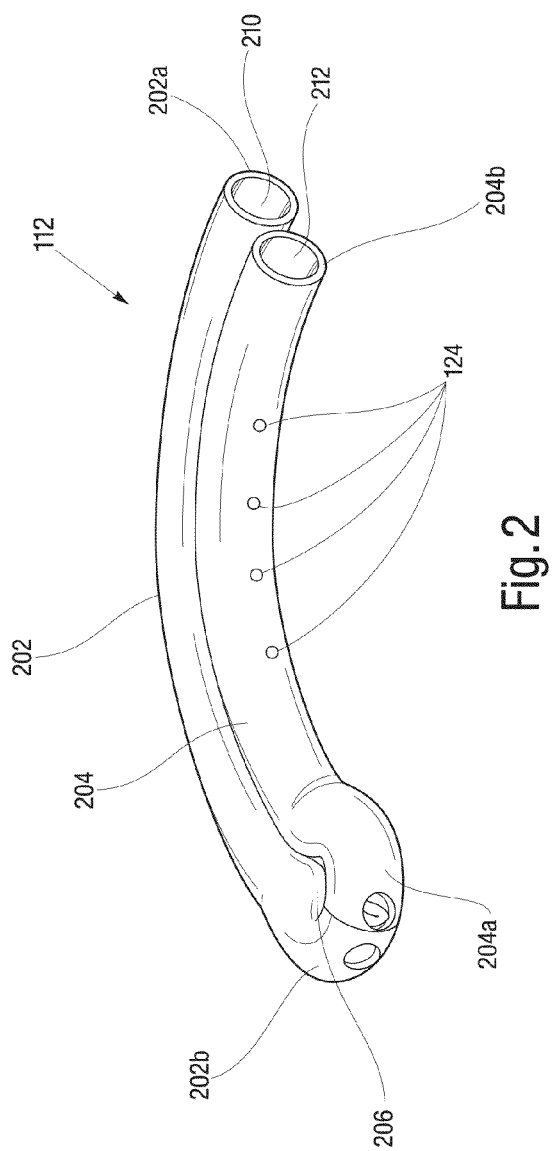
FIG. 2 illustrates an embodiment of an anchor suitable for use in tissue restraining devices of the present disclosure.

FIG. 2 illustrates a non-limiting embodiment of the first anchor 112, in which the first anchor 112 includes a first arm 202, which has a first end 202a and a second end 202b, and a second arm 204, which has a first end 204a and a second end 204b. As will be described in detail below, the arms 202, 204 may be connected in such a manner so as to cooperate with one another to facilitate pinching a structure, such as a tissue, between the arms. In an embodiment, the first arm 202 may be placed into a coronary sinus and the second arm 204 may be placed in the left atrium, and the arms 202, 204 may be biased toward one another to pinch the common wall between the coronary sinus and the left atrium, thus securing the tissue restraining device in place in proximity to a mitral valve. In an embodiment, the second end 202b of the first arm 202 may be connected to the first end 204a of the second arm 204, forming an apex 206. It should be noted, however, that the first arm 202 may be connected to the second arm 204 anywhere along the length of the second arm 204, and vice versa. For example, in an embodiment shown in FIG. 3, the first anchor 112 includes a first arm 202 connected to a second arm 204 in the middle section of the second arm 204. The arms 202, 204 may be of similar length or different lengths. In an embodiment, the second arm 204 is longer than the first arm 202.

The first arm 202, as shown in FIG. 2, may include one or more inner lumens 210 extending through at least a portion of the first arm 202. The second arm 204 may also include one or more inner lumens 212 extending through at least a portion of the second arm 204. In embodiments with multiple lumens in each arm, the lumens in each arm while may be adjacent to one another, concentric in relation to one another, or a combination thereof. In an embodiment, each arm may include two lumens, each being adjacent to the another. In addition, the second arm 204 may include a plurality of openings 124 positioned along a side of the second arm 204 in spaced relation to one another, being in communication with the one or more inner lumens 210, 212.

FIG. 4 illustrates another non-limiting embodiment of the first anchor 112. The first anchor 112, as shown, includes a first arm 202, having a first end 202a and a second end 202b, and a second arm 204, having a first end 204a and a second end 204b. The arms 202, 204 may be connected through an end cup 410, which can act to bias the arms 202, 204 toward one another. In an embodiment, the hub 410 may include a number of channels 410a, 410b, 410c. These channels 410a, 410b, 410c may be in communication with the inner lumens of the first arm 202 and the second arm 204 so as to allow a guidewire or the restraining cords 118 to pass through the hub into the first arm 202 or the second arm 204. In an embodiment, the second arm 204 can comprise multiple sub-arms 406 and 408, with each of the sub-arms 406, 408 having one or more inner lumens. It will of course be understood that various other embodiments in terms of the number of sub-arms, and whether the second arm 204, the first arm 202, or both can include multiple sub-arms are possible.

In an embodiment, the first arm 202 and the second arm 204 may be biased toward one another in order to facilitate a secured placement of the first anchor to a tissue to be restrained or in proximity to such tissue. This can be achieved in a variety of ways. In an embodiment shown in FIG. 2, the apex 206 may be shaped in such a way as to bias the arms 202 and 204 toward one another. In another embodiment shown in FIG. 3, the first arm 202 may be connected to the second arm 204 by a hinge 306, which can force the arms toward one another. In yet another embodiment shown in FIG. 4, the second end 202b of the first arm 202 and the first end 204a of the second arm 204 may be inserted into the end cup 401, which can act to bias the arms 202, 204 toward one another. FIGS. 5A-5B demonstrate yet another embodiment, in which the first anchor 112 comprises a first arm 202 and a second arm 204, wherein a shape-memory wire 506 may extend along the arms 202, 204 to bias the arms 202, 204 toward one another when the first anchor 112 is deployed. Of course, a combination of the foregoing methods or any other method, in addition to or instead of the foregoing methods, may be employed to bias the arms toward one another and still remain within the spirit and scope of the present invention.

In an embodiment, the first anchor 112 may be made of any medical grade, biocompatible material. Depending on whether a tissue to be restrained by the instant device requires a permanent or only a temporary support, the first anchor may be made of a bioresorbable or non-bioresorbable material.

Suitable non-bioresorbable materials include, but are not limited to, metals such as titanium, nickel-titanium alloy, and stainless steel, and plastics, such as polyethylene, polypropylene, and polyurethane, among many others. Suitable bioresorbable materials include, but are not limited to, polyglycolic acid, polylactic acid, and polydioxanone, among many others.

To facilitate the deployment of the first anchor 112, in some embodiments one or both arms 202, 204 of the first anchor 112 may comprise a shape memory material, such as nickel-titanium alloy or nitinol, copper-zinc-aluminum alloy, copper-aluminum-nickel alloy, iron-manganese-silicon alloy, iron-nickel-aluminum alloy, gold-cadmium alloy, or combinations thereof. In an embodiment, the first anchor 112 may be made of a soft, multi-lumen plastic tubing having a nitinol wire disposed in one of its inner lumens, as shown in FIGS. 5A-5B. Alternatively or additionally, the first anchor 112 may be made of a shape memory tubing.

Figure 30:
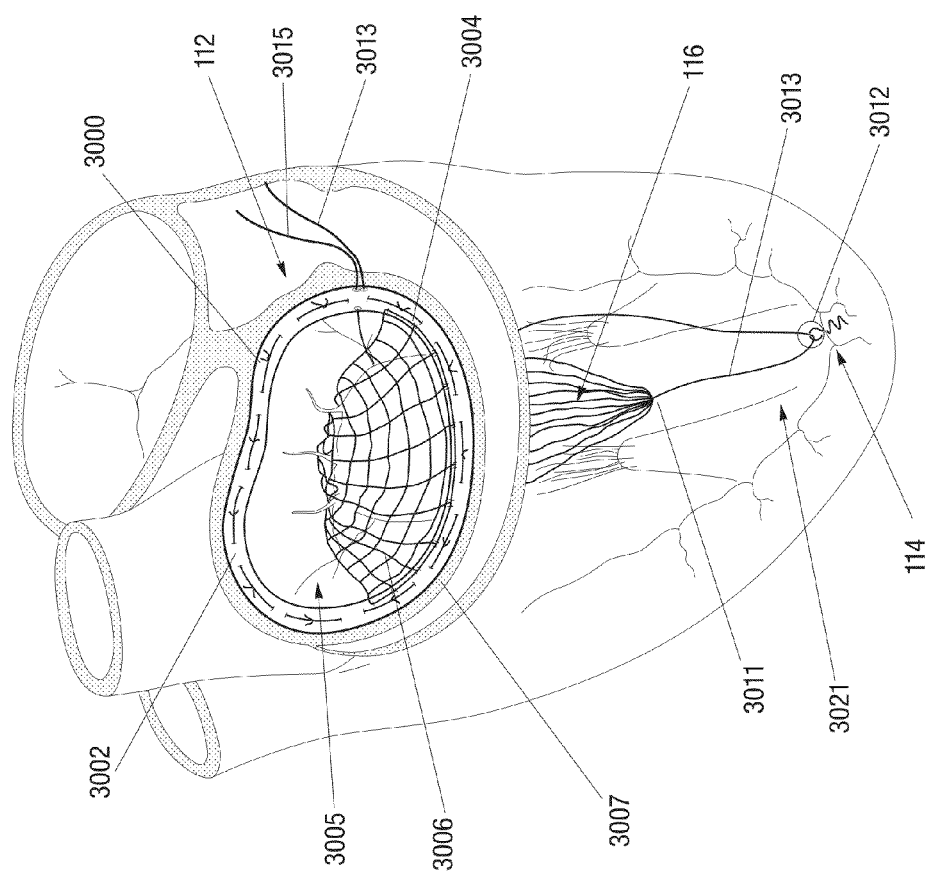
FIG. 30 and FIG. 31 illustrate an embodiment of a tissue restraining device having an annuloplasty member.

In an embodiment, as shown in FIG. 30, the first anchor 112 may be an annuloplasty member 3000 that may be implanted into a defective valve 3005 substantially along a portion of a valve annulus 3007. In an embodiment, the annuloplasty member 3000 may be conformable to the movement of the surface of the valve annulus. The annuloplasty member 3000 may include an inner core made of metal, such as stainless steel or titanium, or of a flexible material, such as silicone rubber or Dacron cordage, covered with a biocompatible fabric or cloth. The annuloplasty member 3000 of the present disclosure may be rigid, semi-rigid or flexible, and may form a complete continuous ring, a split ring or a partial ring or band. Further, the annuloplasty member 3000 may be provided in one of several shapes, including, but not limited to, circular, D- or "kidney" shaped, C-shaped, irregular shapes or other shapes suitable for implantation into a heart valve. In an embodiment, the annuloplasty member 3000 may be specifically designed for the mitral or tricuspid valve repair. In an embodiment, the annuloplasty member 3000 of the present disclosure is a one-piece ring or band. Alternatively, the annuloplasty member 3000 of the present disclosure is formed with two or more interconnected pieces.

The annuloplasty member 3000 may be attached to tissue in proximity to the valve annulus 3007 by a variety of conventional techniques. For example, the annuloplasty member 3000 may implanted into the defective valve by means of a plurality of interrupted mattress sutures which may be sewn through the annuloplasty member 3000 and into the valve annulus 3007. Other suitable for attaching the annuloplasty member 3000 into the valve include, but are not limited to, a continuous running suture, interrupted simple (non-mattress) sutures, specialized clips or staples, or other means known and used in the art. In the embodiments where the annuloplasty member 3000 includes an outer layer of fabric or cloth, sutures, clips or staples can the annuloplasty member 3000 may be sutured or stapled to the valve 3005 through the fabric or cloth, but can of course also be sutured through both the inner core in addition to the fabric or cloth.

As shown in FIG. 30, the annuloplasty member 3000 may include an anterior section 3002 and a posterior section 3004. When the annuloplasty member 3000 is implanted into the valve 3005 the anterior section 3002 may be attached to the anterior portion of the valve annulus 3007. The posterior section 3004 of the annuloplasty member 3000 may be attached to the posterior portion of the valve annulus 3007. In an embodiment, the annuloplasty member 3000 may include commissural marks as guides to identify the approximate location of the valve commissaries and separate the annuloplasty member into the anterior section 3002 and posterior section 3004 to assist in orienting the annuloplasty member 3000 for implantation into the valve 3005.

Figure 31:
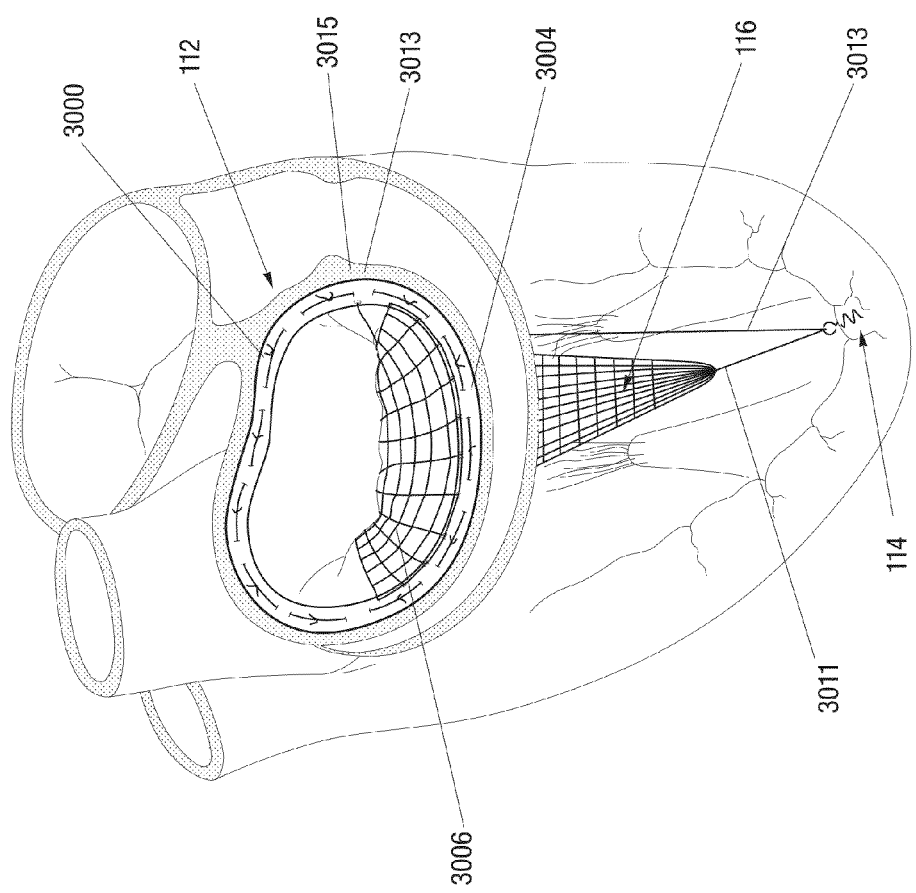

Depending on whether the tissue restraining device 100 is used to repair a prolapse in the posterior leaflet, anterior leaflet, or both, the restraining matrix 116 can be attached to the posterior section 3004, anterior section 3002, or a restraining matrix can be attached to both the posterior section 3004 and the anterior section 3002. By way of non-limiting example, FIGS. 30 and 31 illustrate the restraining matrix 116 attached to the posterior section 3004 and this embodiment is described below, however, the restraining matrix 116 can be attached to the anterior section 3002 in a similar manner. As shown in FIGS. 30 and 31, the restraining matrix 116 may, in an embodiment, be attached to the posterior section 3004 of the annuloplasty member 3000. In this manner, when the annuloplasty member 3000 is implanted, the restraining matrix 116 may be passed into the left ventricle to drape over the posterior leaflet 3006 of the valve 3005 to restrain the posterior leaflet 3006. The matrix 116, in an embodiment, may be formed from a plurality of restraining cords 118 that extend from a plurality of contact points disposed along the posterior section 3004 of the annuloplasty member 3000. In an embodiment, the plurality of restraining cords 118 can pass through an interior lumen within the annuloplasty member 3000 and exit the annuloplasty member 3000 through a plurality of spaced apart openings disposed along the posterior section 3004. In an embodiment, the restraining matrix 116 is permanently attached to the annuloplasty member. In an alternative embodiment, the restraining matrix 116 may be removably attached to the annuloplasty member 3000. To that end, in an embodiment, the end of the restraining matrix to be attached to the annuloplasty member 3000, or another type of the first anchor 112, may be equipped with an attachment member that can removably attach the restraining matrix 116 to the annuloplasty member. In an embodiment, the attachment member may be an open tube configured to snap onto the annuloplasty member 3000. In an embodiment, the attachment member may include a plurality of hooks configured for insertion into the annular member 3000 to attach the restraining matrix to the annular member. In yet another embodiment, the restraining matrix 116 may be attached to the annuloplasty member 3000 by tying proximal ends of the restraining cords to the annuloplasty member 3000. Of course it will be understood that in some embodiments the attachment member may be configured to permanently attach the restraining matrix to the annuloplasty member 3000 or another type of the first anchor 112.

Similar to the first anchor 112, the second anchor 114 facilitates secure placement of the instant device in proximity to a tissue to be restrained. The second anchor 114 can also be made of any medical grade, biocompatible material as described in connection with the first anchor. The second anchor 114 may be made of the same or different material as the first anchor 112. As is described in more detail below, the second anchor 114 may be of any shape, but such factors as, for example, the desired shape of the restraining system and the shape or location of a tissue to be restrained may play a role when selecting a shape for the second anchor 114.

Figure 6A:
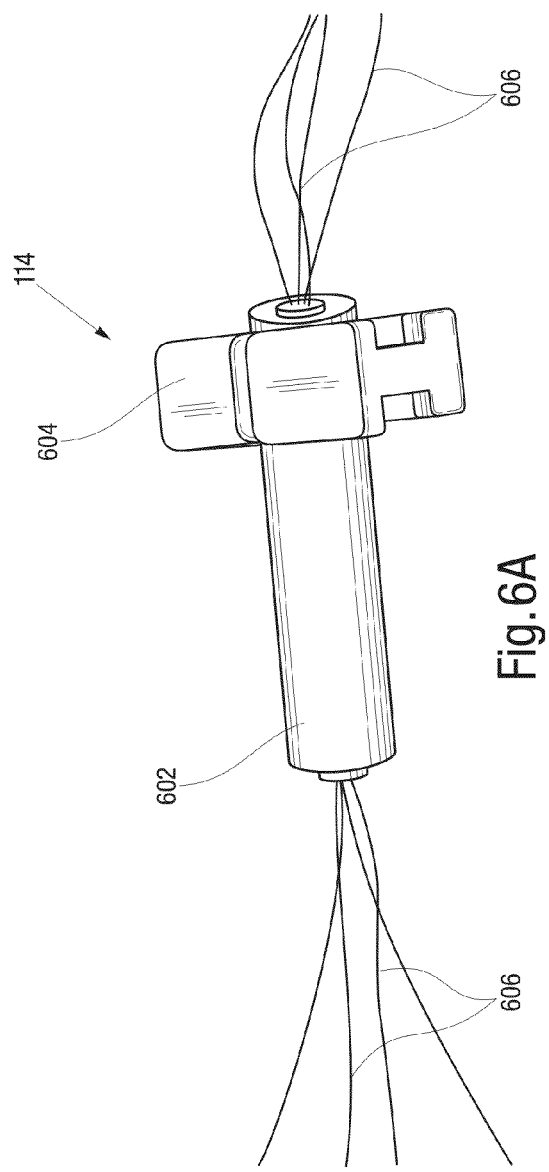
FIG. 6A and FIG. 6B illustrate embodiments of an anchor suitable for use in tissue restraining devices of the present disclosure.

By way of a non-limiting example, FIG. 6A illustrates an embodiment of a second anchor 114 suitable for use in a tissue restraining device of the present disclosure. The second anchor 114 comprises an anchoring member 602 and a locking member 604, one or both of which may be configured to accept a plurality of restraining cords 606 therethrough. Alternatively or additionally, a similar locking mechanism can be disposed on the first anchor 112 for locking proximal ends of individual restraining cords 118. Referring to FIG.

6B, in another embodiment, the second anchor 114 may be a helical coil with a sharpened distal tip, such that the second anchor 114 can be embedded into tissue by rotation. Other embodiments of the second anchor are also possible as long as the second anchor 114 can be securely implanted into tissue of the left ventricle and can provide sufficient support to the restraining matrix.

Referring back to FIG. 1A and FIG. 1B, the restraining matrix 116 may extend between the first anchor 112 and the second anchor 114. The matrix 116, in an embodiment, may be formed from a plurality of restraining cords 118 that extend from the plurality of contact points 123 of the first anchor 112 to the second anchor 114. In an another embodiment, the plurality of restraining cords 118 can be disposed within the first anchor 112 and exit the first anchor 112 through the plurality of openings 124. For example, the plurality of restraining cords 118 can be directed to pass through one or more inner lumens 122*a*, 122*b* and exit the first anchor 112 through the plurality of openings 124. In an embodiment, each of the plurality of openings 124 may accept one individual cord of the plurality of restraining cords 118. In another embodiment, each of the plurality of openings 124 may accept multiple individual cords of the plurality of restraining cords 118.

The individual restraining cords of the plurality of restraining cords 118 can extend for a distance until they can be attached, individually or as a bundle, to the second anchor 114. The number of individual cords, the size of the cords, and the distance between the cords may vary depending on particular characteristics of a tissue to be restrained and the application being implemented. In general, while the restraining matrix 116 needs to provide sufficient support to a tissue to be restrained, it may be desirable to minimize the surface area of the restraining matrix to decrease the amount of prosthetic material in the device and, which may improve the safety and cost effectiveness of the device. To that end, the individual cords, in embodiment, may be made from either monofilament or multifilament material.

In an embodiment, the restraining matrix 116 can be adjustable by adjusting the restraining cords 118 to provide a desired support to the prolapsing tissue. In an embodiment, individual cords 118 can be adjusted independently of one another. In an embodiment, the individual cords may be adjusted either proximally of the first anchor 112, i.e. before entering the first anchor, or distally of the second anchor 114, i.e. after exiting the second anchor, or both. To that end, in an embodiment, a locking member 604 may be disposed either adjacent to the first anchor, the second anchor, as described above, or both. To adjust the cords in such embodiments, the locking member may be deactivated, each individual cord 118 may be tightened or loosened as desired, and, when the desired restraining matrix support is achieved, the locking member may be activated to maintain the individual cords 118 in position. It will be understood that the restraining cords 118 may be fixated or maintained using any other device instead of or in addition to a locking member. In addition, it should be mentioned that the locking member may be any locking member known in the art.

In an embodiment, the individual cords 118 may be made of any suitable biocompatible material. Depending on whether a tissue to be restrained by the instant device requires a permanent or only a temporary support, the cord may be made of a bioresorbable or non-bioresorbable material. Suitable non-bioresorbable materials include, but are not limited to, polytetrafluoroethylene (PTFE), nylon, and polypropylene, among many others. Suitable bioresorbable materials include, but are not limited to polyglycolic acid, polylactic acid, and polydioxanone, among many others.

Figure 7A:
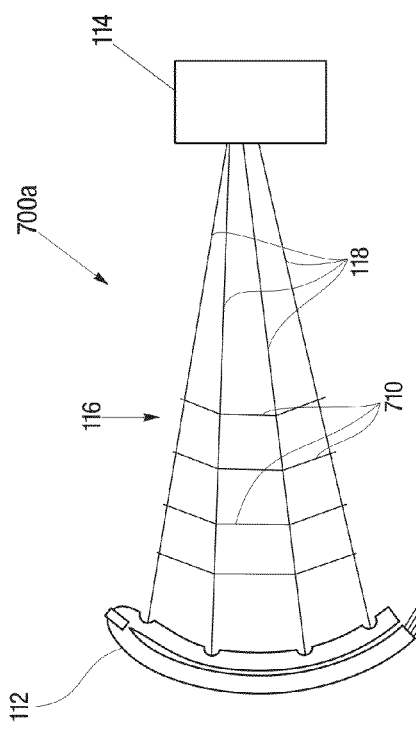
FIG. 7A and FIG. 7B illustrate embodiments of a restraining matrix suitable for use in tissue restraining devices of the present disclosure.
Figure 7B:
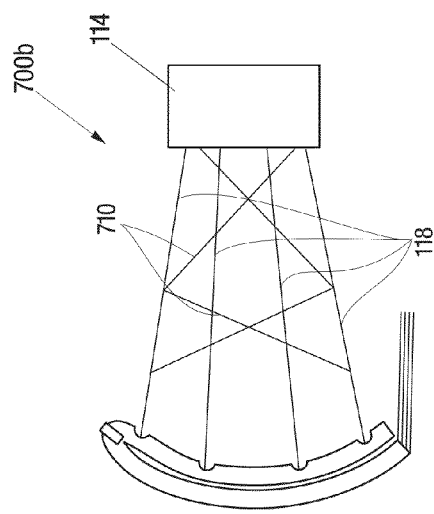

In reference to FIGS. 7A and 7B, in an embodiment, in addition to a plurality of restraining cords 118 extending substantially longitudinally between the anchors 112, 114, the restraining matrix 116 may also include cross-restraint members 710, which extend transversely between individual cords of the plurality of restraining cords 118. In an embodiment, the cross-restraint members 710 may run parallel to one another, as shown in FIG. 7A. In an embodiment, the cross-restraint members 710 may criss-cross one another, as shown in FIG. 7B. In an embodiment, some cross-restraint members may run parallel to one another, while others criss-cross other cross-restraint members.

The restraining matrix 116 in embodiment can have any geometric shape or pattern. In general, the shape or pattern of the matrix may depend on the shape of a tissue to be restrained. In an embodiment, the shape of the restraining matrix may be selected so the restraining matrix provides sufficient support to a prolapsing region to be restrained. The shape or pattern of the matrix may at least in part be dictated by the shapes of the first anchor and/or the second anchor. In an embodiment, the design of the first anchor, the second anchor, or both may be selected in such a manner as to ensure that the restraining system extends over the entire prolapsing region to be restrained.

Figure 8:
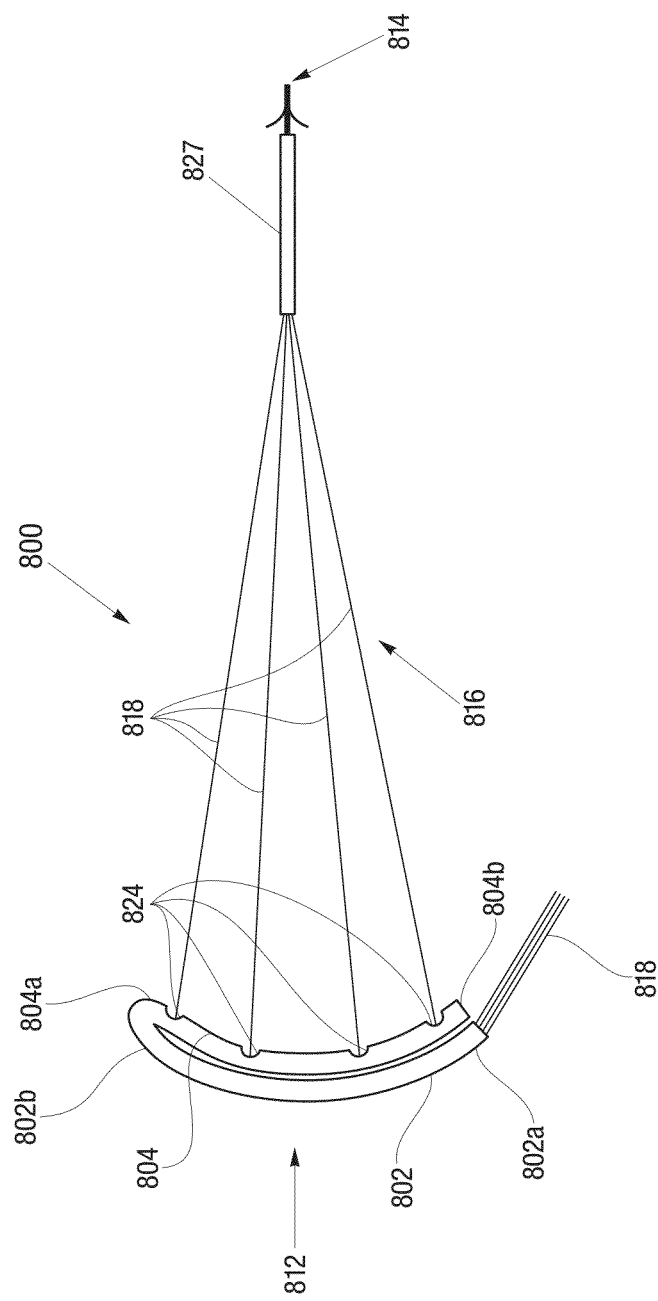
FIG. 8 illustrates an embodiment of a tissue restraining device of the present disclosure.

By way of a non-limiting example, FIG. 8. illustrates a tissue restraining device 800 suitable for restraining a prolapse in a heart valve having a generally circular shape. The tissue restraining device 800 includes a first anchor 812, a second anchor 814, and a restraining matrix 816. The first anchor 812 may have a generally elongated shape with inwardly curved ends and the second anchor 814 may have an apical end at which the individual cords may be collected together, thus forming a substantially triangular restraining matrix. In general, the first anchor 812, the second anchor 814, and the restraining matrix 816 may have features described above in relation to various embodiments of the first anchor 112, second anchor 114 and restraining matrix 116. In the particular embodiment shown in FIG. 8, the first anchor 812 comprises a first arm 802 and a second arm 804, however, the first anchor 812 may only include a single arm or more than two arms. Moreover, although not shown in FIG. 8, each arm may comprises multiple sub-arms as described above and may have different shapes. In an embodiment, the first arm 802 and the second arm 804 may each have one or more inner lumens through which a guidewire, restraining cords or both can be passed.

To form the restraining matrix 816, a plurality of restraining cords 818 can extend between the first anchor 812 and the second anchor 814. In an embodiment, the restraining cords 818 can connect to the first anchor 812 at the plurality of contact points, as described above. In an embodiment, the plurality of restraining cords 818 can be directed through a one or more lumens (not shown) of the first arm 802, through one or more inner lumens of the second arm 804 and out of the second arm 804 through the plurality of openings 824. In an embodiment, the one or more inner lumens of the first arm 802 and the one or more inner lumens of the second arm 804 may be in communication with one another, that is, the plurality of restraining cords can pass from one arm to the other arm without exiting the device 800. In an embodiment, the inner lumens of the first arm 802 the inner lumens of the second arm 804 may not be in communication with one another, and thus, an exit or openings may be provided at or near the second end 802*b* of the first arm 802 and at or near the first end 804*b* of the second arm 804, respectively to permit passing of the cords 818 from one arm to the other. Of course, one or more exit openings may still be provided even when the inner lumens of the entrance and exit arms are in direct communication with one another.

The plurality of restraining cords 818 may be separated inside the one or more inner lumens of the second arm 804 to exit the second arm 804 through the plurality of openings 824. The individual cords of the plurality of restraining cords 818 may extend for a distance forming the restraining matrix 816 until they can be collected into a bundle 827 before passing through the second anchor 814. The number of individual cords forming the matrix and the distance between individual cords may vary as long as the matrix provides adequate support to a mitral valve in need of repair. By way of a non-limiting example, the standard teaching in mitral valve repair is that the free margin of a leaflet must be supported by a good quality cord (i.e., one that is not elongated or too thin) at least every 5-7 millimeters along the leaflet. Using this guideline, the individual cords may be preferably spaced at a similar interval or slightly wider. In an embodiment, the individual cords may be evenly spaced. In an embodiment, the individual cords may be spaced unevenly or may have varying thickness to accommodate varying prolapsing forces.

Figure 9:
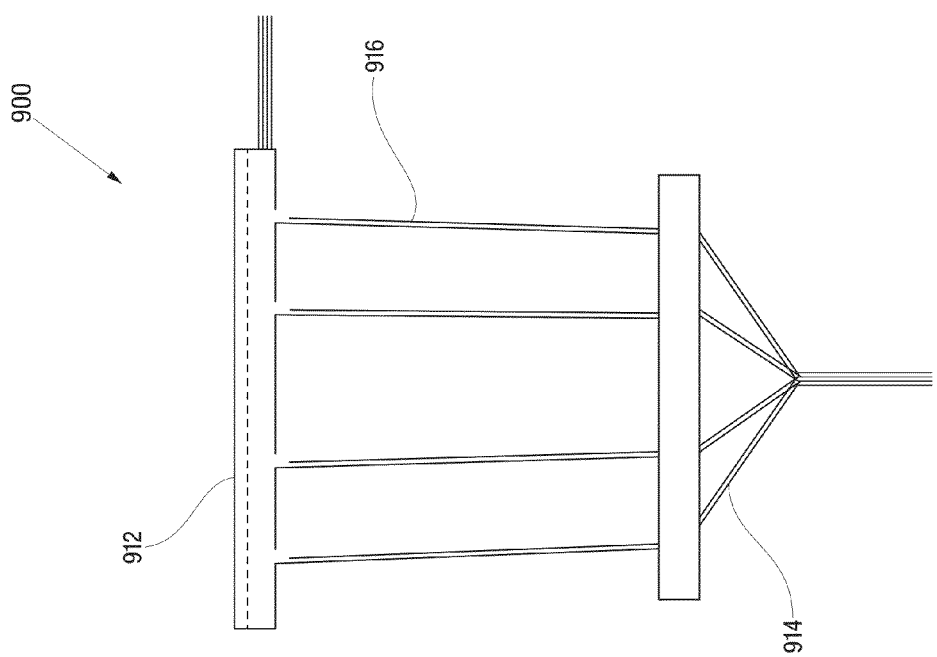
FIG. 9 illustrates an embodiment of a tissue restraining device of the present disclosure.

By way of a non-limiting example, FIG. 9. illustrates a tissue restraining device 900 suitable for restraining a prolapsed tissue having a generally elongated shape. The tissue restraining device 900 includes a first anchor 912, a second anchor 914, and a restraining matrix 916. The first anchor 912, the second anchor 914, and the restraining matrix 916 may have features described above in relation to various embodiments of the first anchor 112, second anchor 114 and restraining matrix 116. As shown in FIG. 9, both the first anchor 912 and the second anchor 914 may have a generally elongated shape, thus forming a substantially rectangular restraining matrix. It will be understood that by the shape of the restraining matrix can be customized to fit a particular application by changing the size and shape of the first anchor, the second anchor or both.

Figure 32:
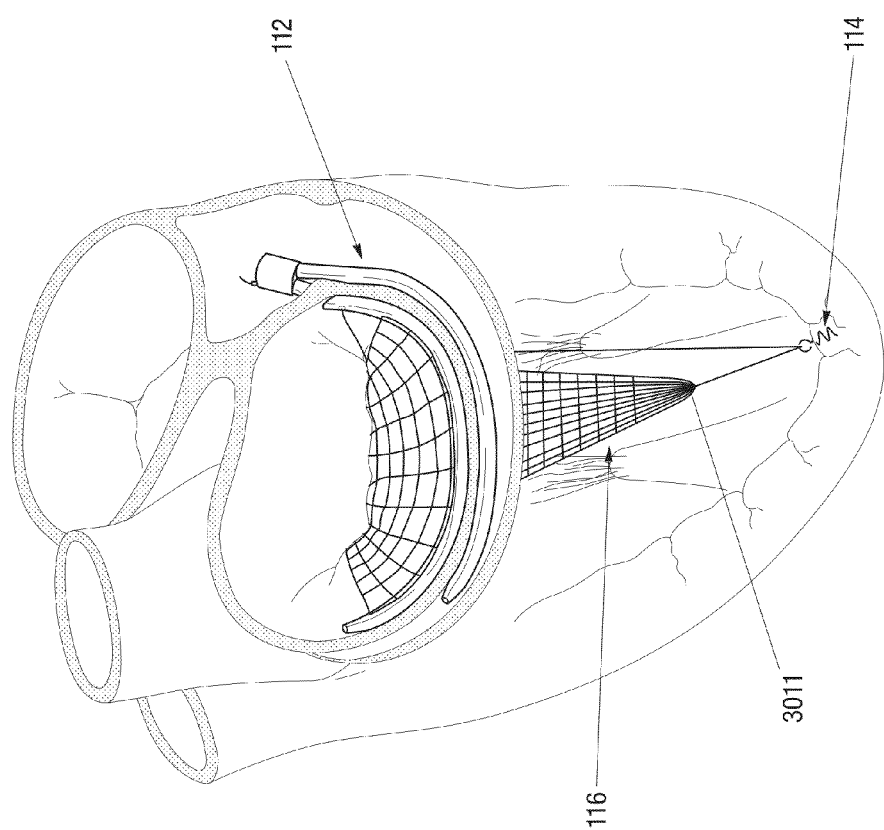
FIG. 32 illustrates an embodiment of a tissue restraining device of the present disclosure.

FIG. 30, FIG. 31 and FIG. 32 demonstrate another embodiment of a restraining matrix 116 having a substantially triangular shape. In an embodiment, the individual restraining cords 118 may come together at an apex 3011 of the restraining matrix 116 and a strand 3013 may extend distally from the apex 3011 toward the second anchor 114. In such an embodiment, the tension of the restraining matrix 116 may be adjusted by pulling on the strand 3013. In an embodiment, the individual restraining cords 118 may be adjustable at or proximally of the first annuloplasty member 3000. In an embodiment, the individual restraining cords 118 may be fixed to the annuloplasty member, such that the tension of the restraining matrix 116 as a single unit may be adjusted by pulling on the strand 3013. It should of course be understood that although the restraining matrix 116 is illustrated having individual cords 118 joined at the apex 3011, any other designs may be possible, so long as a the individual cords can be connected for ease of handling during operation.

In an embodiment, the second anchor 114 may be provided with a loop 3012 to allow the strand 3013 to be passed through the loop before the strand 3013 may return to the first anchor 112. In an embodiment, the strand 3013 may be passed between the leaflets of the valve 3005 and may be joined to the annuloplasty member 3000. The strand 3013 may be joined to the annuloplasty member 3000 anywhere along the posterior section 3004, including, but not limited to, either end of the posterior section 3004 near a commissar or in the middle of the posterior section 3004. In an embodiment, the strand 3013 may be passed through the annuloplasty member 3000. In such an embodiment, the tension of the restraining matrix 116 may be adjusted by pulling on the strand 3013. In an embodiment, another strand 3015 may be fixedly disposed on the annuloplasty member 3000 so that the strands 3013, 3015 can be joined to maintain a desired tension in the restraining matrix 116, as shown in FIG. 31. Additionally or alternatively, in embodiments where the individual restraining cords 118 are adjustable at the first anchor 112, the strand 3013 can be joined to the proximal ends of one or more restraining cords 118. The strands and/or cords can be joined together with a knot or by another conventional techniques, such as gluing, welding, melting, or similar. It will of course be understood that other means for tightening the restraining matrix 116 besides with the strand 3013 may be provided. Similarly, other designs that can allow attachment of the strand 3013 or apex 3011 to the second anchor 112 are also contemplated. By way of a non-limiting example, the restraining matrix 116 may be provided with a chain of loops extending from the apex 3011 and the second anchor 114 may be provided with a hook, such that the chain of loop can be pulled toward the second anchor 114 to tighten the restraining matrix 116 and a loop of the chain of loops may be hooked into the second anchor 114 to maintain tautness of the restraining matrix 116. In an embodiment, distal ends of the restraining cords may be passed through the loop of the second anchor 114, instead of a single strand, as described above. In an embodiment, the distal ends of the restraining cords 118 may be fixed at the second anchor, such that the restraining matrix 116 may be performed by adjusting the restraining cords 118 at or proximally of the first anchor. Finally, it should be understood that although this embodiment of the restraining matrix 116 is described in connection with the device 100 having the annuloplasty member 3000, this embodiment of the restraining matrix 116 another type of the first anchor 112, such as for example, a hairpin-shaped first anchor 112, as shown in FIG. 32.

Figure 10A:
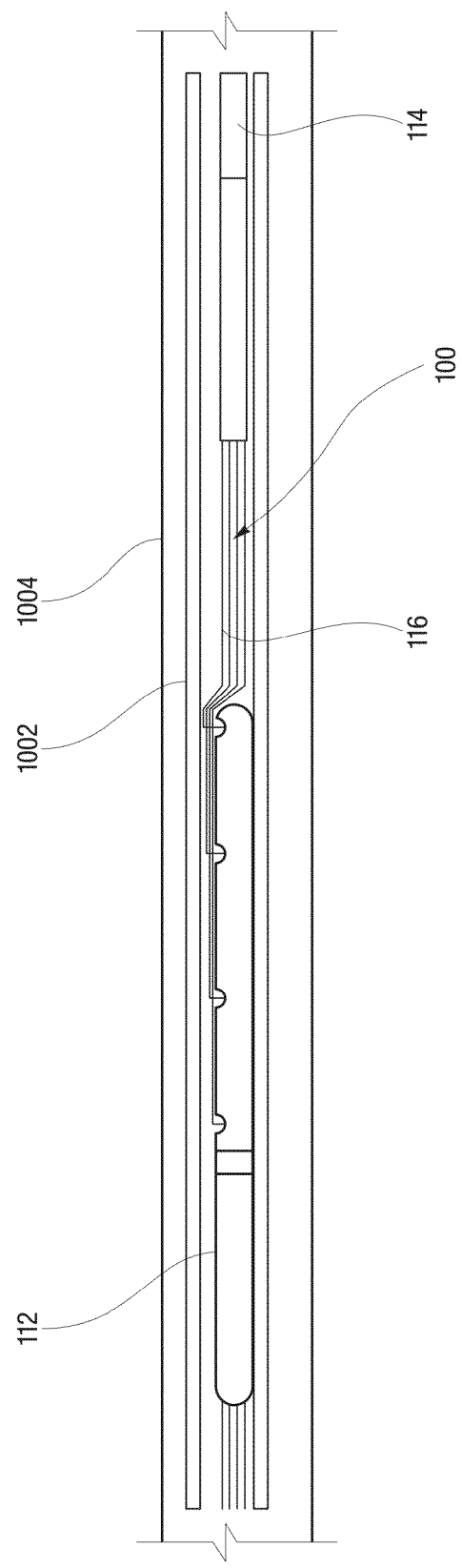
FIG. 10A illustrates an embodiment of a tissue restraining device of the present disclosure loaded into a sheath of a delivery catheter for delivery to implantation site.

In operation, as mentioned above, tissue restraining devices of the present disclosure may be suitable for restraining various tissues. In reference to FIG. 10A, a suitable embodiment of a tissue restraining device 100 of the present disclosure may be loaded into a sheath 1002 of a delivery catheter for delivery through a guide catheter 1004 to a tissue to be restrained. As shown in FIG. 10A, in an embodiment, the entire tissue restraining device 100, including the first anchor 112, the second anchor 114, and the restraining matrix 116, can be loaded into the sheath 1002. However, to the extent desired, only a portion of the tissue restraining device 100 may be loaded into the sheath 1002. When one or both of the anchors of the device 100 are secured in the proximity of a tissue to be restrained, the sheath 1002 can be retracted to deploy the device 100. The restraining matrix 116 of the device 100 can be positioned to drape over a tissue in need of support. In an embodiment where the restraining cords forming the matrix are individually adjustable, the restraining cords 118 of the device 100 may be adjusted until all prolapsing segments of the tissue in need of support are corrected. Once the individual cords 118 have been adjusted, the individual cords 118 can be locked in position.

Figure 10B:
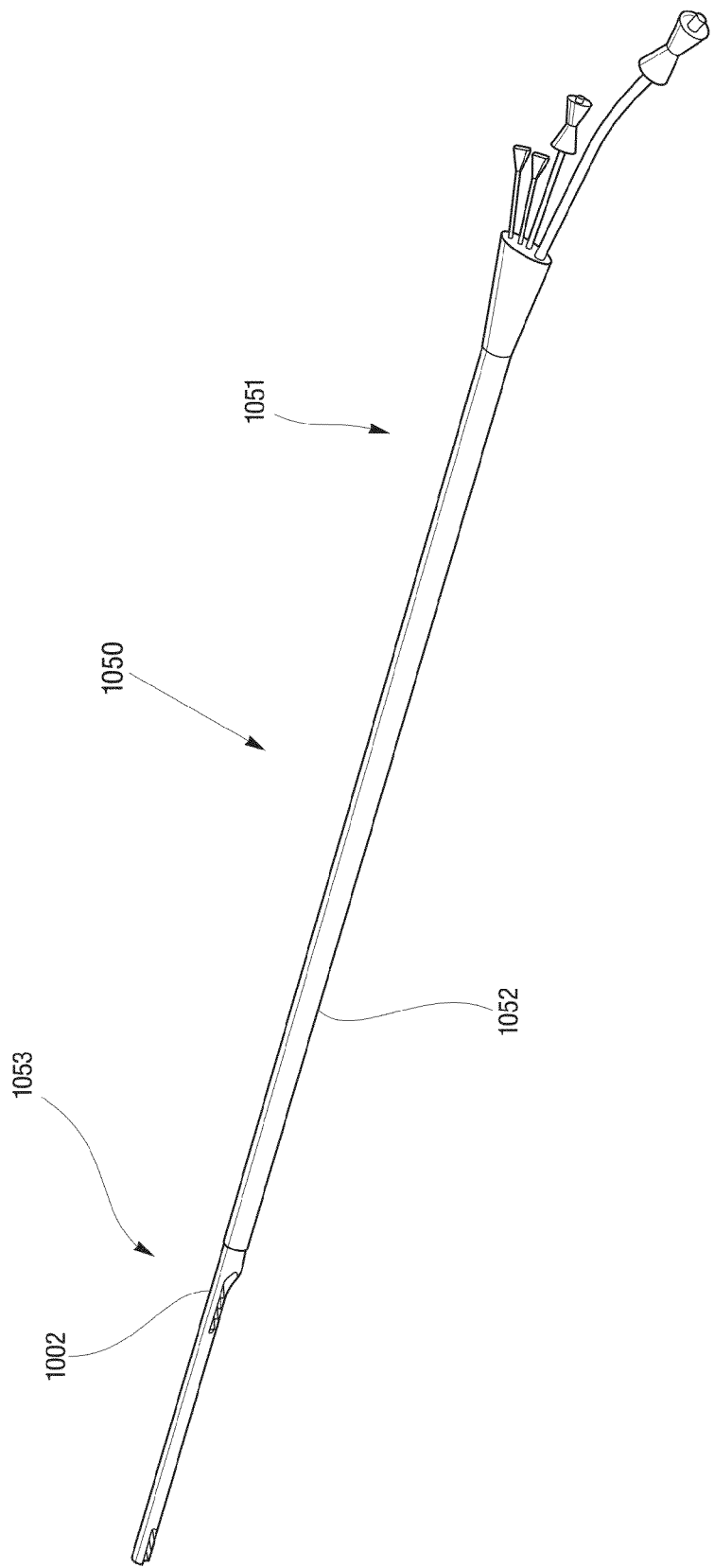
FIGS. 10B-10D illustrate an embodiment delivery catheter for delivering a tissue restraining device of the present disclosure to implantation site.

FIG. 10B demonstrates an embodiment delivery catheter 1050. In an embodiment, the delivery catheter 1050 may include an outer sheath 1052, which forms a proximal portion 1051 of the delivery catheter 1050. The delivery catheter 1050 may also include an inner sheath 1002, which extends out of the outer sheath 1052 to form a distal portion 1053 of the delivery catheter 1050. The inner sheath 1002 may be slidably disposed within the outer sheath 1052. The inner sheath 1002 may be designed to house a device to be delivered with the delivery catheter 1050.

Figure 10D:
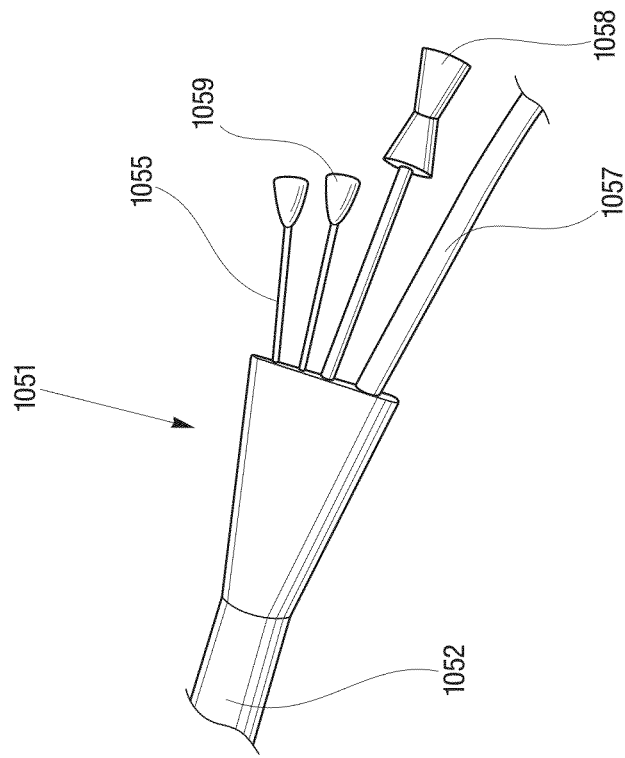

Referring to FIG. 10D, in an embodiment, the guide catheter 1050 may include multiple inner lumens. In an embodiment, one or more guidewires can be passed through the inner lumens of the delivery catheter 1050. Further, a number of tools for controlling the inner sheath 1002 and the device housed in the inner sheath 1002 can be passed though the inner lumens of the delivery catheter 1050. In an embodiment, the delivery catheter 1050 is provided with an inner sheath tether 1055 for sliding the inner sheath 1002 in relation to the outer sheath 1052.

Figure 10C:
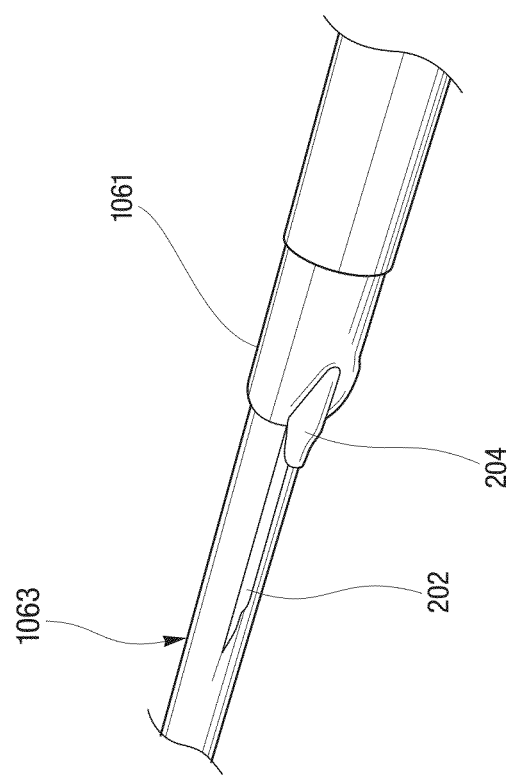

By way of a non-limiting example, the delivery catheter 1050 may be used to deliver the tissue restraining device 100 of the present disclosure. The tissue restraining device 100 may be loaded into the inner sheath 1002 for delivery to the site of interest. Referring to FIG. 10C, the inner sheath 1002 may include a wider base region 1061 in which the first anchor 112 can be housed and an elongated distal region 1063 which can house the second anchor 114. In an embodiment, the inner sheath 1002 may be split, as shown in FIG. 10C, to facilitate the delivery of an embodiment of the first anchor 112 with two arms 202, 204.

Referring again to FIG. 10D, in an embodiment, to control the tissue restraining device 100, the delivery catheter 1050 can be provided with a first anchor pushrod 1057 for advancing the first anchor 112 out of the inner sheath 1002, a second anchor pushrod 1058 for advancing the second anchor 114 from the inner sheath 1002, an restraining matrix tether 1059 for adjusting the restraining matrix 116, and combinations thereof. It should be noted that in an embodiment some of the control tools 1057, 1058 and 1059 may be adapted to serve multiple functions.

In an embodiment, tissue restraining devices of the present disclosure may be employed to restrict a mitral heart valve 1100, as shown in FIGS. 11A-11K. A guide wire 1102 may be advanced into coronary sinus (CS) vein 1104 to a target entry point 1106 into the left atrium. A guide catheter 1108 may be advanced over the guide wire 1102 and positioned with its tip aiming at the target entry point. Suitable embodiments of guide catheters include, but are not limited to, embodiments presented in FIGS. 12A-12F. FIGS. 12A-12B illustrates a delivery catheter with a right angle distal tip 1210. FIGS. 12C-12D illustrate an embodiment of a delivery catheter with right angle distal tip 1225 and a centering balloon 1220. FIG. 12E-12F illustrate an embodiment of a delivery catheter with lasso distal tip 1230. Next, access may be gained to the left atrium 1110 from CS, and the guide wire 1102 and then the guide catheter 1108 may be advanced into the left ventricle 1110. An embodiment of a restraining device 100 of the present disclosure, such as, by way of a non-limiting example, the device 800 presented in FIG. 8, may be advanced inside a sheath, as discussed above, through the guide catheter 1108 into the deployment position. The second anchor 114 of the device 100 may be removed from the guide catheter 1108 and may be anchored in the left ventricle 1110. The guide catheter 1108 may then be removed and the sheath may be retracted to deploy the restraining device 100.

Figure 3:
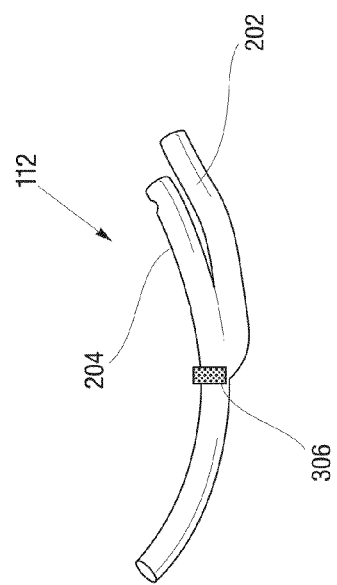
FIG. 3 illustrates an embodiment of an anchor suitable for use in tissue restraining devices of the present disclosure.
Figure 13B:
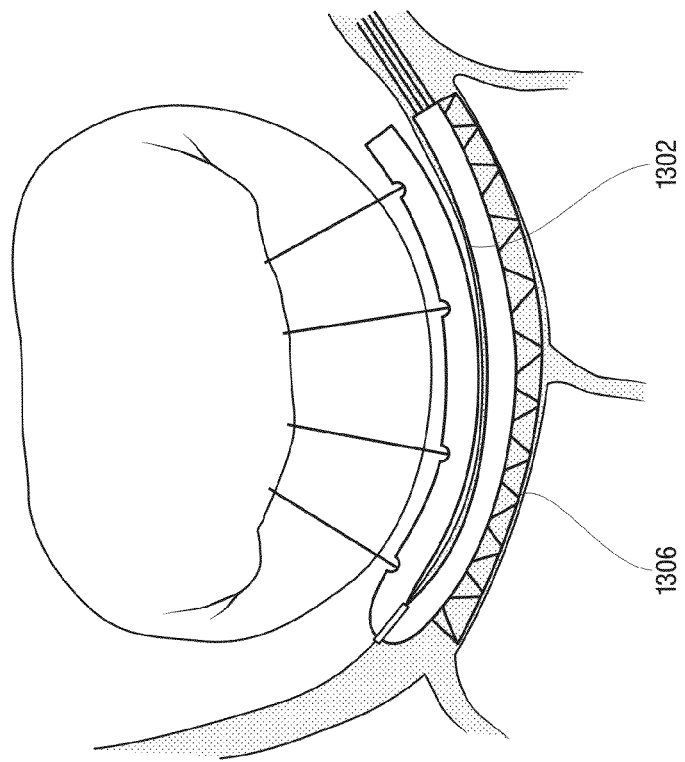
FIG. 13A and FIG. 13B illustrate various embodiments of a tissue restraining device of the present disclosure.
Figure 13A:
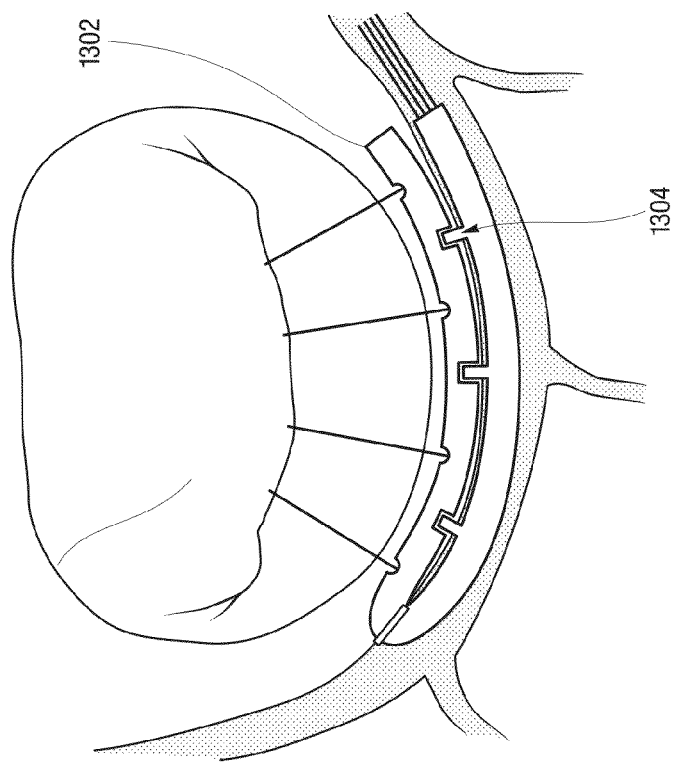
Figure 14:
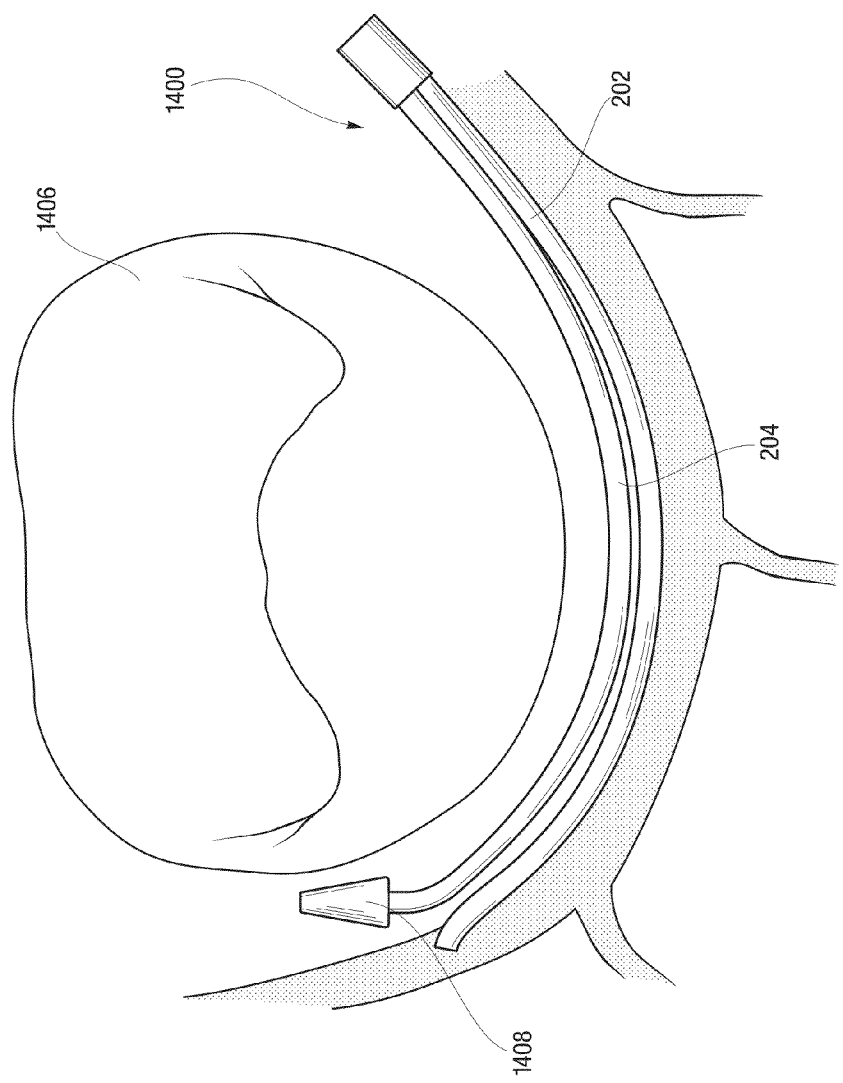
FIG. 14 illustrates an embodiment of a tissue restraining device of the present disclosure.
Figure 15A:
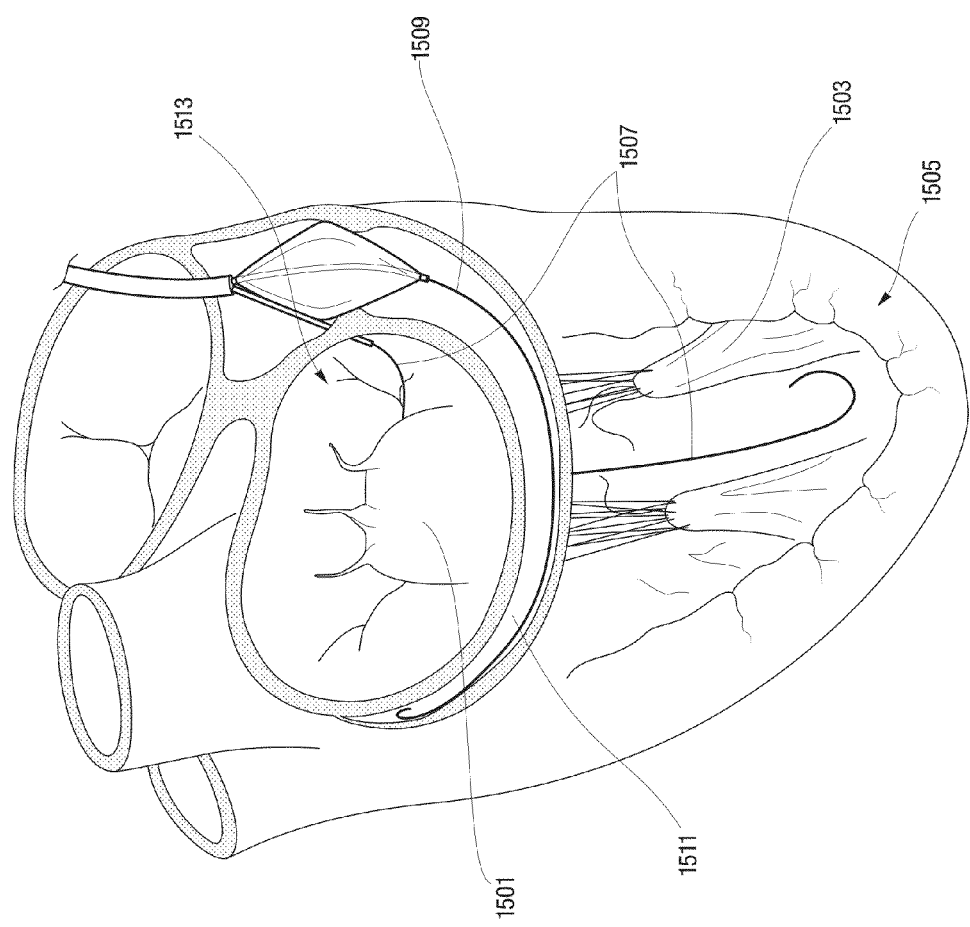
FIGS. 15A-15G illustrate a method for mitral valve repair using a tissue restraining device of the present disclosure.
Figure 15C:
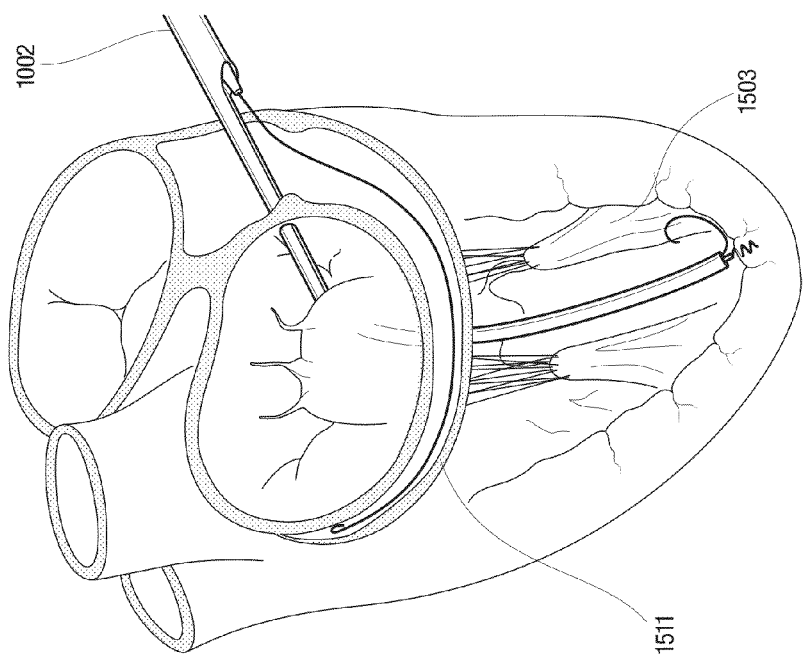
Figure 15B:
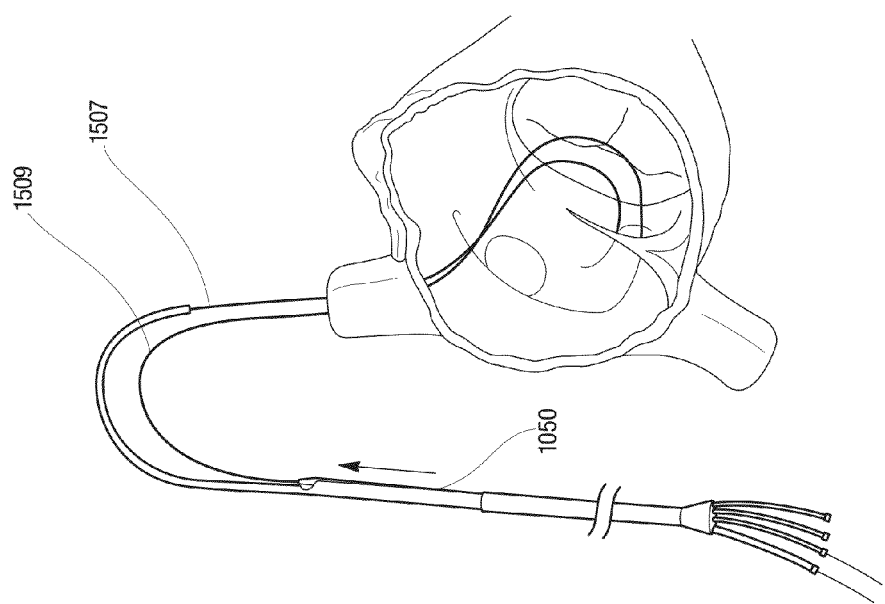
Figure 15E:
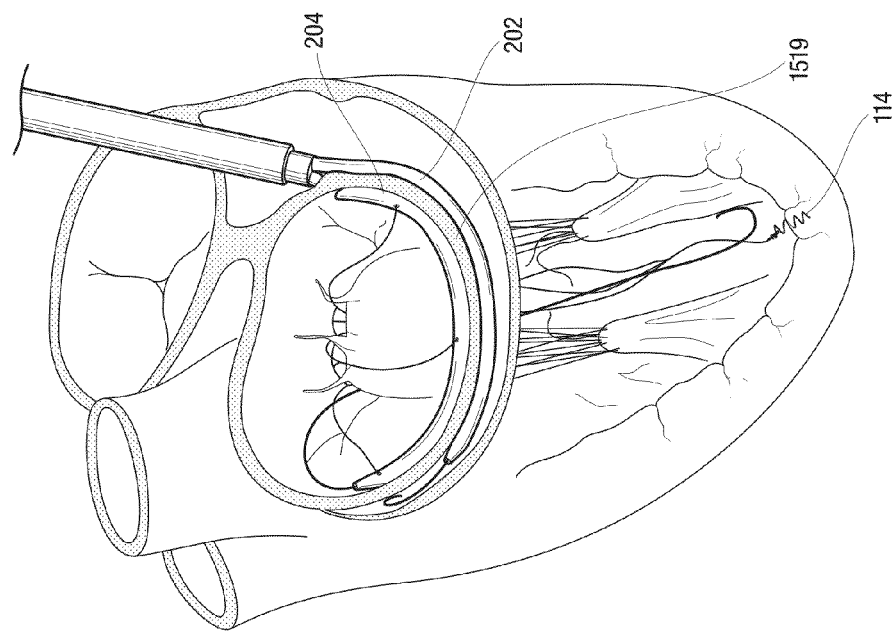
Figure 15D:
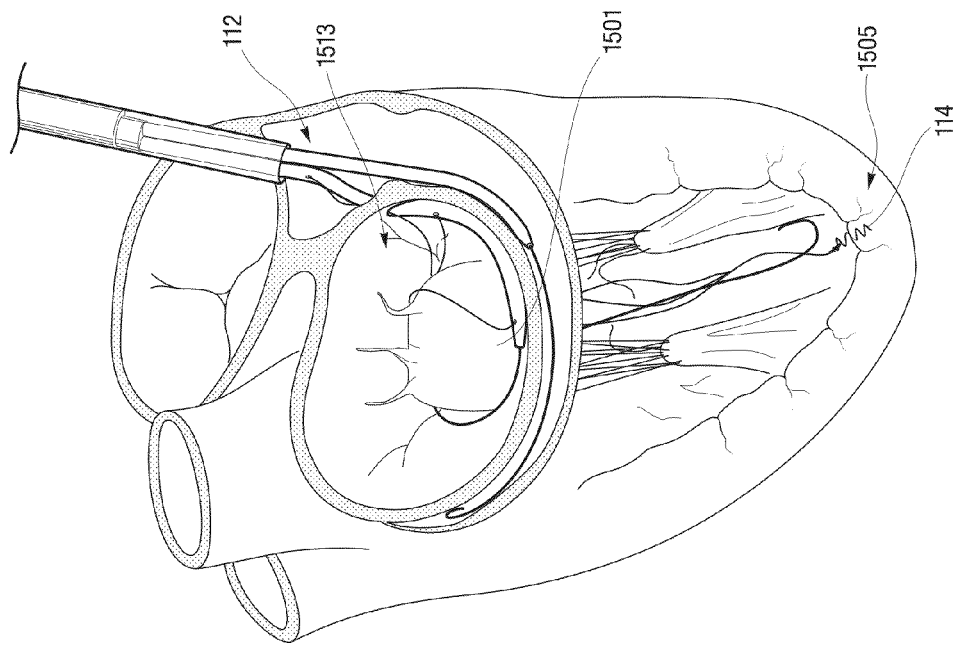
Figure 15G:
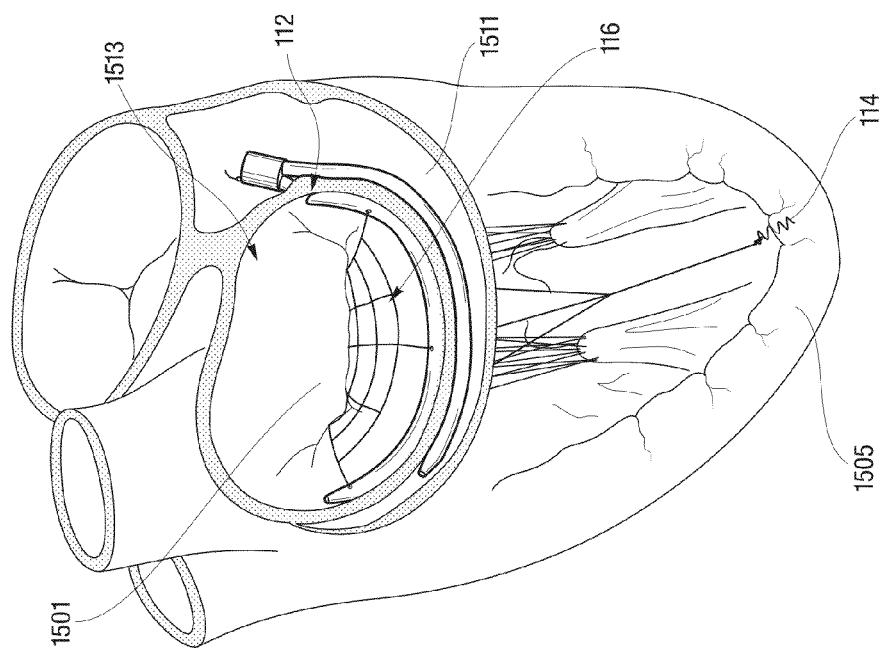
Figure 15F:
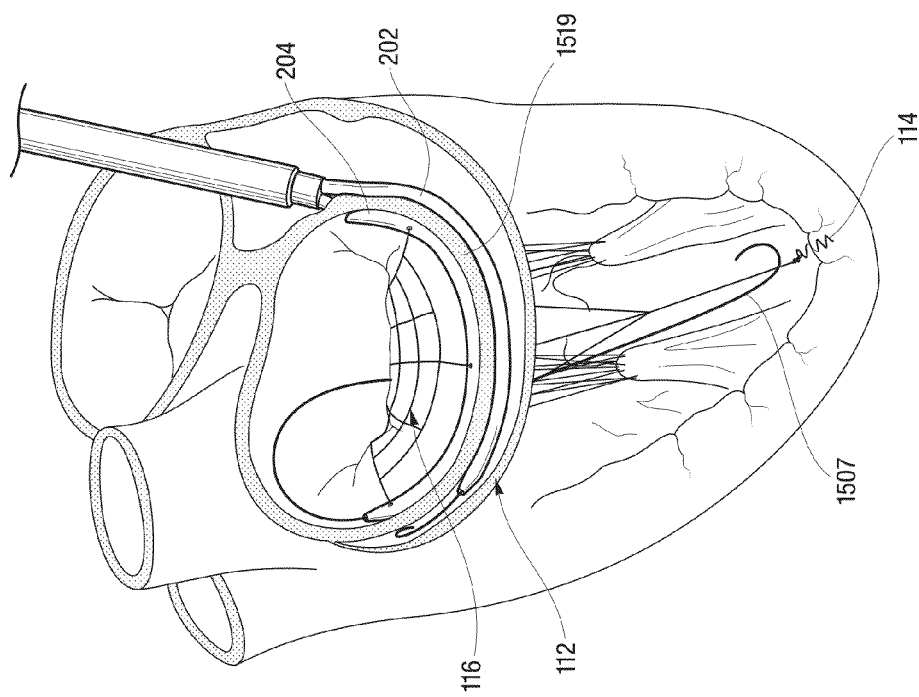

In embodiments where the first anchor 112 includes a first arm 202 and a second arm 204, such as for example shown in FIG. 2, 3, or 4, the tissue restraining device 100 may be deployed with its first arm in CS and its second arm 204 in the left atrium. The arms cooperate together to pinch the common wall between the CS and left atrium, thus securing the first anchor 112 of the tissue restraining device 100 in place adjacent to the mitral valve. Additionally or alternatively, to further secure the deployed device 100 in place, anchoring pins 1304 or an anchoring stent 1306 may be employed, as shown in FIGS. 13A and 13B. In yet another embodiment, as shown in FIG. 14, the second arm 204 of the first anchor 112 may traverse a valve 1406 and extend up the side of the valve. The second arm 204 may include a member 1408, which can be designed to come into contact with the valve to, among other things, prevent, or at least minimize, sideway motion of the first anchor.

Figure 6B:
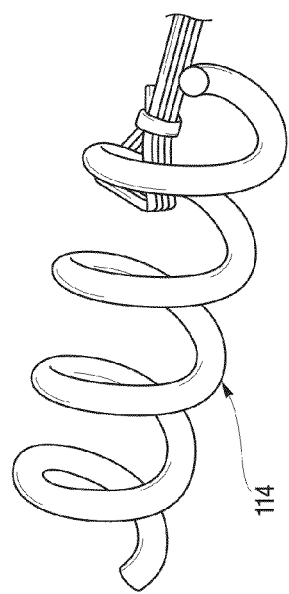

The restraining matrix 116 may be positioned to drape over the posterior leaflet of the mitral valve and may be adjusted until all prolapsing segments are corrected. Once the restraining matrix 116 has been adjusted, they can be fixated in position and, optionally, trimmed to remove extra material. For example, in an embodiment, the second anchor may be as shown in FIG. 6. In such embodiment, the individual cords may be bundled together before being pulled through the lumen in the second anchor using a suture snare. The individual cords 118 may be sufficiently long to ensure that the ends of the cords pass through the second anchor and remain outside the second anchor. Individual cords may be tightened or loosened by pulling on individual cords. When the desired support is achieved, the locking member may be activated to permanently secure the individual cords in position.

Figure 11L:
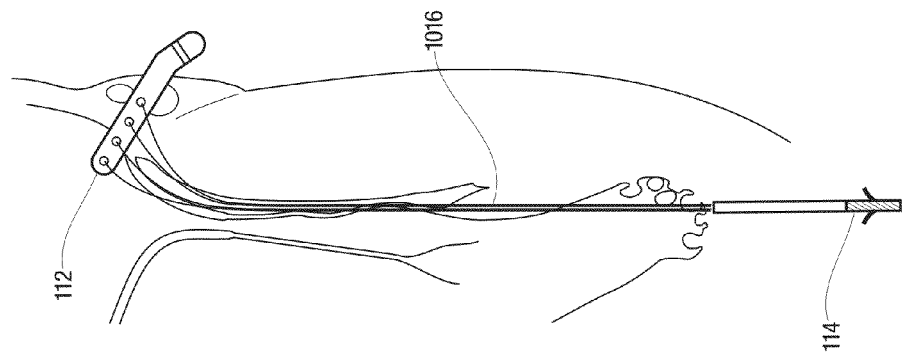
Figure 11K:
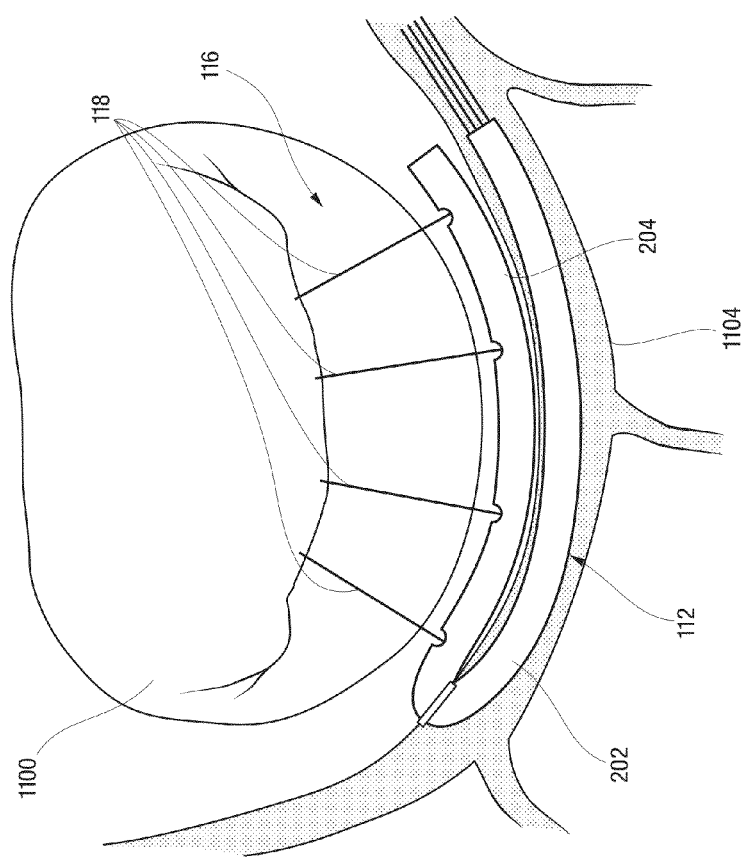
Figure 12E:
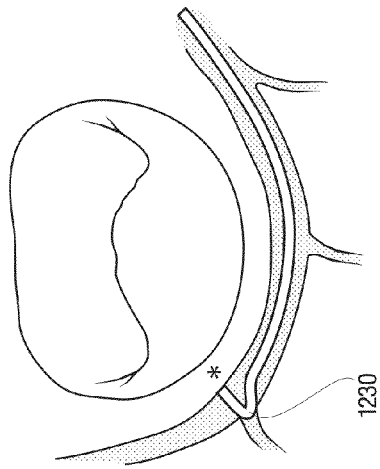
FIGS. 12A-12F illustrate various suitable embodiments of delivery catheters for delivering tissue restraining devices of the present disclosure.
Figure 12F:
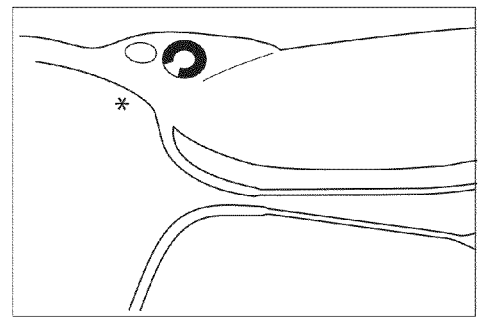
Figure 12C:
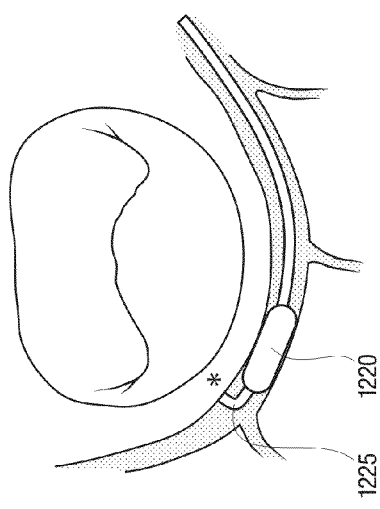
Figure 12D:
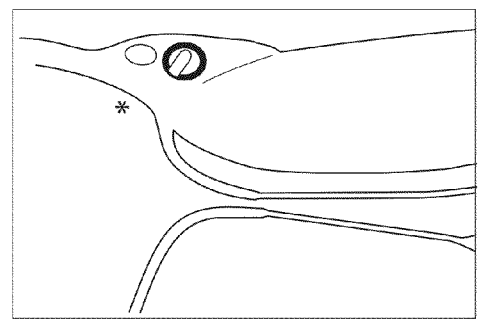
Figure 12A:
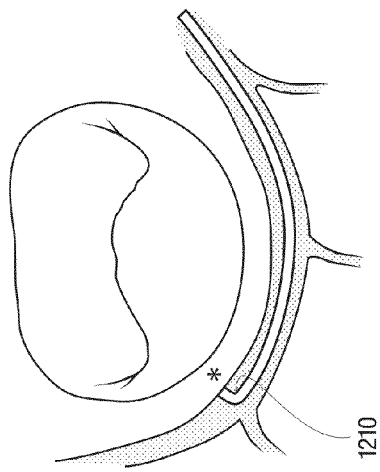
Figure 12B:
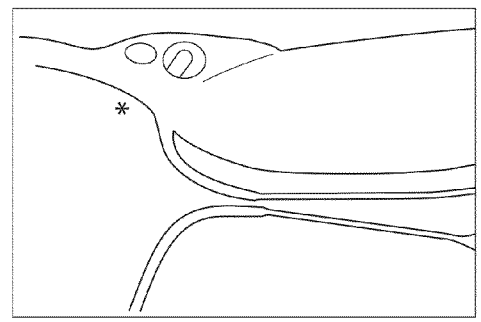

FIG. 11K illustrates an embodiment of the restraining device 100 in the deployed position. The device 100 includes the first anchor 112, comprising a first arm 202 deployed in CS and a second arm 204 deployed in the left atrium, a second anchor 114 secured inside the left ventricular, and restraining matrix 116 extending between the first anchor 112 and the second anchor 114 over the posterior leaflet of the mitral valve 1100. The retraining matrix 116 is formed by a plurality of restraining cords 118. In an embodiment, the restraining cords 118 can be adjustable to ensure that the restraining matrix provides adequate support to one or more prolapsing regions of the mitral valve 1100. In a further embodiment, the restraining cords 118 are individually adjustable.

Another embodiment of a method for restraining a prolapsing mitral valve using a tissue restraining device 100 of the present disclosure is shown in FIGS. 15A-15G. A guide wire 1509 may be advanced into coronary sinus (CS) to a point in proximity of the mitral valve 1501. Another guidewire 1507 may be advanced near the ostium of the coronary sinus, into the left atrium through the atrial septum and on to the left ventricle. For clarity, the guidewire 1507 can be referred herein as a transeptal guidewire 1507 and the guidewire 1509 can be referred to herein as a CS guidewire 1509. The second anchor 114 can then be advanced over the transeptal guidewire 1507 into the left ventricle 1503 and embedded into the left ventricle apex 1505. In an embodiment, the first anchor 112 may be advanced over both the transeptal guidewire 1507 and the CS guidewire 1509, where the transeptal guidewire may be inserted into the second arm 204 of the first anchor and the CS guidewire may be inserted into the first arm 202 of the first anchor 112. In this manner, once the first anchor 112 is fully deployed, the first arm 202 is located in the coronary sinus, while the second arm is located in the left atrium 1513. Because the first arm 202 and the second arm 204 are biased toward one another, the first arm 202 and the second arm 204 may pinch the common wall 1510 between the coronary sinus and the left atrium to securely attach the first anchor 112 in proximity of mitral valve 1501. In an embodiment, the point of connection of the arms 202, 204, such as, for example, the apex 206 or the hub 410, may be wedged at the coronary sinus ostium. Deployment of the first and second anchor in this manner causes the restraining matrix 116 to drape over the posterior leaflet of the mitral valve 1501. The restraining matrix 116 may be adjusted to ensure that the restraining matrix provides a desired support to prolapsing regions of the mitral valve 1501. Subsequently, the restraining cords 118 can be fixated and cut.

By way of non-limiting example, a delivery catheter 1050 may be used to deploy the restraining device 100 as shown in FIGS. 15A-15G. To that end, the delivery catheter 1050 may be advanced over the transeptal guidewire 1507 and the CS guidewire 1509 such that the distal region 1063 of the inner sheath 1002 is advanced into the left ventricle. At this point, the inner sheath 1002 may be retracted using the sheath tether and the second anchor 114 may be advanced with the second anchor pushrod 1058 until the second anchor 114 is embedded into the tissue of the left ventricle, for example, the left ventricle apex. Next, the inner sheath 1002 may be further withdrawn to initiate the deployment of the first anchor 112. The first anchor 112 may be advanced using the first anchor pushrod 1057 until the first anchor is fully deployed from the delivery catheter 1050. Once the first anchor 112 is in a desired position, the restraining matrix 116 may be adjusted using the restraining matrix tether 1059 until restraining matrix 116 provides a desired support to prolapsing regions of the mitral valve 1501. When the restraining matrix 116 has been adjusted, the restraining matrix tether 1059 can be cut and fixated. Lastly, the delivery catheter 1050 and the guidewires 1507, 1509 can be withdrawn.

FIG. 30 and FIG. 31 illustrate a non-limiting example of a method for restraining a prolapsing mitral valve with a tissue restraining device 100 having an annuloplasty member 3000 as the first anchor 112. In an embodiment, the tissue restraining device 100 may be delivered via an open heart approach through an incision in the patient's chest. Suitable approaches for implantation of the tissue restraining device 100 of the present disclosure include, but are not limited to, a full median sternotomy, or less invasive partial sternotomy and a right (or less frequently left) full, partial or "mini" thoracotomy. It should of course be understood that more or less invasive approaches can also be used. After the patient is connected to a heart-lung machine, cardiopulmonary bypass is initiated and, if desired, the heart is arrested, the mitral valve is exposed through an incision through the left atrium or using a transeptal approach following an incision in the right atrium.

Once good exposure of the mitral valve 3005 has been achieved, the annuloplasty member 3000 maybe implanted along the valve annulus 3007 by any implantation technique currently utilized for annuloplasty member implantation, including, but not limited to, interrupted mattress sutures, a continuous running suture, interrupted simple (non-mattress) sutures, specialized clips or staples. Next, the second anchor 112 may be passed through the valve into the left ventricle and attached to the apex using an appropriate instrument. In an embodiment where the distal end of the restraining matrix 116 is connected to the second anchor prior to implantation of the second anchor 114, this pulls the restraining matrix 116 into the left ventricle 3021 extending the restraining matrix 116 over the posterior leaflet of the mitral valve. The tension of the restraining matrix 116 may then be adjusted to provide a desired support to the prolapsing segments and fixed in place to maintain that tension. The valve 3005 can then be tested using conventional techniques such as pressurizing the left ventricle 3021 with saline and assessing for residual leakage and prolapse. Once the appropriate tension in the restraining matrix 116 has been achieved, the restraining matrix may be locked in place using one of the techniques described above. The procedure can then be completed according to conventional techniques.

In an embodiment, the tension of the restraining matrix 116 may be adjusted after the atrial incisions are closed, the heart is restarted and the patient has been weaned off the heart lung machine. The restraining matrix 116 may be left loose. The atrial incision may be closed with a running suture, while allowing the restraining matrix to be tensioned from outside the heart, such as, by extending the proximal ends of the restraining cords 118 or the strand 3013 and/3015 beyond the atrial incision. The atrial suture may then be tightened so it does not leak but not permanently tied. The heart may then be restarted and the patient weaned off the heart lung machine Once the heart is beating on it own, the tension of the restraining matrix 116 may be precisely adjusted with guidance by transesophageal echocardiogram or another medical imaging techniques until all excess leaflet motion is eliminated or reduced, a good surface coaptation between the valve leaflets is established, the mitral regurgitation is corrected or combination thereof. As described above, testing of the valve repair is typically performed prior to closing atriotomy incisions by injecting saline into the left ventricle until sufficient pressure develops to close the valve leaflets and assessing the coaptation of the leaflets and for any residual regurgitation. Although useful, this technique is limited by the fact that the heart is flaccid and so the anatomy and physiology of the valve leaflet motion is not physiologic. Instead, the tissue restraining device 100 allows adjustment of the leaflets to be performed under actual physiologic conditions, i.e. with the heart beating on its own, rather than under static conditions, which may result in a more accurate adjustment and improved outcome of the procedure. In particular, systolic anterior motion (SAM) may occur as a complication of repair of a prolapsing mitral valve, possibly due to different anatomic factors. The present technique allows the surgeon to watch how the leaflets of the mitral valve coaptat under actual physiologic conditions before adjusting the tension in the restraining matrix to achieve the right level of coaptation between the leaflets of the mitral valve, thus reducing postoperative risk of SAM. Once a satisfactory repair has been achieved, the restraining matrix 116 may be fixed to maintain the desired tension, such as by pulling on the restraining members 118 or strand 3013 extending beyond the suture line. In an embodiment, the restraining matrix 116 may be tightened by instruments passed through the united suture line, in addition or instead of extending the restraining members 118 or the strands 3013, 3015 beyond the suture line. Finally, the suture lines may be permanently tightened to close the atriotomy incisions, and the procedure can then be completed according to conventional techniques.

Referring to FIG. 30 and FIG. 31, by way of non-limiting example, the tissue restraining device 100 may be implanted and the restraining matrix 116 may be loosely formed over the posterior leaflet 3006 of the mitral valve 3005, as shown in FIG. 30. In this embodiment the tensioning strand 3013 and, if present, the fixed strand 3015 may be joined to the middle part of the posterior portion 3004 of the annuloplasty member 3000. The strands 3013, 3015 may be left loose and long to extend beyond the atrial incision, while the atrial incision is closed with a running suture. The strand(s) may thus be accessed now from outside the heart. The atrial suture may then be tightened over the strands so it does not leak but not permanently tied. The heart may then be restarted and the patient weaned off the heart lung machine Once the heart is beating on its own, and the restraining matrix 116 may be adjusted to achieve a desired repair of the mitral valve. The position of the restraining matrix may then be fixated, such as, for example, by tying together strands 3013, 3015 as shown in FIG. 31. Once the restraining matrix 116 is fixed, the suture line may be permanently tied and the procedure can then be completed according to conventional techniques.

Figure 16:
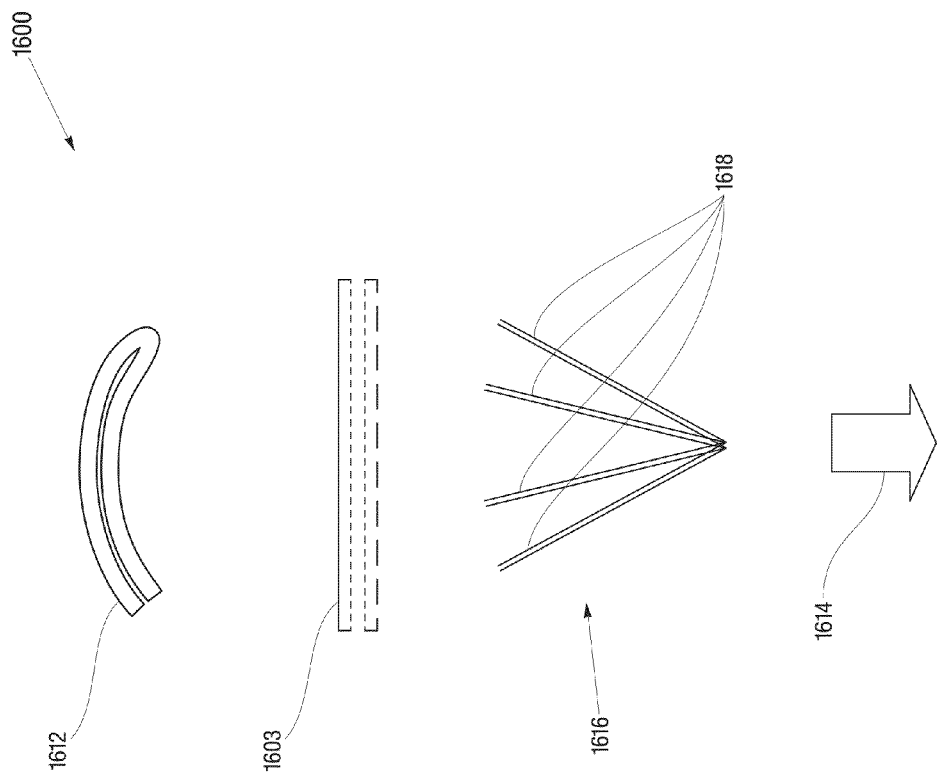
FIG. 16 illustrates an embodiment of a tissue restraining device of the present disclosure in a disassembled state.

Referring to FIG. 16, another embodiment of a tissue restraining device 1600 of the present disclosure is presented. The tissue restraining device 1600, shown here in the disassembled state, may generally include a first anchor 1612, a sheath 1603, and a restraining matrix 1616 and a second anchor 1614. In an embodiment, the restraining matrix may be formed by one or more restraining cords 1618. In an embodiment, the restraining matrix 1616 may be formed by a plurality of restraining cord 1618.

Figure 17A:
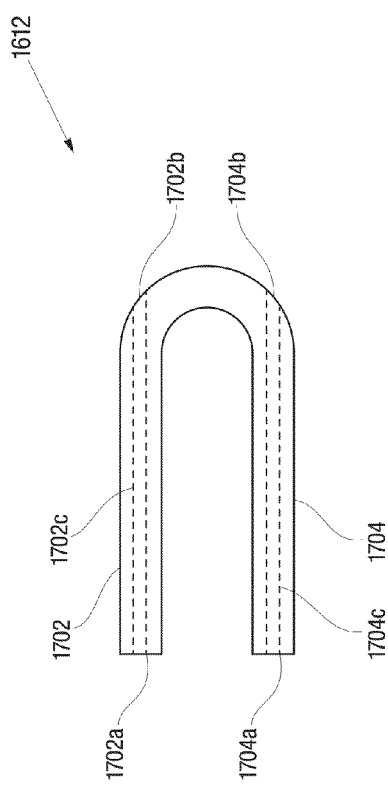
FIGS. 17A-17C illustrate embodiments of a first anchor of the tissue restraining device of the present disclosure.

Referring to FIG. 17A, the first anchor 1612 may, in an embodiment, be designed to attach to a common wall that separates the coronary sinus and the left atrium. To that end, in an embodiment, the first anchor may be U-shaped or hairpin-shaped, with a first arm 1702 configured for placement in the coronary sinus and a second arm 1704 configured for placement in the left atrium. For clarity purposes, the first arm 1702 may be referred to as the coronary sinus (CS) arm and the second arm 1704 may be referred to as the left atrium (LA) arm. The arms 1702 and 1704 may be biased toward one another to facilitate pinching of the common wall that separates the coronary sinus and the left atrium, to permit attachment of the first anchor 1612 thereto (i.e. in proximity to the mitral valve.)

Figure 17B:
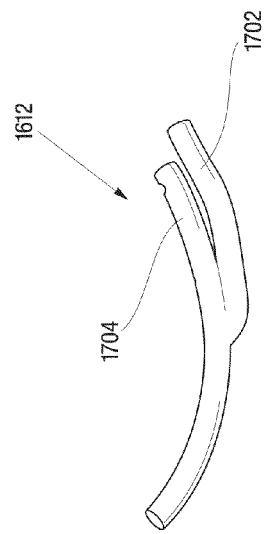
Figure 17C:
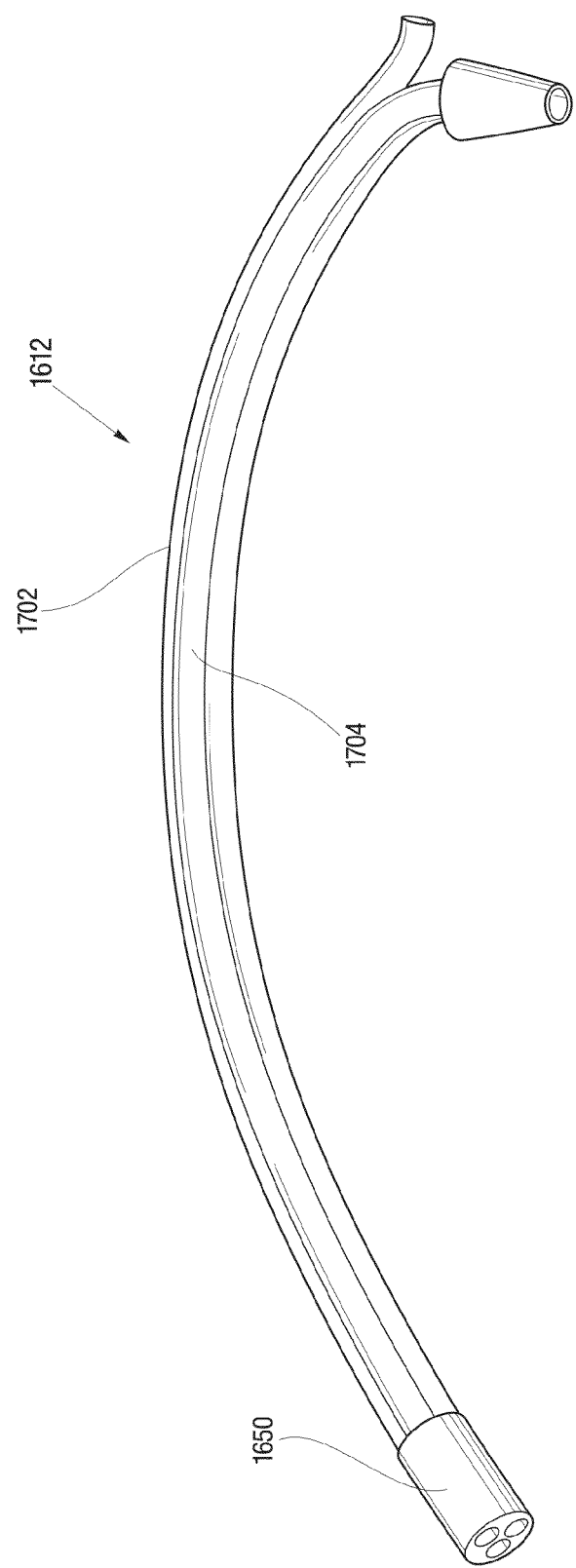

In an embodiment, the CS arm 1702 and the LA arm 1704 may have any length, independently of one another, as long as the arms 1702, 1704, in combination, enable a secure attachment of the first anchor 1612 to the common wall between the coronary sinus and the left atrium. Accordingly, although the arms 1702, 1704 are illustrated as having a similar length, the arms 1702, 1704 may have different lengths. The CS arm 1702 may be connected to the LA arm 1704 anywhere along the length of the LA arm 1704, and vice versa. In an embodiment, the arms 1702, 1704 are connected at their respective ends, as illustrated in FIG. 17A. In another embodiment of a first anchor 1701, the CS arm 1702 may be connected to the LA arm 1704 away from the end of the LA arm 1704, as illustrated in FIG. 17B. In yet another embodiment, shown in FIG. 17C, the arms 1702 and 1704 are connected by a hub 1750 designed to bias the arms 1702, 1704 toward one another.

Each of the arms 1702, 1704 may, in an embodiment, include one or more inner lumens extending through at least a portion of the arm. As will be described in more details below, the inner lumens of the first arm 1702 and the second arm 1704 may be sized to receive a guidewire therethrough. As illustrated in FIG. 17A, in an embodiment, the first arm 1702 may have a first opening 1702a and a second opening 1702b, and an inner lumen 1702c, extending between and in communication with the first opening 1702a and the second opening 1702b, such that a guidewire may be inserted through the inner lumen 1702. Similarly, the second arm 1704 may have a first opening 1704a and a second opening 1704b, and an inner lumen 1704c, extending between and in communication with the first opening 1704a and the second opening 1704b, such that a guidewire may be inserted through the inner lumen 1702c. The one or more guidewires inserted into one or both inner lumens 1702, 1704 of the first anchor 1612 may facilitate delivery of the first anchor 1612 to a deployment site and positioning of the first anchor at the deployment site.

Figure 18A:
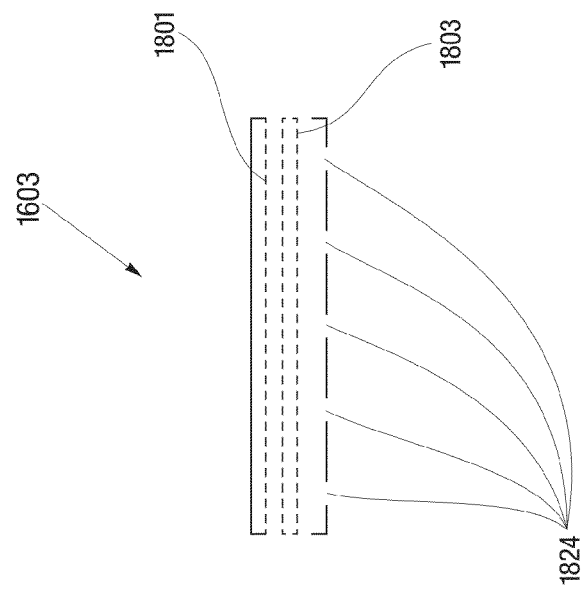
FIG. 18A and FIG. 18B illustrate embodiments of a sheath of the tissue restraining device of the present disclosure.
Figure 19:
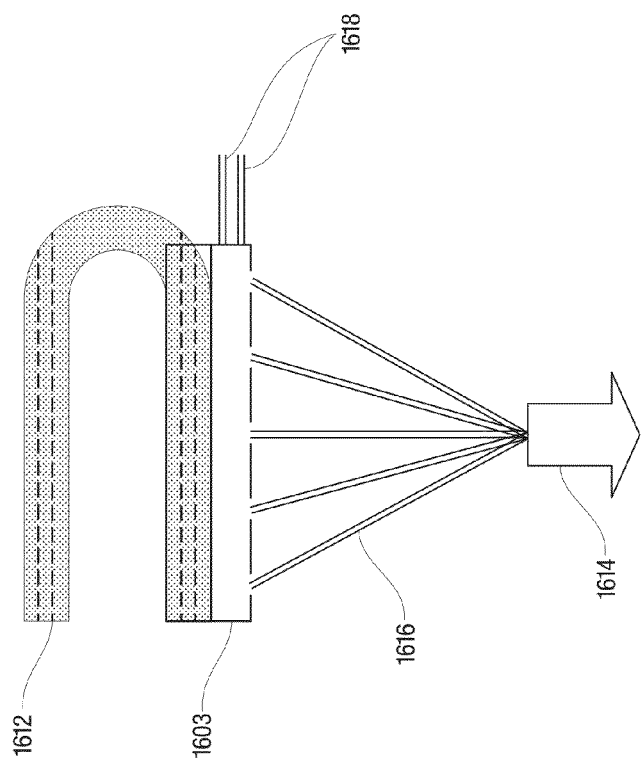
FIG. 19 illustrates an embodiment of a tissue restraining device of the present disclosure in an assembled state.

The tissue restraining device 1600 may further include a sheath 1603. The sheath 1603 may be designed to be coupled to the first anchor 1612. Referring now to FIG. 18A, in an embodiment, the sheath 1603 may include an interior lumen 1800, configured to receive the LA arm 1704 of the first anchor 1612. In this manner, the sheath 1603 may be pulled over the LA arm 1704 of the first anchor 1612, as shown in FIG. 19. In an embodiment, the interior lumen 1800 may be sized to receive a guidewire therethrough. Although FIG. 19 shows the sheath 1603 having a length similar to the length of the LA arm 1704 of the first anchor 1612, the sheath 1603 may be longer or shorter than the LA arm 1704. It should also be noted that the sheath 1603 may be coupled to the first anchor 1612 by any other conventionally used means, such as by sutures or an adhesive.

Figure 18B:
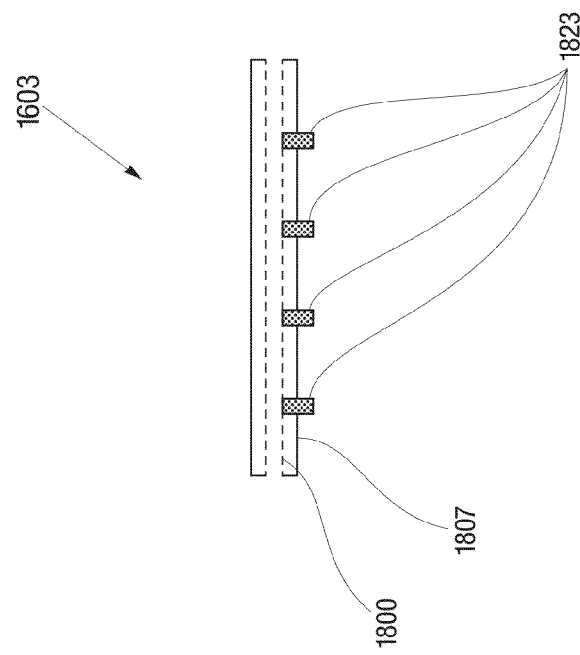

The sheath 1603 may further include one or more contact points 1803 positioned along at least a portion of the sheath 1603, as shown in FIG. 18A. The contact points 1803 are the points at which the restraining cords 1618 contact the sheath 1603. In an embodiment, the proximal ends of the restraining cords 1618 may be fixed to the sheath 1603 at the plurality of the contact points 1823, such as by adhesive, weld, or similar means. In an embodiment, as shown in FIG. 18B, the one or more contact points 1803 are one or more openings 1824 positioned along at least a portion of the sheath 1603, such that the restraining cords 1618 can be inserted into the sheath 1603 or can extend out from the sheath 1603. In an embodiment, the sheath 1603 includes a plurality of openings 1624. The openings 1824 may be designed to be in communication with the lumen 1800. The lumen 1800, in an embodiment, may be sufficiently designed such that the restraining cords 1618 can be directed along the lumen 1800 and out of the lumen 1800 through the plurality of openings 1824 to form the restraining matrix 1616.

Referring to FIG. 18B, in another embodiment, the sheath 1603 may include multiple lumens, such as a first lumen 1801 and a second lumen 1803. In the embodiment shown in FIG. 18B, the first lumen 1801 may, in an embodiment, be designed to accept a guidewire. The first lumen 1801 may also be configured to receive the LA arm 1704 of the first anchor 1612 therethrough, as is described above and illustrated in FIG. 19. The second lumen 1803 may, in an embodiment, include a plurality of openings 1824 positioned along a wall 1807 of the second lumen 1803 in spaced relation to one another, and in communication with the second lumen 1803. As is described in more detail below, the second lumen 1803 can be sufficiently designed such that the restraining cords 1618 can be directed along the second lumen 1803 and permitted to exit the second lumen 1803 through the plurality of openings 1824 to form the restraining matrix 1616. It should be noted that although the lumens 1801, 1803 are illustrated as having a similar length, the lumens 1801, 1803 may be of different lengths.

The tissue restraining device 1600 may further include a second anchor 1614. In an embodiment, the second anchor 1614 may be designed for placement, for example, within the left ventricle of a heart in a substantially opposing relation to the first anchor 1612. To this end, the second anchor 1614 provides a point to which the plurality of restraining cords 1618 can be attached in the left ventricle of a patient heart. A contemplated embodiment of the second anchor 1614 is shown in FIG. 6 of the instant disclosure.

The tissue restraining device 1600 may further include the restraining matrix 1616. Referring now to FIG. 19, when the tissue restraining device 1600 is assembled, in an embodiment, the restraining matrix 1616 may be formed by directing the plurality of restraining cords 1618 along a lumen of the sheath 1603 and out through the plurality of openings 1824. In an embodiment, each of the plurality of openings 1824 may accept a single cord 1618. Alternatively, should it be desired, each of the plurality of openings 1824 may accept multiple cords 1618. Each cord 1618, when exiting from the sheath 1603, may be directed toward the second anchor 1614, individually or as a bundle. The restraining matrix 1603 can have any geometric shape or pattern, depending on, for example, the shapes of the first anchor 1612 and the second anchor 1614. In an embodiment, the restraining matrix 1603 may be triangular or fan-shaped, as shown in FIG. 19.

In an embodiment, the restraining matrix 1616 can be adjustable by adjusting the restraining cords 1618 to provide a desired support to the prolapsing tissue. In an embodiment, individual cords 1618 can be adjusted independently of one another. In an embodiment, the individual cords may be adjusted either proximally of the first anchor 1612, i.e. before entering the first anchor, or distally of the second anchor 1614, i.e. after exiting the second anchor, or both. To that end, in an embodiment, a locking member may be disposed either adjacent to the first anchor, the second anchor, as described above, or both. To adjust the cords in such embodiments, the locking member may be deactivated, each individual cord 1618 may be tightened or loosened as desired, and, when the desired restraining matrix support is achieved, the locking member may be activated to fixate the individual cords 118 in position. It will be understood that the restraining cords 1618 may be fixated using any other device instead of or in addition to a locking member. In addition, it should be mentioned that the locking member may be any locking member known in the art.

Figure 20:
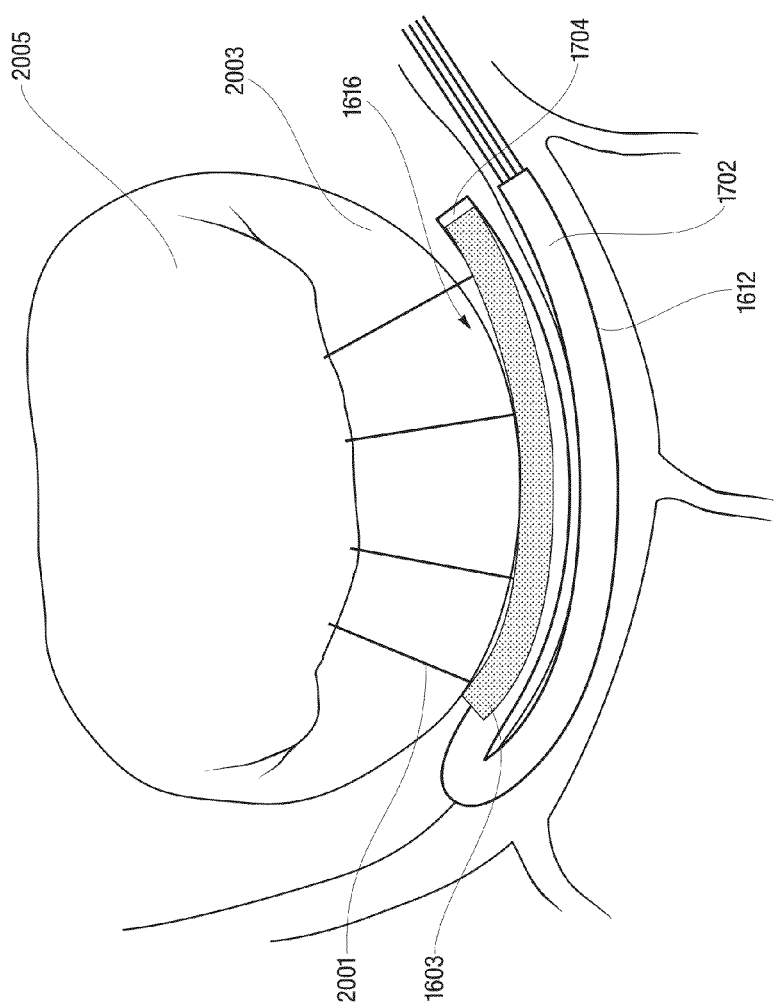
FIG. 20 illustrates an embodiment of a tissue restraining device of the present disclosure implanted adjacent to a mitral valve.

Referring to FIG. 20, the restraining matrix 1616 may be designed such that a proximal section 2001 of the restraining matrix 1616 extends along substantially the entire length of the posterior annulus 2003 of a mitral valve 2005. In another embodiment, the restraining matrix 1616 may be designed such that the proximal section 2001 may substantially drape over P1 (anterior or medial section), P2 (middle section), and P3 (posterior or lateral section) sections of the posterior leaflet 2005. In yet another embodiment, the restraining matrix may be designed such that the proximal section 2001 may drape over less than all three sections of the posterior leaflet 2005. To achieve that, the plurality of openings 1824 may be disposed over a length that enables the restraining matrix 1616 to provide a desired coverage of the mitral valve. For example, in an embodiment, the plurality of openings may be disposed along substantially the entire length of the posterior annulus 2003. In another embodiment, the plurality of openings 1824 may be disposed along a section of the posterior annulus 2003. Accordingly, in an embodiment, the sheath 1603, or at least a lumen with the plurality of openings in its wall, may extend along substantially the entire length of the posterior annulus 2003. In another embodiment, the sheath 1603, or at least a lumen with the plurality of openings 1824 in its wall, may extend along a section of the of the posterior annulus 2003. Alternatively or additionally, to provide the restraining matrix 1616 with a desired shape, the wall 1807 of the sheath 1603 that includes the plurality of openings may be curved to approximate the shape of the posterior annulus 2003. This can be achieved by, for example, providing the sheath 1603, the LA arm 1704 of the first anchor 1612, or both with a shape substantially similar to the shape of the posterior annulus 2003.

It should be noted that the first anchor, the restraining matrix, and the second anchor of the tissue restraining device 1600 are not limited to embodiments shown in FIGS. 16-19, but may also include various features of the first anchor, the second anchor, and the restraining matrix of other embodiments of tissue restraining devices described in the instant disclosure.

Figure 21A:
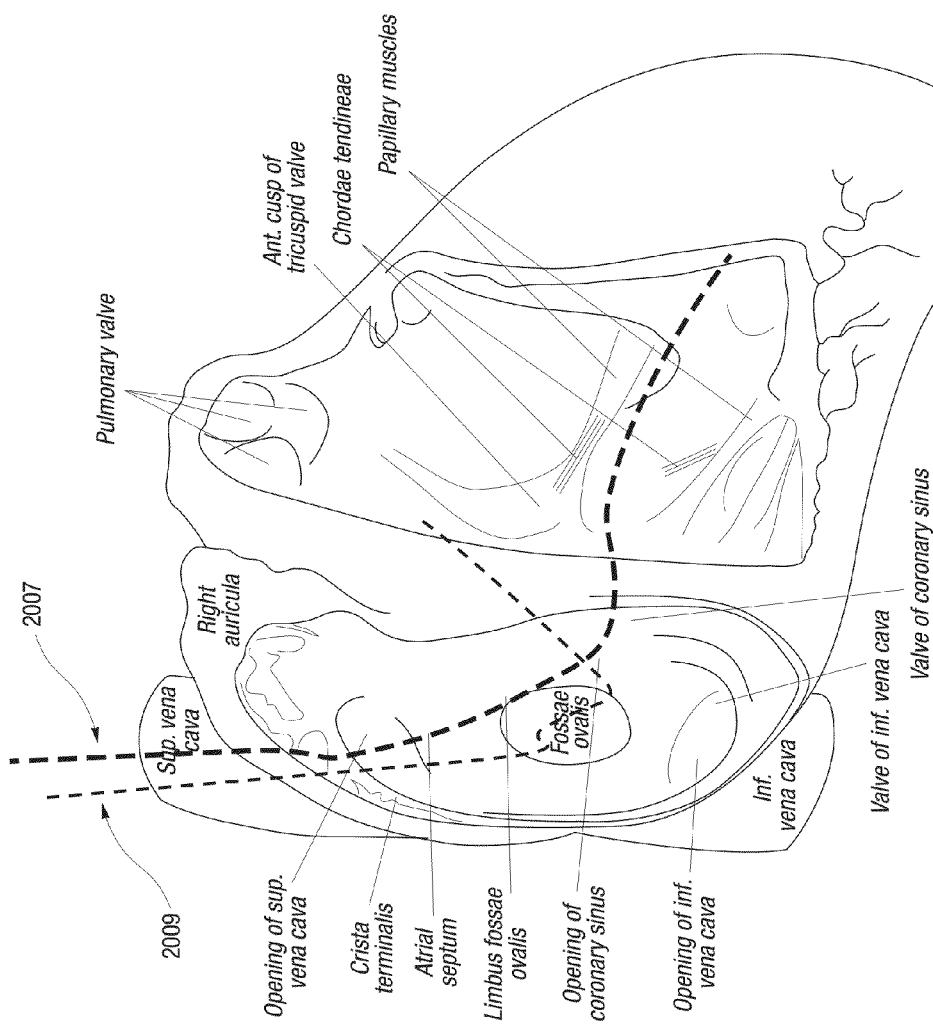
FIGS. 21A-21C illustrate another method for mitral valve repair using a tissue restraining device of the present disclosure.
Figure 21B:
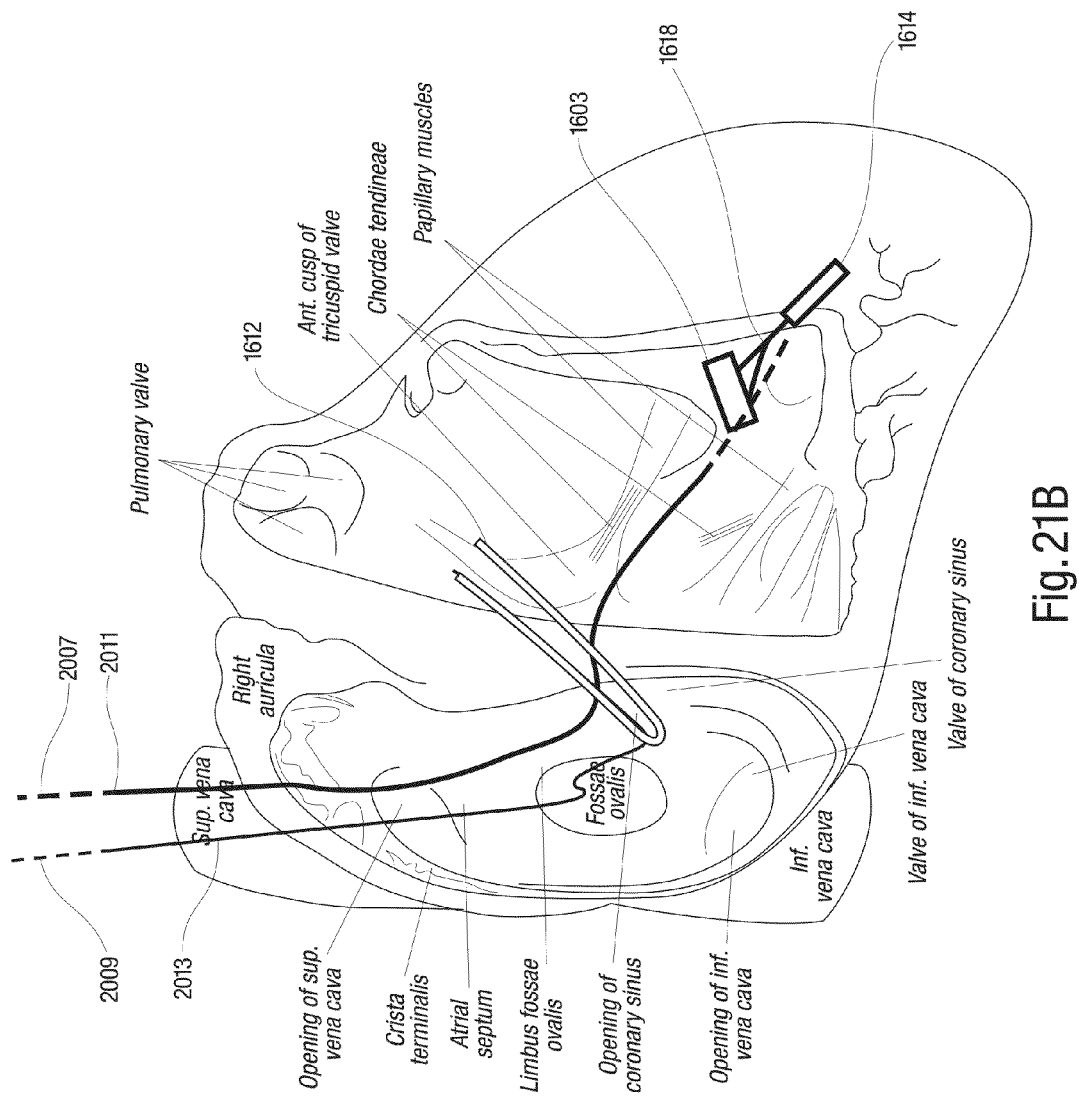
Figure 21C:
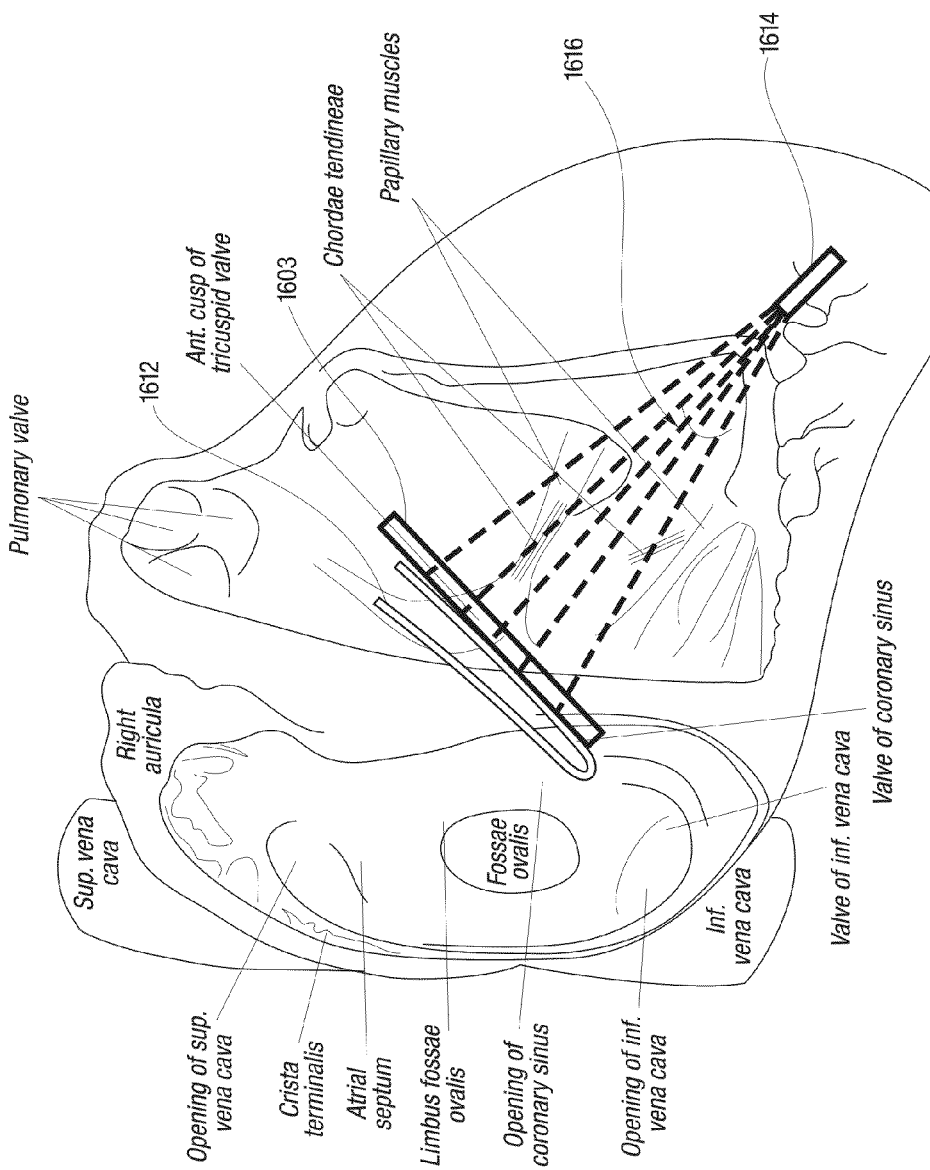

FIGS. 21A-21C illustrate an embodiment of a method for treating a prolapsed mitral valve using a tissue restraining system of the present disclosure. By way of a non-limiting example, a transeptal guidewire 2007 may be advanced into the left ventricle of a patient heart. In an embodiment, the transeptal guidewire 2007 may be advanced along the coronary sinus past the coronary sinus ostium, at which point the transeptal guidewire may be directed out of the coronary sinus, into the left atrium through the atrial septum and on to the left ventricle. A coronary sinus guidewire 2009 may also be advanced along the coronary sinus to a point in proximity of the mitral valve.

Next, the second anchor 1614 may be advanced over the transeptal guidewire 2007 to the left ventricle of the heart of a patient. In an embodiment, the second anchor 1614 may be placed in or around the apex of the heart in the left ventricle. In addition, the sheath 1603 may also be delivered to a temporary position distal of the mitral valve over the transeptal guidewire 2007. That is, the transeptal guidewire 2007 may be passed through a lumen in the sheath 1603 as the sheath 1603 is advanced to the temporary position in the heart of the patient. In an embodiment, the sheath 1603 may be delivered to the heart with the plurality of restraining cords 1618. The cords 1618 may be coupled to the second anchor 1614 before or after the delivery of the sheath 1603, the restraining matrix 1616, and the second anchor 1614 to the heart of the patient. The sheath 1603 may be stationed at the temporary position over the transeptal guidewire 2007, until the sheath 1603 can be coupled to the first anchor 1612.

In the next step, the first anchor 1612 may be advanced over both the transeptal guidewire 2007 and the coronary sinus guidewire 2009 to its deployment position in the coronary sinus and left atrium. In an embodiment, the transeptal guidewire may be passed through the LA arm 1704 of the first anchor 1612 and the coronary sinus guidewire 2009 may be passed through the CS arm 1702 of the first anchor 1612. In this manner, the transeptal guidewire 2007 and the coronary sinus guidewire 2009 assist in positioning the first anchor 1612 in a desired position with the CS arm 1702 in the coronary sinus and the LA arm 1704 in the left atrium. As noted above, since the CS arm 1702 in the coronary sinus and the LA arm 1704 are biased toward one another, they are able to pinch the common wall in between them thereby securely attaching the first anchor 1612 in proximity to the mitral valve. In an embodiment, the first anchor 1612 may be deployed in a substantially opposing relation to the apical anchor 2005. In an embodiment, the first anchor 1612 may be positioned transverse to the apical anchor 2005.

Subsequent to the deployment of the first anchor, the sheath 1603 may be pulled proximally over the transeptal guidewire to be coupled to the first anchor 1612. In an embodiment, the sheath 1603 may include a teether extending from the sheath 1603. By proximally pulling on the teether, the sheath 1603 may be moved proximally over the transeptal wire 2007 to be coupled with the first anchor 1612. In an embodiment, the sheath 1603 may be pulled over the LA arm 1704 of the first anchor 1612. Once the sheath 1603 is coupled to the first anchor 1612, the restraining matrix 1616 may be formed between the first anchor 1612 and the second anchor 1614. In an embodiment, the restraining matrix 1616 may be fan-shaped about the mitral valve. The individual cords 1618 may then be adjusted until all prolapsing segments of the mitral valve are corrected. Individual cords 1618 may be tightened or loosened by pulling on individual cords. Once the individual cords 1618 have been adjusted, they can be fixated in their respective positions and trimmed to remove extra material, as desired. The restraining matrix 1616 may thus provide support to one or more prolapsing segments of the mitral valve.

Figure 22A:
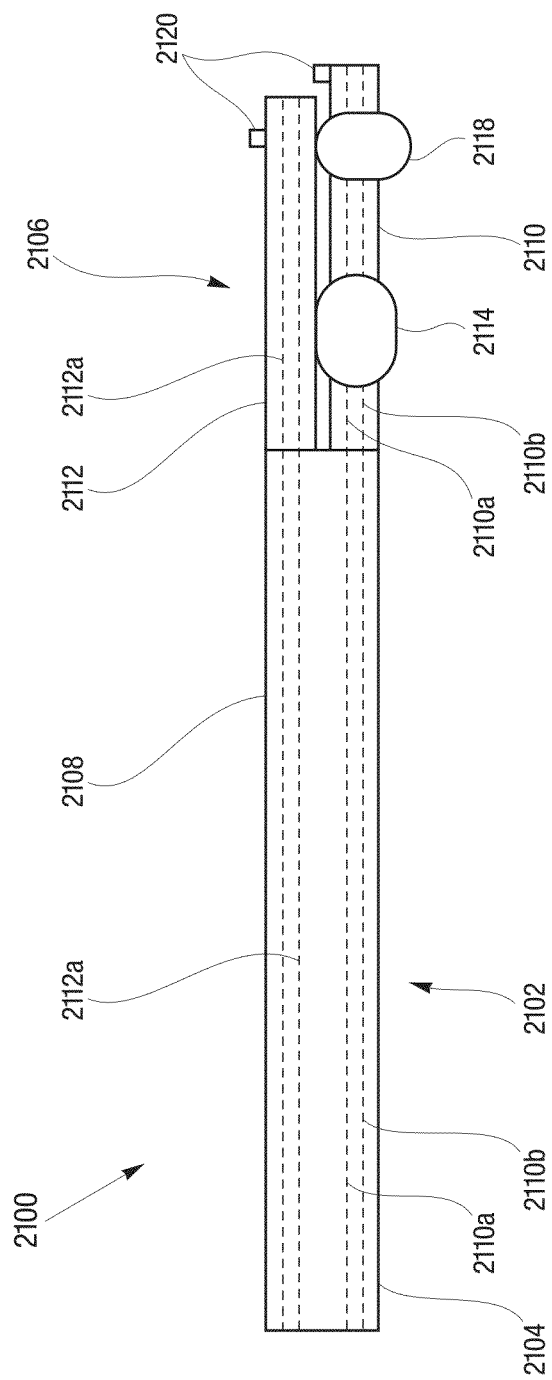
FIGS. 22A-22B is a schematic view of an embodiment of a system for accessing a body organ of the present disclosure.

A device 2100 to provide access to a body organ, such as a heart, is shown generally in FIG. 22A. The device 2100 includes, in one embodiment, an elongated member 2102 having a proximal section 2104, a distal section 2106, and a longitudinal axis extending the length of the elongated member 2102. Throughout this description, the term "proximal" is used to denote the side of an article that is closest to the user, and the term "distal" is used to denote the side of an article that is furthest away from the user. The elongated member 2102 may be designed to navigate along a guide wire, a guide catheter, or both to a site of access to a body organ. To that end, the member 2102 may be sufficiently rigid axially along its length, while remaining sufficiently flexible radially from side to side. In an embodiment, the elongated member 2102 may be made from a biocompatible material, such as a biocompatible plastic or other comparable material. The elongated member 2102 may include at least one inner lumen 2110a, 2110b, 2112a for passing materials or instrumentation therethrough.

Figure 22B:
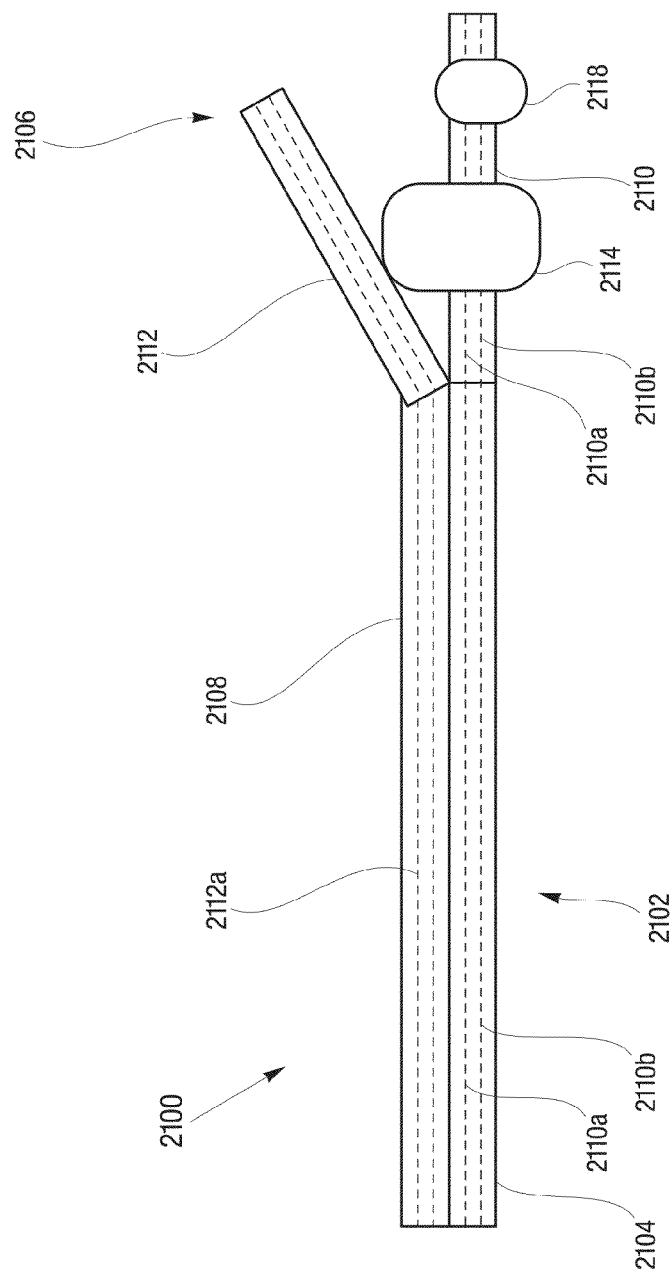

In an embodiment, the distal end 2106 of the elongated member 2102 may include a first extension member 2110 and a second extension member 2112 in a substantially parallel relation to one another. In an embodiment, the first extension member 2110 and a second extension member 2112 form the distal section 2106. In such an embodiment, the elongated member 2102 may include a body 2108, with the first extension member 2110 and the second extension member 2112 extending distally beyond the body 2108. As illustrated in FIGS. 22A and 22B, the elongated member 2102 may include a first inner lumen 2110a that may extend through the elongated member 2102 and the first extension member 2110 to enable passing of materials or instrumentation, such as, a guidewire, through the elongated member 2102 and the first extension member 2110. Moreover, the elongated member 2102 may include a second inner lumen 2112a that may extend through the elongated member 2102 and the second extension member 2112 to enable passing of materials or instrumentation, such as, a guidewire, through the elongated member 2102 and the second extension member 2112.

The second extension member 2112 may, in an embodiment, be configured to be radially deflectable relative to the elongated member 2102. In this manner, the second extension member 2112 may be aimed at an organ to which access is sought ("organ of interest"), such that an instrument may be substantially accurately directed and advanced through the second inner lumen 2112a to penetrate a wall of the organ of interest. By design, the second extension member 2112 may be moveable from a first aligned position, as shown in FIG. 22A, to a second deflected position, as shown in FIG. 22B. In the aligned position, the second extension member 2112 may be substantially aligned with the elongated member 2102, so that the elongated member 2102 may be navigated to and from a site for accessing the organ of interest with minimal interference from the second extension member 2102. In the deflected position, the second extension member 2112 may be substantially radially deflected relative to the elongated member 2102, so that the inner lumen 2112a of the second extension member 2112 may be aligned in the direction of the organ of interest.

The first extension member 2110, on the other hand, may be configured to be substantially stationary. In this manner, a guidewire may be extended through the elongated member 2102 and the first extension member 2110 to permit navigation of the device 2100 along the guidewire to a site for accessing the organ of interest. In an embodiment, the first extension member 2110 may be configured to remain in substantial alignment with the elongated member 2102, regardless of the position of the second extension member 2112. In this manner, the first extension member 2110 may be used as a point from which the second extension member 2112 can be pushed into the deflected position. In an embodiment, when the second extension member 2112 is in the aligned position, the second extension member 2112 and the first extension member 2110 may be positioned side by side in a substantially parallel relationship. On the other hand, when the second extension member 2112 is in the deflected position, the second extension member 2112 and the first extension member 2110 may be positioned at an angle relative to one another.

In certain embodiments, the lengths of the extension members 2110, 2112 may be shorter than that of the body 2108, as illustrated in FIGS. 22A and 22B, while in other embodiments, their lengths may be similar or longer than the length of the body 2108. In one embodiment, the length of the first extension member 2110 beyond the body 2108 may be the same as that of the second extension member 2112. In another embodiment, the length of the first extension member 2110 beyond the body 2108 may be different than that of the second extension member 2112. By providing the extension members 2110, 2112 with different or similar lengths, the extension members 2110, 2112 may be able to accommodate the uneven curvatures or surfaces at the site for accessing the organ of interest.

Figure 23:
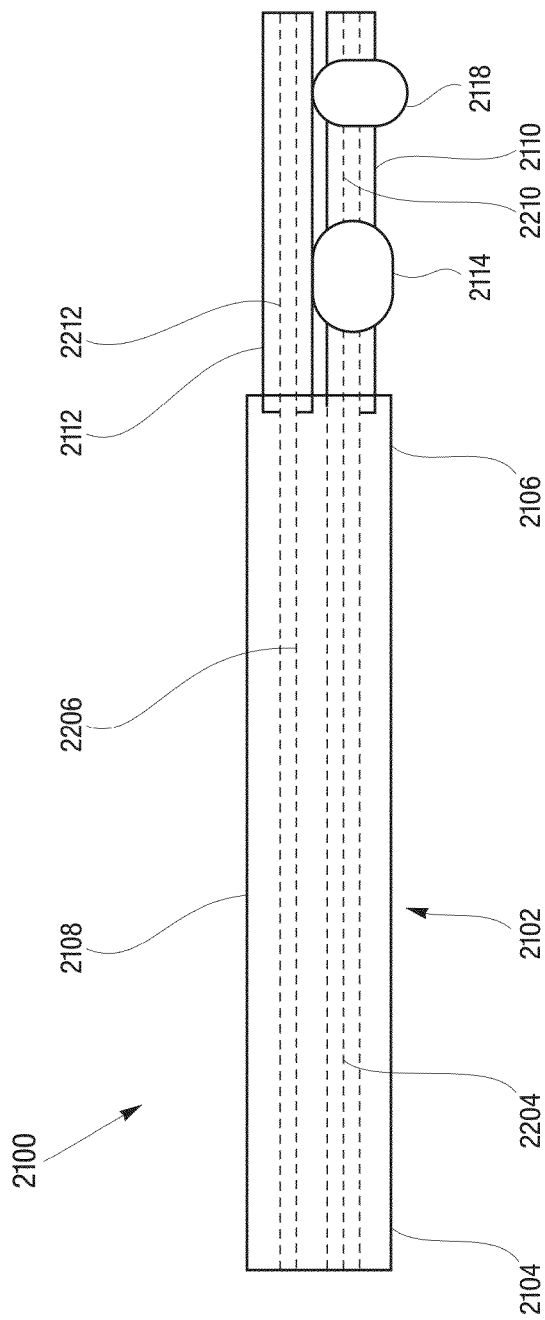
FIG. 23 is a schematic view of another embodiment of a system for accessing a body organ of the present disclosure.

In an alternative embodiment, as illustrated in FIG. 23, the first extension member 2110 and the second extension member 2112 may have a substantially long lengths so they can be slidably inserted into the body 2108 to extend distally of the body 2108. In such an embodiment, the body 2108 may function essentially to maintain the first extension member 2110 and the second extension member 2112 in alignment with one another and enable the extension members 2110, 2112 to be deflected relative to one another. In addition, the lengths of the first extension member 2110 and the second extension member 2112 beyond the elongated member 2102 may be independently adjusted by advancing the extension member 2110, 2112 out of the elongated member 2102 or retracting the extension member 2110, 2112 into the elongated member 2102. To that end, the length of the first extension member 2110 beyond the elongated member 2102 may be adjusted to be the same as that of the second extension member 2112, or different than that of the second extension member 2112. Again, by providing the extension members 2110, 2112 with different or similar lengths, the extension members 2110, 2112 may be able to accommodate the uneven curvatures or surfaces at the site for accessing the organ of interest. It will of course be understood that, although body 2108 is provided, the first extension member 2110 and the second extension member 2112 may be maintained in alignment with one another by other known techniques, for instance by the use of a single or multiple bands wrapped about both the extension members.

The first extension member 2110 may, in an embodiment shown in FIG. 23, include at least one inner lumen 2210 for passing materials or instrumentation therethrough. Similarly, the second extension member 2112 may, in an embodiment, include at least one inner lumen 2212 for passing materials or instrumentation therethrough. In one embodiment, the lumens 2210, 2212 of the extension members 2110, 2112 may be in communication with one or more inner lumens 2204, 2206 of the elongated member. In this manner, materials or instrumentation can be passed through the lumens 2204, 2206 of the elongated member 2102 and into the lumens 2210, 2212 of the first and second extension members 2110, 2112, respectively, for delivery out of the extension members 2110, 2112.

To minimize or reduce friction as the elongated member 2102 travels to a site of access to the organ of interest, the outer surface of the elongated member 2102 and the extension members 2110, 2112 may be coated with material that reduces friction. Similarly, inner surfaces of the lumens of the elongated member 2102 and the extension members 2110, 2112 may also be coated to minimize or reduce friction between the surfaces and materials or instruments being passed through the lumens of the device 2100. Suitable materials include, but are not limited to, polyvinylpyrrolidone, polyurethane, poly(acrylic acid), poly(methacrylic acid), poly(dimeth)acrylamide, PTFE, poly(acrylamide), polyvinybutyrol, poly(hydroxyethylmethacrylate) or combinations thereof. The outer surfaces of the elongated member 2102 and the extension members 2110, 2112 may also be coated with an anti-thrombogenic coating, such as heparin (or its derivatives), urokinase, or PPack (dextrophenylalanine proline arginine chloromethylketone) to prevent thrombosis or any other adverse reaction due to the introduction of the elongated member 2102 into the body of a patient.

To deflect the second extension member 2112 relative to the elongated member 2102 and the first extension member 2110, the device 2100 may further include a deflection mechanism 2114 disposed on the first extension member 2110, as shown in FIGS. 22A-22B. In an embodiment, the deflection mechanism 2114 may be activated to move the second extension member 2112 from the first aligned position, in which the second lumen is substantially parallel to the first extension member 2110, as shown in FIG. 22A, to the second deflected position, in which the second extension member 2112 is substantially radially deflected from the first extension member 2110, as shown in FIG. 22B, while the first extension member 2110 remains substantially aligned with body 2108. The design of the deflection mechanism may be selected based on the anatomy and/or application to ensure that the second extension member 2112, when deflected to the second deflected position, aims at a the organ of interest. It will of course be understood that the deflection mechanism may, in an embodiment, be disposed on the second extension member 2112, i.e. the extension member that is being deflected.

Figure 24C:
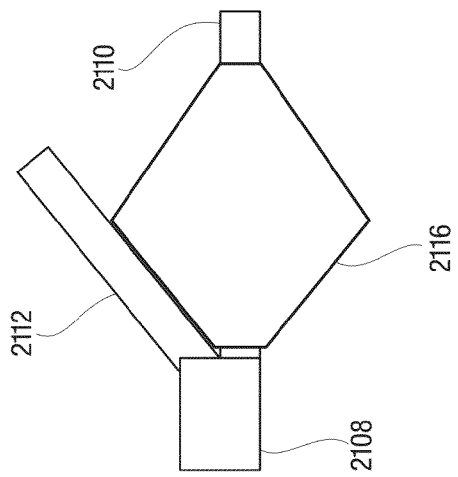
FIGS. 24A-24C illustrate various shapes of an embodiment of a deflection mechanism of the present disclosure
Figure 24B:
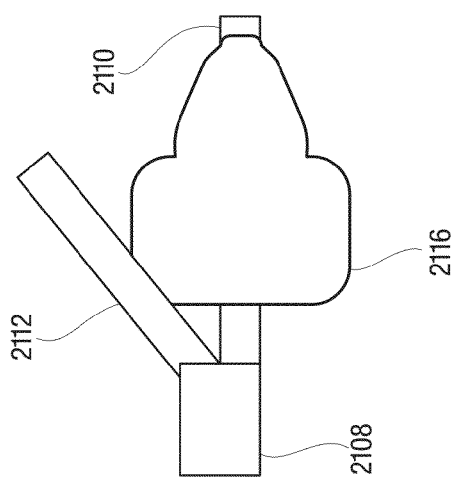
Figure 24A:
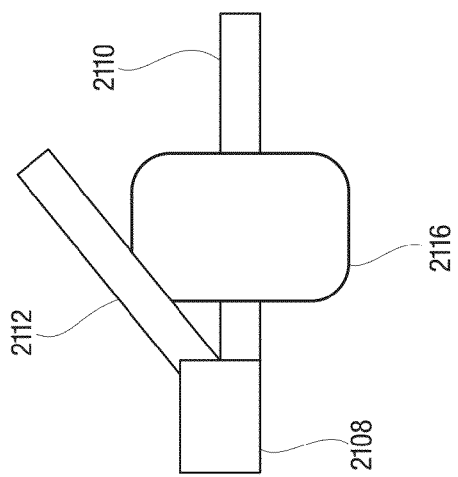

In one embodiment, the deflection mechanism 2114 may be an inflatable device 2116 of a desired shape. The inflatable device 2116 may disposed on the first extension member 2110. The inflatable device 2116 may, in various embodiments, be round, cylindrical, conical, double-conical, tapered, oval, rectangular or may be provided with any other desired shape. By way of a non-limiting example, FIGS. 24A-24C illustrates exemplary inflatable members 2116 of various suitable shapes. The inflatable device 2116 may be formed of a pliable, resilient, conformable, and strong material, including but not limited to urethane, polyethylene terephthalate (PET), nylon elastomer and other similar polymers. In an embodiment, the size and shape of the inflatable device 2116 may depend on, for example, the anatomy of the organ of interest, as is describe below, and can be determined from medical literature, patient observation, or both. Depending on the anatomy and location of the organ of interest, the second extension member 2112 may have a length similar or different than that of the first extension member 2110 so as the second extension member 2112 is provided with sufficient length to be placed in proximity of a body organ of interest.

To actuate the inflatable device 2116, a third lumen 2110b may be provided so as to extend through the elongated member 2102 and the first extension member 2110 (referred herein to as an inflation lumen 2110b). The inflatable device 2116, in one embodiment, may be inflated with a fluid, such as for example, saline. In some embodiment, the inflatable device 2116 may be inflated with a contrast solution, such that the inflatable device 2116 may be easily observed during the procedure with known imaging techniques. Of course, a gas can also be used to inflate the inflatable member 2116. The inflatable device 2116 on the first extension member 2110 may be configured to move the second extension member 2112 from the first aligned position, when the inflatable device 2116 is inflated, to the second deflated position to place the second extension member 2112 in a desired position. On the other hand, the inflatable device 2116 on the first extension member 2110 may be configured to allow the second extension member 2112 to return to the first aligned position along the first extension lumen 2110, when the inflatable device 2116 is deflated, to facilitate removal of the device 2100 from the patient.

In another embodiment, the deflection mechanism 2110 may be a self-expanding device 2400 of a desired shape, as shown in FIGS. 25A-25B. Such self-expanding device 2400 may be, in various embodiments, round, cylindrical, conical, double-conical, tapered, oval, rectangular or may be provided with any other desired shape. The self-expanding device 2400 may, in an embodiment, be formed of a shape memory materials, including, but not limited to, nickel-titanium based alloys, indium-titanium based alloys, nickel-aluminum based alloys, nickel-gallium based alloys, copper based alloys, gold-cadmium based alloys, silver-cadmium based alloys, indium-cadmium based alloys, manganese-copper based alloys, iron-platinum based alloys, and iron-palladium based alloys. In an embodiment, the self-expanding device 2400 may be restricted to a substantially small diameter by using a sheath 2402 during the delivery of the self-expanding device 2400 to a site of access to the organ of interest. In such an embodiment, the device 2100 may include an actuating wire 2404 extending through the elongated member 2102, first extension member 2110, or both and connected to the sheath 2402 for actuating the sheath. To activate the self-expanding device 2400 may be activated, i.e. allow the self-expanding device 2400 to expand, the sheath 2402 may be pulled proximally by the actuating wire 2404 to uncover the self-expanding device 2400 To collapse the self-expanding device 2400, the sheath 2402 may be advanced by the actuating wire 2404 distally to cover the self-expanding device 2400. The self-expanding member 2400 may be configured to move the second extension member 2112 from the first aligned position to the second deflated position when the self-expanding device 2400 is expanded, to place the second extension member 2112 at a desired position. On the other hand, the self-expanding member 2400 may be configured to allow the second extension member 2112 to return to the first aligned position, along the first extension member 2110, when the self-expanding member 2400 is collapsed, so that the device 2100 may be withdrawn from the patient.

Figure 26A:
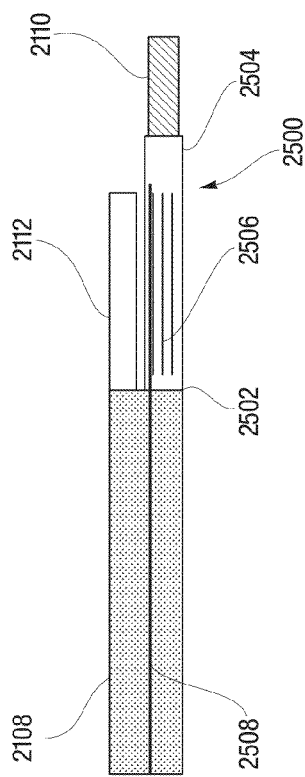
FIGS. 26A-26B illustrate yet another embodiment of a deflection device of the present disclosure.
Figure 26B:
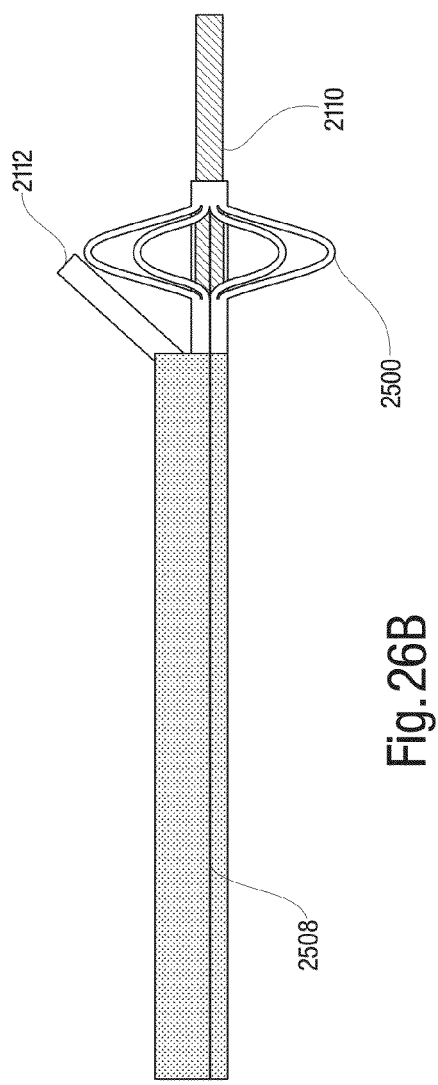

In yet another embodiment, the deflection mechanism 2114 may be a mechanically-expandable device 2500 of a desired shape, as shown in FIGS. 26A-26B. Such mechanically-expandable device may, in various embodiments, be round, cylindrical, conical, double-conical, tapered, oval, rectangular or may be provided with any other desired shape. The mechanically-expandable device 2500 may be formed from a flexible and resilient material, such as plastics or other comparable materials. The mechanically-expandable device 2500 may include a proximal end 2502 and distal end 2504 and a collapsible body 2506 between the proximal end 2502 and the distal end 2504. The mechanically expanding device 2500 may, in an embodiment, be slidably disposed over the first extension member 2110. The mechanically-expandable device 2500 may be moved from a collapsed configuration to an expanded configuration by decreasing the distance between its proximal end 2502 and the distal end 2504, as shown in FIG. 26B. On the other hand, the mechanically-expandable device 2500 may be returned to the collapsed configuration by increasing the distance between its proximal end 2502 and the distal end 2504, as shown in FIG. 26A. In an embodiment, the device 2100 may include an actuating wire 2508 configured to increase or decrease the distance between the proximal end 2502 and the distal end 2504 of the mechanically-expandable device 2500. The mechanically-expandable device 2500 may be configured to move the second extension member 2110 from the first aligned position to the second deflated position, when the mechanically-expandable device 2500 is moved from the collapsed configuration to the expanded configuration, to place the second extension member 2112 into a desired position. On the other hand, the mechanically-expandable device 2500 may be configured allow the second extension member 2112 to return to the first aligned position along the first extension member 2110, when mechanically-expandable device 2500 is collapsed, for example, to allow the device 2100 to be withdrawn from the patient. The mechanically-expandable device 2500 may be connected to the first extension member by any technique that may allow the mechanically-expandable member to be moved from the collapsed configuration to the expanded configuration and back. in an embodiment, the proximal end 2502 of the mechanically-expandable device 2500 may be connected to the elongated member 2102, while the distal end 2504 of the mechanically-expandable device 2500 may be connected to the first extension member.

Referring back to FIGS. 22A and 22B, the device 2100 may, in an embodiment, further include a stopper 2118 disposed on the first extension member. The stopper 2118 may be disposed at or near the distal end of the first extension member 2110 in order to anchor the device 2100 in place during the procedure. In an embodiment, the stopper 2118 may be designed to control the depth of advancement of the device 2100 past the site for access the organ of interest. The stopper 2118 may be provided with size sufficient to prevent the device 2100 from advancing beyond a desired distance into a designated cavity. In other words, the stopper 2118 may be provided with a size sufficiently large to minimize its entrance from a cavity into another cavity with a relatively smaller diameter. The stopper 2118 may be inflatable, self-expanding, or mechanically-expanded, such as described above in regard to the deflection mechanism 2114.

Figure 27B:
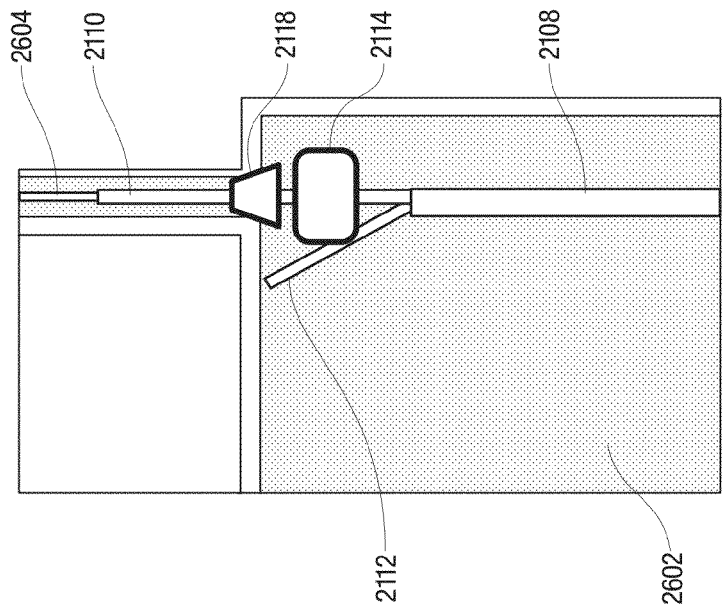
FIG. 27B illustrates an embodiment of a system for accessing a body organ of the present disclosure where a deflection mechanism is distinct from a stopper.
Figure 27A:
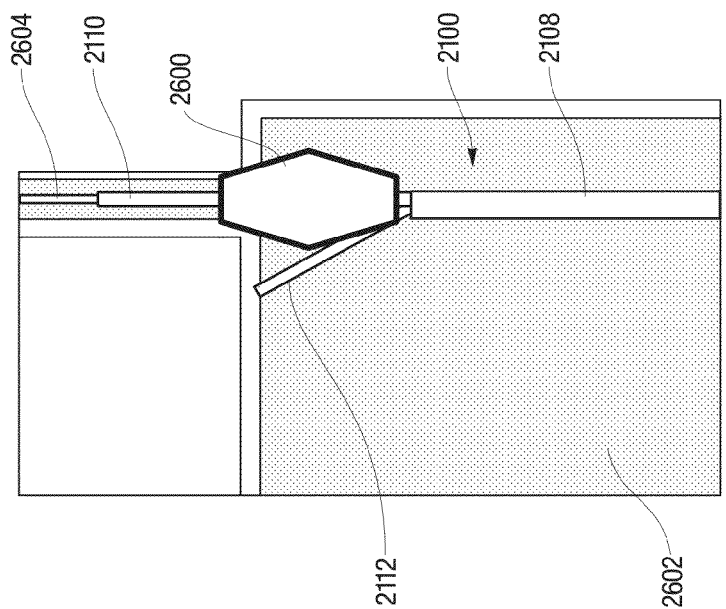
FIG. 27A illustrates an embodiment of a system for accessing a body organ of the present disclosure where a deflection mechanism is integrated with a stopper.

In an embodiment, the deflection mechanism 2114 and the stopper 2118 may be integrated. For example, as illustrated in FIG. 27A, the mechanism 2600 may be configured to deflect the second extension member 2112 radially away from the first extension member 2110, and thus serve as the deflection mechanism 2114. Moreover, the mechanism 2600 may also configured to limit the depth of advancement of the device 2100 from a body cavity 2602 having one diameter into a body cavity 2604 having a smaller diameter, and thus serves as the stopper 2118. In another embodiment, as illustrated in FIG. 27B, the deflection mechanism 2114 and the stopper 2118 may be two distinct mechanisms. In such an embodiment, the deflection mechanism 2114 may be responsible for deflecting the second extension member 2112 radially away from the first extension member 2110, while the stopper 2118 may be responsible for limiting the depth of advancement of the device 2100 into the body cavity 2604. Although the device 2100 is illustrated with the deflection mechanism 2114 and the stopper 2118 disposed on the same extension member, the deflection mechanism 2114 and the stopper 2118 may be located on different extension members.

As shown in FIG. 22A, the device 2100 may further include an orientation mechanism 2120. During the procedure, the device 2100 may need to be rotated by the user to place the device 2100 into a desired orientation. The orientation mechanism 2120 may provide the user with the ability to monitor and/or confirm the location and orientation of the device 2100 at any given time during the procedure.

In an embodiment, the orientation mechanism 2120 may include one or more radiopaque ("RO") markers or bands. Such RO markers or bands may be formed from radiopaque materials such as barium sulfate, tantalum, or other materials known to increase radiopacity. The RO markers or bands may be placed at various locations along the elongated member 2102. In an embodiment, the RO markers or bands may be placed at various locations along a length of the first extension member 2110 and the second extension member 2112. The RO markers or bands may allow the user to monitor the location and orientation of the device 2100 during the procedure by, for example, fluoroscopy.

In another embodiment, instead of RO markers or bands, the echogenic or magnetically responsive markers, or both may be employed as the orientation mechanism 2120. The echogenic or magnetically responsive markers may allow the user to monitor the location and orientation of the device 2100 using ultrasound or MRI techniques, respectively.

In yet another embodiment, the orientation mechanism 2120 may include one or more electrical leads. In an embodiment, one or more electrical leads may be positioned at or near the distal end of the elongated member 2102 in a desired pattern. The one or more electrical leads may be configured to detect a unique electrographic pattern when the elongated member is in a desired position and orientation.

In operation, the device 2100 may be used to gain access to a variety of body organs. By way of a non-limiting example the device 2100 may be employed to gain access to the left atrium of a heart via a transeptal approach, as illustrated in FIGS. 28A-28D.

First, a peripheral venous access may be obtained via, for example, internal jugular, subclavian, or femoral veins. A guidewire 2700 of appropriate stiffness may then be introduced into peripheral venous system (not shown) and advanced through the right atrium 2702 into coronary sinus (CS) 2704, as shown in FIG. 28A. The advancement of a guidewire into coronary sinus may be performed under fluoroscopic guidance, echocardiographic guidance or both using a variety of imaging techniques. In an embodiment, a guidewire may be introduced into CS using a CS guide catheter. For the purpose of clarity, the guidewire introduced into CS may be referred herein to as the CS guidewire.

Figure 28B:
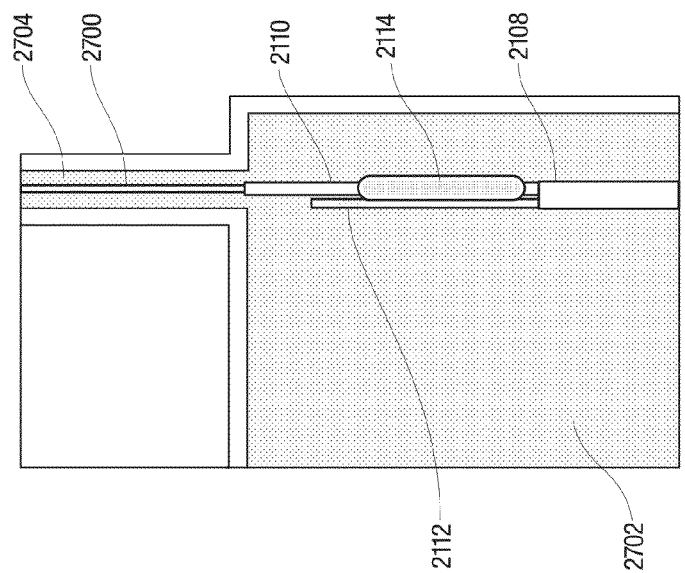
Figure 28A:
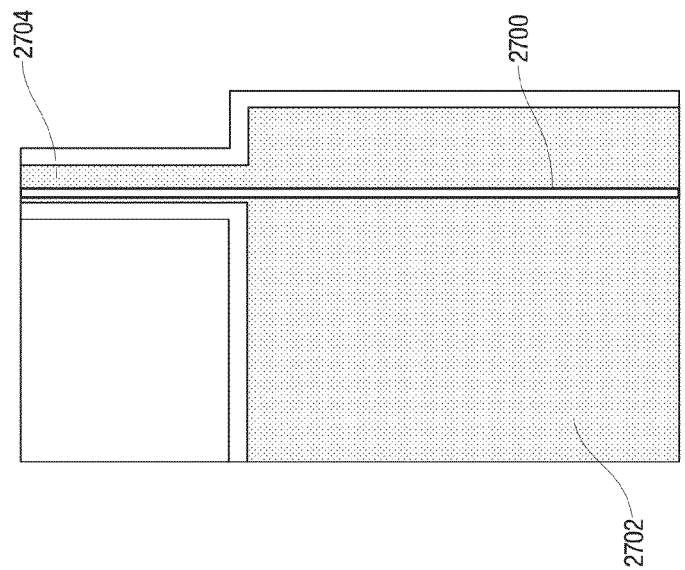
Figure 28C:
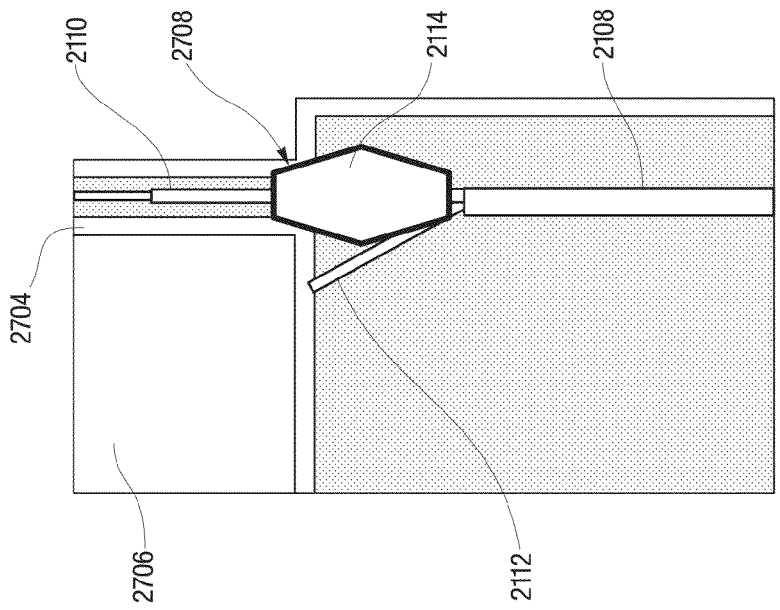
Figure 28D:
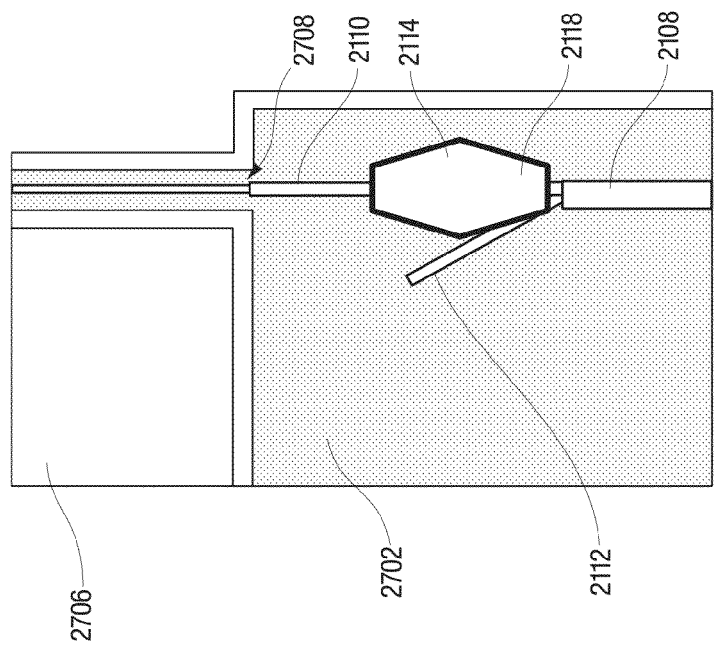

Once the CS guidewire 2700 is in place in CS 2704, the device 2100 may be advanced over the CS guidewire 2700 into the right atrium 2702, as shown in FIG. 28B The CS guidewire 2700, in an embodiment, may be passed through an inner lumen of the body 2108 of the elongated member 2102 and an inner lumen of the first extension member 2110. When the device 2100 is inside the right atrium 2702, the stopper 2118, which in FIGS. 28A-28D is illustrated as integral with the deflation mechanism 2114, on the first extension member 2110 may be activated, as shown in FIG. 28C. The device 2100 may then be advanced further along the CS guidewire 2700 until the stopper 2118 engages the CS ostium 2708. At this point, the device 2100 is at the site of access into the left atrium 2706.

Next, the deflection mechanism 2114 on the first extension member 2110 may be activated to radially deflect the second extension member 2112 to a desired position. In one embodiment, the desired position of the second extension member 2112 may be such that the distance between the distal tip of the first extension member 2110 and the distal tip of the second extension member 2112 is greater that the radius of CS ostium 2708. In other words, the desired position of the second extension member 2112 may be, in an embodiment, such that when the second extension member 2112 is deflected, the distal tip of the second extension member 2110 is outside the CS ostium 2708. It should of course be understood that in the embodiments where the deflection mechanism also serves as a stopper, the deflection mechanism may be activated before the device 2100 is at the site of access to the left atrium. In this manner, the device 2100 may be prevented from being advanced past the site of access to the left atrium.

Once the second extension member 2112 is deflected, the device 2100 may be oriented, with the aid of the orientation mechanism 2120, such that the distal end of the second extension member 2112 is aimed at the atrial septum. Another guidewire 2710, referred herein to as the left atrium (LA) guidewire or transeptal guidewire, may then be advanced through an inner lumen of the body 2108 of the elongated member 2102 and an inner lumen of the second extension member 2112 to penetrate a tissue, i.e. the atrial septum, to enter the left atrium 2706, as shown in FIG. 28E. At this point, the device 2100 may be removed from the patient, and the LA guidewire 2710 may be used for the advancement of catheters or other devices into the left atrium 2706. For example, the left atrium guidewire 2710 may be utilized to advance catheters or other devices into the left atrium 2706 for such procedures as mitral valve intervention, ablation, left atrium appendage intervention among others. In an embodiment, the left atrium guidewire 2710 may be further advances into the left ventricle By way of non-limiting example, when the device 2100 may be withdrawn, the CS guidewire 2700 may be left in place. In such an embodiment, the CS guidewire 2700 and the LA or transeptal guidewire 2710 may be used as described above to deploy a tissue restraining device of the present disclosure to repair a prolapsing mitral valve.

The devices, systems and methods of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the devices and methods of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Restraining a Native Mitral Valve In Vivo

The goal of the study was to assess whether a set of cords emanating from the coronary sinus (CS), entering the left atrium (LA) just above the posterior mitral annulus, traversing the orifice of the mitral valve and anchored to the left ventricle (LV) apex can restrain a prolapsing P2 segment and eliminate mitral regurgitation (MR).

Figure 29B:
FIGS. 29A-29N illustrate steps of an exemplary procedure to restrain a native mitral valve in vivo using a tissue restraining device of the present disclosure.
Figure 29D:
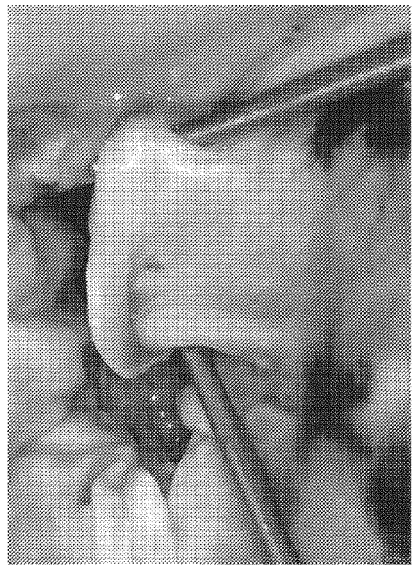
Figure 29A:
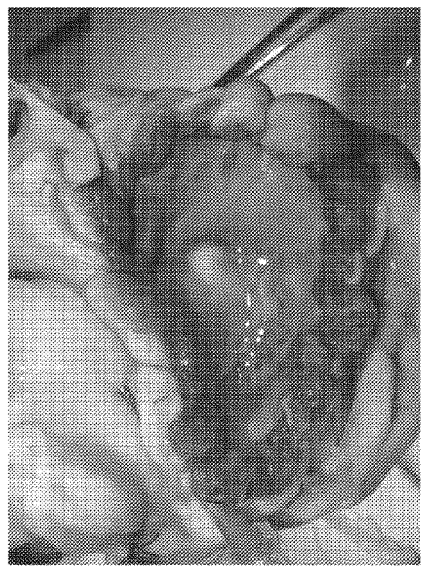
Figure 29C:
Figure 29F:
Figure 29H:
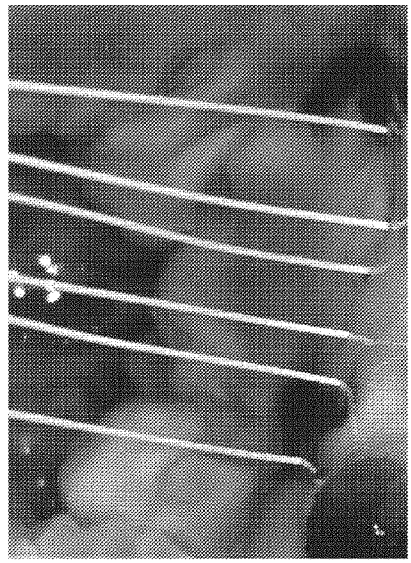
Figure 29E:
Figure 29G:
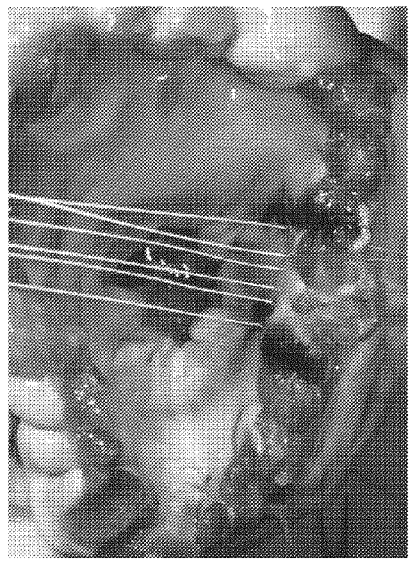
Figure 29J:
Figure 29L:
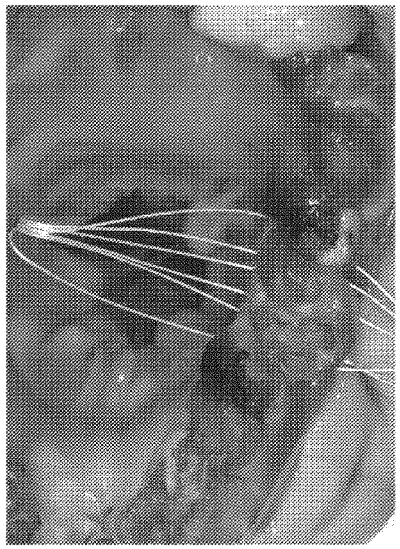
Figure 29I:
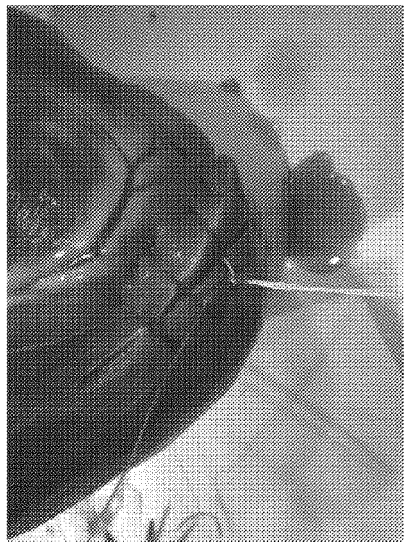
Figure 29K:
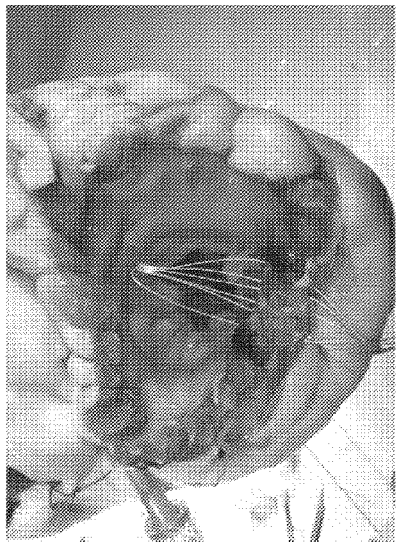
Figure 29N:
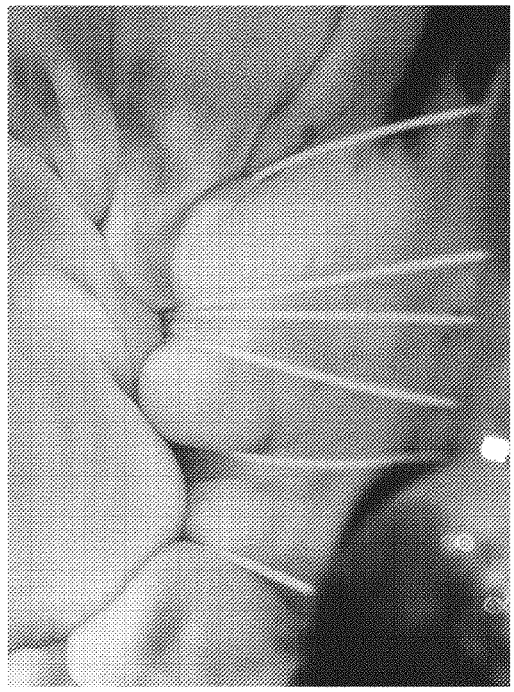

The steps of this procedure are presented in FIGS. 29A-29N. An isolated calf heart was utilized. Atria was excised, coronaries were ligated, aortic valve was excised, ascending aorta was overseen and CS was unroofed. Saline was infused into a ascending aorta through a 16 gauge needle to pressurize the left ventricle, as shown in FIGS. 29A-29B.

P2 segment was marked as shown in FIGS. 29C and 29D. Multiple cordae tendinae to P2 segment of the valve were cut to create a prolapse and MR, as shown in FIGS. 29E and 29F.

To fix the prolapse, five individual CV-5 Gortex sutures were passed from CS into LA just above the annulus of the mitral valve just above P2 segment, as shown in FIGS. 29G and 29H.

The sutures were spaced about 2 mm apart and spanned the prolapsing P2 segment. The distal ends of sutures were tied together, passed through the mitral valve and LV apex, and anchored to LV apex with another suture, as shown in FIGS. 29I and 29J.

Figure 29M:
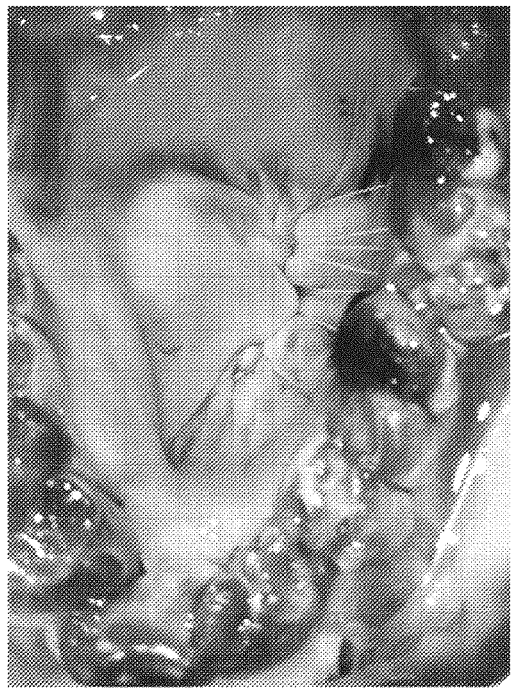

The sutures, which are shown as loose in FIGS. 29K and 29L, were tightened to restrain the prolapsing segment P2 and eliminate MR, as shown in FIGS. 29M and 29L.

All patents, patent applications, and published references cited herein are hereby incorporated by reference in their entirety.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A tissue restraining device comprising:
   an annuloplasty member for attachment to a valve annulus of a cardiac valve, the annuloplasty member defining an opening;
   an anchor having a loop and situated in a spaced relation to the annuloplasty member on an opposite side of the cardiac valve;
   a plurality of restraining cords forming a restraining matrix extending from the annuloplasty member into the opening and toward the anchor so that when the tissue restraining device is implanted, the restraining matrix is draped over a leaflet of the cardiac valve, the restraining cords converging at their distal ends to form an apex between the annuloplasty member and the anchor; and
   a tensioning strand extending distally from the apex of the restraining matrix, passing through the loop, and extending through the annuloplasty member so the restraining matrix is adjustable as a single unit to change a tension in the restraining matrix.

2. The device of claim 1, wherein each restraining cord of the plurality of restraining cords is removably attached at or proximally to a longitudinal end of the annuloplasty member to change the tension in the restraining matrix.

3. The device of claim 2, wherein the plurality of restraining cords are individually adjustable to change a tension in the restraining matrix.

4. The device of claim 1, wherein the annuloplasty member includes a second tensioning strand to provide a tying point for the tensioning strand.

5. The device of claim 1, wherein the annuloplasty member is configured to be implanted substantially along an annulus of a mitral valve, the anchor is configured to be implanted in a left ventricle, and, when the restraining device is implanted into the mitral valve, the restraining matrix is extended between the annuloplasty member and the anchor to drape over the leaflet.

6. The device of claim 1, wherein the annuloplasty member includes one or more inner lumen and a plurality of openings in communication with the one or more inner lumen to allow the plurality of restraining cords to be passed through the one or more inner lumen of the annuloplasty member and out of the plurality of openings to form the restraining matrix.

7. The device of claim 1, wherein the restraining matrix further comprises cross-restraint members extending between the plurality of the restraining cords.

8. A kit for restraining tissue comprising:
a restraining matrix formed by a plurality of restraining cords,
wherein the plurality of restraining cords are spread out at a proximal end of the restraining matrix and are collected together at a distal end of the restraining matrix to form an apex between an annuloplasty member and an anchor so that the proximal end is broader than the distal end;
an attachment member disposed at the proximal end of the restraining matrix and designed to removably attach to an annuloplasty ring,
the anchor having a loop and attached to the distal end of the restraining matrix; and
a tensioning strand extending distally from the apex of the restraining matrix, and to pass through the loop, and extend through the annuloplasty member so the restraining matrix is adjustable as a single unit to change a tension in the restraining matrix.

9. The kit of claim 8 wherein the attachment member includes a plurality of hooks for insertion into the annuloplasty ring to attach the restraining matrix to the annuloplasty ring.

10. The kit of claim 8, wherein the restraining matrix is formed by the plurality of restraining cords, each restraining cord of the plurality of cords is in communication with an opening spaced apart, evenly or unevenly, from one another along a posterior section of the annuloplasty ring.

11. A tissue restraining device comprising:
an annuloplasty member for attachment to a valve annulus of a valve, the annuloplasty member having a bottom side to contact the valve annulus, a top side opposite the bottom side, and an inner sidewall and an outer sidewalls connecting the bottom side and the top side;
an anchor situated in a spaced relation to the annuloplasty member;
a restraining matrix formed by a plurality of restraining cords extending from the inner sidewall of the annuloplasty member toward the anchor, the restraining cords converging at their distal ends to form an apex between the annuloplasty member and the anchor; and
a tensioning strand extending distally from the apex of the restraining matrix through the anchor and proximally of the annuloplasty member so the restraining matrix is adjustable as a single unit for changing a tension in the restraining matrix proximally to or at the annuloplasty member from a distal direction of the restraining matrix.

12. The device of claim 11, wherein the annuloplasty member includes one or more inner lumen and a plurality of openings disposed along the inner sidewall in communication with the one or more inner lumen to allow the plurality of restraining cords to be passed through the one or more inner lumen of the ring and out of the plurality of openings to form the restraining matrix.

13. The device of claim 11, wherein the tensioning strand extends distally from the restraining matrix, passes through a loop of the anchor, and extends through the annuloplasty member to change the tension in the restraining matrix.

14. The device of claim 11, wherein a second tensioning strand is fixed on the annuloplasty member, the tensioning strand and second tensioning strand are joined to adjustably change the tension in the restraining matrix, at or proximally of the annuloplasty member.

15. The device of claim 11, wherein a chain of loops extends from a distal end of the restraining matrix and the anchor includes at least one hook, such that a loop of the chain of loops is capable of being hooked into the at least one hook, so to change the tension in the restraining matrix from the distal direction of the restraining matrix.

16. The device of claim 1, wherein each restraining cord of the plurality of the restraining cords extends through an opening of an inner lumen positioned along at least a portion of the annuloplasty member, and extends through the annuloplasty member, so each restraining cord of the plurality of the restraining cords is individually adjustable at or proximally of the annuloplasty member to change the tension in the restraining matrix.

17. The device of claim 1, wherein a second tensioning strand is fixed on the annuloplasty member, the tensioning strand and second tensioning strand are joined to adjustably change the tension in the restraining matrix, at or proximally of the annuloplasty member.

18. The device of claim 1, wherein a chain of loops extends from a distal end of the restraining matrix and the anchor includes at least one hook, such that a loop of the chain of loops is capable of being hooked into the at least one hook, so as to be capable of changing the tension in the restraining matrix from the distal direction of the restraining matrix.

* * * * *